United States Patent [19]

Yaver et al.

[11] Patent Number: 5,667,531

[45] Date of Patent: Sep. 16, 1997

[54] DYE COMPOSITIONS CONTAINING PURIFIED POLYPORUS LACCASES AND NUCLEIC ACIDS ENCODING SAME

[75] Inventors: Debbie Sue Yaver, Davis; Feng Xu, Woodland, both of Calif.; Henrik Dalbøge, Virum, Denmark; Palle Schneider, Ballerup, Denmark; Dorrit A. Aaslyng, Værloese, Denmark

[73] Assignees: Novo Nordisk A/S, Bagsvaerd, Denmark; Novo Nordisk Biotech, Inc., Davis, Calif.

[21] Appl. No.: 462,484

[22] Filed: Jun. 5, 1995

Related U.S. Application Data

[62] Division of Ser. No. 441,147, May 15, 1995.

[51] Int. Cl.$^6$ .............. C12N 9/02; C12N 15/31; C12N 15/52

[52] U.S. Cl. .......... 8/401; 8/405; 8/406; 206/823; 222/94; 435/128; 435/156; 435/172.1; 435/254.3; 435/263

[58] Field of Search .............. 8/405, 406, 401; 435/189, 254.3, 128, 156, 263, 810; 222/94; 206/823

[56] References Cited

U.S. PATENT DOCUMENTS

| | | | |
|---|---|---|---|
| 3,251,742 | 5/1966 | Soloway | 167/88 |
| 3,931,912 | 1/1976 | Hsiung | 222/94 |
| 3,957,424 | 5/1976 | Zeffren et al. | 8/401 |
| 4,314,808 | 2/1982 | Jacquet et al. | 8/405 |
| 4,839,279 | 6/1989 | Kosaka et al. | 435/25 |
| 5,156,955 | 10/1992 | Isono et al. | 435/253.4 |
| 5,289,944 | 3/1994 | Wiegner et al. | 222/1 |
| 5,480,801 | 1/1996 | Wahleithner et al. | 435/254.3 |

FOREIGN PATENT DOCUMENTS

| | | |
|---|---|---|
| 0 504 005 A1 | 3/1992 | European Pat. Off. |
| 3634761 C1 | 10/1986 | Germany |
| 4033246 C1 | 10/1990 | Germany |
| WO 95/01426 | 1/1995 | WIPO |

OTHER PUBLICATIONS

Chet et al., Microbios Letters, vol. 29, pp. 37–43, 1985.

Bollag et al., Applied and Environemntal Microbiology, vol. 48., No. 4, pp. 849–854, 1984.

Yaver et al., Gen. Tech. Rep. NC, pp. 115–118, 1994.

Trojanowski et al., Lignin Enzymic and Nicrobial Degradation, pp. 223–227, 1987.

Primary Examiner—Herbert J. Lilling
Attorney, Agent, or Firm—Steve T. Zelson, Esq.; James Harrington, Esq.

[57] ABSTRACT

The present invention relates to isolated nucleic acid constructs containing a sequence encoding a polyporus laccase, and the laccase proteins encoded thereby.

20 Claims, 64 Drawing Sheets

```
                                                                    70
                                                      60
                                        50
                            40
                30
    20
10

AGATTTCTGA CACCGTGCA ATCTTGACAC TGTACCAACC GGGCAAGTCT CGTCCTTGGT TCTCGGGGAC 140
                                                      130
                                        120
                           110
               100
    90
80

TGGCGCCCGGT CGCTACCCCT TGGTCATTCA CTCTACCAGA GCGCTGGCTT CGCCCGAGGTA TAAAGGATGT 210
                                                      200
                                        190
                           180
               170
    160
150

TGGCGCGACAC CCTCAACAAC CCAACTCAAG CCCCACTTGA GCTTTTGCGA GATCCTCCAC ATACCACTCA 266
                                                257
                                   248
                       239
           230
    220

CTACTTTCAA GTTCTTCAAC ATG TCG AGG TTT CAC TCT CTT CTC GCT TTC GTC GTT
                         MET Ser Arg Phe His Ser Leu Leu Ala Phe Val Val 320
                                                 311
                                    302
                        293
            284
    275

GCT TCC CTT ACG GCT GTG GCC CAC GCT GGT ATC GGT GCC GTC GAC CTA ACG
Ala Ser Leu Thr Ala Val Ala His Ala Gly Ile Gly Pro Val Ala Asp Leu Thr
```

FIG. 1A

```
                            329         338         347         356         365         374
                            |           |           |           |           |           |
                        ATC ACC AAC GCA GCG GTC AGC CCC GAC GGG TTT TCT CGC CAG GCC GTC GTC GTG
                        Ile Thr Asn Ala Ala Val Ser Pro Asp Gly Phe Ser Arg Gln Ala Val Val Val 383         392         401         410         423         433
                            |           |           |           |           |           |
                        AAC GGC GGT ACC CCT GGC CCT CTC ATC ACG GGT AAC ATG GTTCGTCTCG GCTCGCACTA
                        Asn Gly Gly Thr Pro Gly Pro Leu Ile Thr Gly Asn MET 443         453         463         473         482         491
                            |           |           |           |           |           |
                        GGGGGTTGTA TCGTTCCTGA CGTTGTTGGA G GGG GAT CGC TTC CAG CTC AAT GTC ATC
                                                            Gly Asp Arg Phe Gln Leu Asn Val Ile 500         509         518         527         543         553
                            |           |           |           |           |           |
                        GAC CTT ACC AAC CAC ACG ATG GTG AAG AGC ACG AGT ATT GTGAGCTGCT ATTTCTCCGG
                        Asp Leu Thr Asn His Thr MET Val Lys Ser Thr Ser Ile 563         573         583         592         601         610
                            |           |           |           |           |           |
                        ACGGGGCTTC ATTGTGCTAA TAATCGTCGT GTGCAG CAC TGG CAC GGT TTC TTC CAG AAG
                                                                His Trp His Gly Phe Phe Gln Lys
```

FIG.1B

```
      619        628        637        646        655        664
       |          |          |          |          |          |
GGT ACC AAC TGG GCC GAC GGT CCC TTC GCC ATC AAC CAG TGC CCG ATC TCA TCT
Gly Thr Asn Trp Ala Asp Gly Pro Phe Ala Ile Asn Gln Cys Pro Ile Ser Ser 673        682        691        700        709        720
       |          |          |          |          |          |
GGT CAC TCG TTC CTG TAC GAC TTC CAG GTT CCT GAC CAG GCT G   GTAAGTACGG
Gly His Ser Phe Leu Tyr Asp Phe Gln Val Pro Asp Gln Ala Gly

779
                                                                        |
TCGTTATGGA GTATACTGCG CATTGCTAAA CCACATGGTG AACAG GT ACC TTC TGG TAT
                                                 Thr Phe Trp Tyr 788        797        806        815        824        833
       |          |          |          |          |          |
CAC AGT CAC TTG TCT ACG CAG TAC TGT GAT GGT TTG AGG GGT CCG TTC GTT GTT
His Ser His Leu Ser Thr Gln Tyr Cys Asp Gly Leu Arg Gly Pro Phe Val Val 842        851        860        869        878        889
       |          |          |          |          |          |
TAC GAC CCG AAT GAC GCC CCG GCC GAC CTG TAC GAC GTC GAC AAC G  GTAAGGACGA
Tyr Asp Pro Asn Asp Ala Pro Ala Asp Leu Tyr Asp Val Asp Asn Asp
```

949
                                                                    GTC ATT
                                                                    Val Ile
                                                              940
                                                                    GAC ACT
                                                                    Asp Thr
                                                              929
                                                                    AC
                                                              919    
                                                                    AATTAG
                                                              909
                                                                    CTTCTCGATG
                                                              899
                                                         ATTCGAACCG TAAATACTTG CTTACTGATA CTTCTCGATG AATTAG AC GAC ACT GTC ATT
                                                                                                     Asp Thr Val Ile 1069
                                                              994              TTC CC   GTAAGTCCAT
                                                                   CCC GCA    Phe Pro
                                                                   Pro Ala
                                                              985  CTG GGC
                                                                   Leu Gly
                                                              976  GCC AAG
                                                                   Ala Lys
                                                              967  GTC GCC
                                                                   Val Ala
                                                              958  CAC TAC
                                                                   His Tyr
                                                                   TGG
                                                                   Trp
                                                                   GAT
                                                                   Asp
                                                                   GTG
                                                                   Val
                                                                   CTT
                                                                   Leu
                                                                   ACC
                                                                   Thr
                                                         ACC CTT GTG GAT TGG TAC CAC GTC GCC AAG CTG GGC CCC GCA TTC CC GTAAGTCCAT
                                                         Thr Leu Val Asp Trp Tyr His Val Ala Lys Leu Gly Pro Ala Phe Pro 1123
                                                              1114             TCA GTT
                                                                   GAC CTC     Ser Val
                                                                   Asp Leu
                                                              1105 GCC ACC
                                                                   Ala Thr
                                                              1096 GCG GAC
                                                                   Ala Asp
                                                              1087 ACC GGG
                                                                   Thr Gly
                                                              1078 ACG GCC
                                                                   Thr Thr
                                                                   AGC
                                                                   Ser
                                                                   TCC
                                                                   Ser
                                                                   CCC
                                                                   Pro
                                                                   CGC
                                                                   Arg
                                                                   GGA
                                                                   Gly
                                                                   AAG
                                                                   Lys
                                                                   AAC
                                                                   Asn
                                                                   ATC
                                                                   Ile
                                                                   CTC
                                                                   Leu
                                                          GAGTATTCTG CTGTTGAATC TGTCTTAACT GTGCATATCA G T CTC GGC GAC GCC ACC
                                                                                          Leu Gly Ala Asp Ala Thr 1186
                                                              1176 TCTGATGGCA TTTCTCTGAG
                                                              1166 TCTTATCTTA
                                                              1156 GTATGCTATA
                                                                   CG
                                                                   AAA
                                                                   Lys Arg
                                                                   CCG GGT
                                                                   Pro Gly
                                                                   ACC
                                                                   Thr
                                                                   GTC
                                                                   Val
                                                                   AGC
                                                                   Ser
                                                                   ATC
                                                                   Ile
                                                          CTC ATC AAC GGT AAG GGA CGC TCC CCC AGC ACG ACC ACC ACC GCG GAC CTC TCA GTT
                                                          Leu Ile Asn Gly Lys Gly Arg Ser Pro Ser Thr Thr Thr Ala Asp Leu Ser Val

ATC AGC GTC ACC CCG GGT AAA CG GTATGCTATA TCTTATCTTA TCTGATGGCA TTTCTCTGAG
                                                          Ile Ser Val Thr Pro Gly Lys Arg
```

FIG. ID

```
                                        1207           1216      1225           1234
ACATTCTCCA G  C  TAC CGT TTC CGC CTG GTG TCC CTG TCG TGC GAC CCC AAC TAC
                 Tyr Arg Phe Arg Leu Val Ser Leu Ser Cys Asp Pro Asn Tyr 1243         1252             1261             1270            1279             1288
    ACG TTC AGC ATC GAT GGT CAC AAC ATG ACG ATC ATC GAG ACC GAC TCA ATC AAC
    Thr Phe Ser Ile Asp Gly His Asn MET Thr Ile Ile Glu Thr Asp Ser Ile Asn 1297         1306             1315             1324            1333             1342
    ACC GCG CCC CTC GTC CTC GAC TCC ATT CAG ATC TTC GCC CAG CCC CGT TAG TCC
    Thr Ala Pro Leu Val Val Asp Ser Ile Gln Ile Phe Ala Gln Arg Tyr Ser 1351         1364             1374             1384            1394             1404
    TTC GTG GTAAGTTCGA TTCATCCCTCT AACGTTGGTC GCTGTTAGTG ATCGTATGGT CATGTAG
    Phe Val
```

*FIG. 1E*

```
1414                1423         1432              1441              1450              1459
     |     |     |     |     |     |     |     |     |     |     |
 CTC  GAG  GCC  AAC  CAG  GCC  GTC  GAC  AAC  TAC  TGG  ATT  CGC  GCC  AAC  CCG  AAC  TTC
 Leu  Glu  Ala  Asn  Gln  Ala  Val  Asp  Asn  Tyr  Trp  Ile  Arg  Ala  Asn  Pro  Asn  Phe 1468                1477         1486              1495              1504              1513
     |     |     |     |     |     |     |     |     |     |     |
 GGT  AAC  GTC  GGG  TTC  ACC  GGC  GGC  ATT  AAC  TCG  GCT  ATC  CTC  CGC  TAC  GAT  GGT
 Gly  Asn  Val  Gly  Phe  Thr  Gly  Gly  Ile  Asn  Ser  Ala  Ile  Leu  Arg  Tyr  Asp  Gly 1522                1531         1540              1549              1558              1567
     |     |     |     |     |     |     |     |     |     |     |
 GCC  GCT  GCC  GTG  GAG  CCC  ACC  ACA  ACG  CAA  ACC  ACG  TCG  ACT  GCG  CCG  CTC  AAC
 Ala  Ala  Ala  Val  Glu  Pro  Thr  Thr  Thr  Gln  Thr  Thr  Ser  Thr  Ala  Pro  Leu  Asn 1576                1585         1594              1603              1619        1629
     |     |     |     |     |     |     |     |     |     |
 GAG  GTC  AAC  CTG  CAC  CCG  CTG  GTT  ACC  ACC  GCT  GTG  GTATGTAATA  TTGTCGGTAA
 Glu  Val  Asn  Leu  His  Pro  Leu  Val  Thr  Thr  Ala  Val
```

*FIG. 1F*

```
                TGTAATACAT TGTTGCTGAC CTCGACCCCC ACAG CCT GGC TCG CCC GTC GCT GGT
                                                      Pro Gly Ser Pro Val Ala Gly Gly

GTC GAC CTG GCC ATC AAC ATG GCG TTC AAC GGC ACC AAC TTC ATC
     Val Asp Leu Ala Ile Asn MET Ala Phe Asn Gly Thr Asn Phe Ile

AAC GGC ACG TCT TTC ACG CCC CCG ACC GTG CCT CTG CTC CAG ATC AGC
     Asn Gly Thr Ser Phe Thr Pro Pro Thr Val Pro Val Leu Leu Gln Ile Ser

GGC GCG CAG AAC GCG CAG GAC CTC CTG CCC TTC GGT AGC GTC TAC TCG CTT CCC
     Gly Ala Gln Asn Ala Gln Asp Leu Leu Pro Ser Gly Ser Val Tyr Ser Leu Pro

TCG AAC GCC GAC ATC GAG ATC TCC TTC CCC GCC ACC GCC GCC CCC GGT GCG
     Ser Asn Ala Asp Ile Glu Ile Ser Phe Pro Ala Thr Ala Ala Pro Gly Ala
```

FIG. 1G

```
       1912           1921           1930           1939           1948           1957
 CCC   CAC   CCC   TTC   CAC   TTG   CAC   GGG   CAC   GCG   TTC   GCG   CAC   GTC   CGC   GTC   AGC   GCC   GGC
 Pro   His   Pro   Phe   His   Leu   His   Gly   His   Ala   Phe   Ala   His   Val   Val   Arg   Ser   Ala   Gly 1966           1975           1984           1993           2002           2011
 AGC   ACG   GTC   TAC   AAC   TAC   GAC   AAC   CCC   ATC   TTC   CGC   CAC   GTC   CAC   GTC   AGC   ACG   GGG
 Ser   Thr   Val   Tyr   Asn   Tyr   Asp   Asn   Pro   Ile   Phe   Arg   Asp   Val   Val   Ser   Thr   Gly 2020           2029           2038           2047           2056           2065
 ACG   CCT   GCG   GCC   GGT   GAC   AAC   GTC   ACC   ATC   CGC   TTC   CGC   GAC   AAC   ACC   CCC   GGC
 Thr   Pro   Ala   Ala   Gly   Asp   Asn   Val   Thr   Ile   Arg   Phe   Arg   Asp   Asn   Pro   Gly 2074           2083           2092           2101           2110           2119
 CCG   TGG   TTC   CTC   CAC   TGC   CAC   ATC   GAC   TTC   CAC   CTC   GAG   GCC   GGC   TTC   GCC   GTC
 Pro   Trp   Phe   Leu   His   Cys   His   Ile   Asp   Phe   His   Leu   Glu   Ala   Gly   Phe   Ala   Val
```

*FIG. 1H*

```
                    2128              2137              2146              2155              2164              2173
                     |                 |                 |                 |                 |                 |
                    GTG  TTC  GCG  GAG  GAC  ATC  CCC  GAC  GTC  GCG  TCG  GCG  AAC  CCC  GTC  CCC  CAG  GCG
                    Val  Phe  Ala  Glu  Asp  Ile  Pro  Asp  Val  Ala  Ser  Ala  Asn  Pro  Val  Pro  Gln  Ala 2182              2191              2200              2209              2218              2231
                     |                 |                 |                 |                 |                 |
                    TGG  TCC  GAC  CTC  TGT  CCG  ACC  TAC  GAC  GCG  CTC  GAC  CCG  AGC  GAC  CAG  TAAATGGCTT
                    Trp  Ser  Asp  Leu  Cys  Pro  Thr  Tyr  Asp  Ala  Leu  Asp  Pro  Ser  Asp  Gln 2241              2251              2261              2271              2281              2291              2301
                     |                 |                 |                 |                 |                 |                 |
                    GCGCCGGTCG ATGATAGGAT ATGGACGGTG AGTTCGCACT TGCAATACGG ACTCTCGCCT CATTATGGTT 2311              2321              2331              2341              2351              2361              2371
                                         |                 |                 |                 |                 |                 |                 |
                    ACACACTCGC TCTGGATCTC TCGCCTGTCG ACAGAACAAA CTTGTATAAT TCGCTTAATG GTTGAAACAA 2381              2391              2401              2411
                                         |                 |                 |                 |
                    ATGGAATATT GGGTACTAT GCACGCATCT CGCTGGGTGA GCTTTCGT
```

FIG. 11

```
         10         20         30         40         50         60         70
GCGGCGCACA AACCGTGGGA GCCAACACAC TCCCGTCCAC TCTCACACTG GCCAGAGATTCG CGGGACCGCC 80         90        100        110        120        130        140
GCCTTTCAGG CCCAAACAGA TCTGGCAGGT TTCGATGGCG CACGCCGCCG TGCCTGCCGG ATTCAATTGT 150        160        170        180        190        200        210
GGGCCAGTCG GGCATCCGGA TGGCTCTACC AGGGCGGTTG ACTGGAAGAG AACACCGAGG TCATGCATTC 220        230        240        250        260        270        280
TGGCCAAGTG CGGCCAAAGG ACCGCTCGCT GGTGCGGATA CTTAAAGGGC GGGCGGGGGA GGCCTGTGTA
```

FIG. 2A

```
         290         300        310        320        330        340        350
CCAAGCTCAA GCTCGCCTTG GGTTCCCAGT CTCCGCCACC CTCCTCTTCC CCCACACAGT CGCTCCATAG 360         369        378        387        396        405
CACCGTCGGC GCC ATG GGT CTG CAG CGA TTC AGC TTC GTC ACC CTC GCG CTC
        MET Gly Leu Gln Arg Phe Ser Phe Val Thr Leu Ala Leu 414        423        432        441        450        459
GTC GCT CGC TCT CTT GCA GCC ATC GGG CCG GTG GCG AGC CTC GTC GCG AAC
Val Ala Arg Ser Leu Ala Ala Ile Gly Pro Val Ala Ser Leu Val Val Ala Asn 468        477        486        495        504        513
GCC CCC GTC TCG CCC GAC GGC TTC CTT CGG GAT GCC ATC GTG GTC AAC GGC GTG
Ala Pro Val Ser Pro Asp Gly Phe Leu Arg Asp Ala Ile Val Val Asn Gly Val
```

*FIG. 2B*

```
         522           531           540                553           563           573
          |             |             |                  |             |             |
GTC CCT TCC CCG CTC ATC ACC GGG AAG AAG GTCGGCGTGT TGTTGTTCGT CCTACTCCTT
Val Pro Ser Pro Leu Ile Thr Gly Lys Lys 583           592           601                619           628
     |             |             |                  |             |
TGCTGACAGC GATCTACAG GGA GAC CGC TTC CAG CTC AAC GTC GTC GAC ACC TTG
                    Gly Asp Arg Phe Gln Leu Asn Val Val Asp Thr Leu 637           646           655                671           681           691
     |             |             |                  |             |             |
ACC AAC CAC AGC ATG CTC AAG TCC ACT AGT ATC GTAAGTGTGA CGATCCGAAT GTGACATCAA
Thr Asn His Ser MET Leu Lys Ser Thr Ser Ile
```

FIG. 2C

```
701            711             721             730             739             748
 |              |               |               |               |               |
TCGGGCTAA TTAACCGCGC ACAG CAC TGG CAC GGC TTC TTC CAG GCA GGC ACC AAC
                          His Trp His Gly Phe Phe Gln Ala Gly Thr Asn 757            766             775             784             793             802
 |              |               |               |               |               |
TGG GCA GAA GGA CCC GCG TTC GTC AAC CAG TGC CCT ATT GCT TCC GGG CAT TCA
Trp Ala Glu Gly Pro Ala Phe Val Asn Gln Cys Pro Ile Ala Ser Gly His Ser 811            820             829                             846             856
 |              |               |                               |               |
TTC CTG TAC GAC TTC CAT GTG CCC GAC CAG GCA G    GTAAGCAGGA TTTCTGGGG
Phe Leu Tyr Asp Phe His Val Pro Asp Gln Ala Gly 866            876             886             896             905             914
 |              |               |               |               |               |
TCCCCGTGTG ATGCAATGTT CTCATGCTCC GACGTGATCG ACAG GG ACG TTC TGG TAC CAC
                                                  Thr Phe Trp Tyr His 923            932             941             950             959             968
 |              |               |               |               |               |
AGT CAT CTG TCT ACG CAG TAC TGT GAC TAC TGT GAC GGG CTG CGG GGG CCG TTC GTC GTG TAC
Ser His Leu Ser Thr Gln Tyr Cys Asp Tyr Cys Asp Gly Leu Arg Gly Pro Phe Val Val Tyr
```

FIG. 2D

```
     977         986         995        1004        1013        1024
      |           |           |           |           |           |
GAC CCC AAG GAC CCG CAC GCC AGC CGT TAC GAT GTT GAC AAT G   GTACGTGCGC
Asp Pro Lys Asp Pro His Ala Ser Arg Tyr Asp Val Asp Asn Glu 1034        1044        1054        1064        1075        1084
             |           |           |           |           |           |
CACGGAGTAT ATCACACAGC ATGGGTTGAC GTCGGGCCAA CAG AG AGC ACG GTC ATC ACG
                                                 Ser Thr Val Ile Thr 1093        1102        1111        1120        1129             1141
     |           |           |           |           |                |
TTG ACC GAC TGG TAC CAC ACC GCT GCC CGG CTC GGT CCC AAG TTC CC   GTAAGCTCGC
Leu Thr Asp Trp Tyr His Thr Ala Ala Arg Leu Gly Pro Lys Phe Pro 1151        1161        1171        1181        1190        1199
            |           |           |           |           |           |
AATGGCTTAG TGTTCACAGG TTCTTTGCTT ATGTTGCTTC GATAG A CTC GGC GCG GAC GCC
                                                    Leu Gly Ala Asp Ala
```

*FIG. 2E*

```
        1208              1217              1226              1235              1244              1253
         |                 |                 |                 |                 |                 |
        ACG CTC ATC AAC GGT CTG GGG CGG TCG GCC TCG ACT CCC ACC GCT GCG CTT GCC
        Thr Leu Ile Asn Gly Leu Gly Arg Ser Ala Ser Thr Pro Thr Ala Ala Leu Ala 1262              1271              1280              1292              1302              1312
         |                 |                 |                 |
        GTG ATC AAC GTC CAG CAC GGA AAG CG  GTGAGCATTC TCTTGTATGC CATTCAATG
        Val Ile Asn Val Gln His Gly Lys Arg 1322              1332              1341              1351              1360              1369
                                              |                 |                 |                 |
        CTTTGTGCTG ACCTATCGGA ACCGCGCAG  C TAC CGC TTC CGT CTC GTT TCG ATC TCG
                                              Tyr Arg Phe Arg Leu Val Ser Ile Ser 1378              1387              1396              1405              1414              1423
         |                 |                 |                 |                 |                 |
        TGT GAC CCG AAC TAC ACG TTC AGC ATC GAC GGG CAC AAC CTG ACC GTC ATC GAG
        Cys Asp Pro Asn Tyr Thr Phe Ser Ile Asp Gly His Asn Leu Thr Val Ile Glu
```

FIG. 2F

```
              1432         1441         1450         1459         1468         1477
               |            |            |            |            |            |
              GTC GAC GGC ATC AAT AGC CAG CCT CTC CTT GTC GAC TCT ATC CAG ATC TTC GCC
              Val Asp Gly Ile Asn Ser Gln Pro Leu Leu Val Asp Ser Ile Gln Ile Phe Ala 1486         1495         1508         1518         1528         1538
               |            |            |            |            |            |
              GCA CAG CGC TAC TCC TTC GTG GTAAGTCCTG GCTTGTCGAT GCTCCAAAGT GGCCTCACTC
              Ala Gln Arg Tyr Ser Phe Val 1548         1559         1568         1577         1586
               |            |            |            |            |
              ATATACTTTC GTTAG TTG AAT GCG AAT CAA ACG GTG GGC AAC TAC TGG GTT CGT
                             Leu Asn Ala Asn Gln Thr Val Gly Asn Tyr Trp Val Arg 1595         1604         1613         1622         1631         1640
               |            |            |            |            |            |
              GCG AAC CCG AAC TTC GGA ACG GTT GGG TTC GCC GGG ATC AAC TCC GCC ATC
              Ala Asn Pro Asn Phe Gly Thr Val Gly Phe Ala Gly Ile Asn Ser Ala Ile 1649         1658         1667         1676         1685         1694
               |            |            |            |            |            |
              TTG CGC TAC CAG GGC GCA CCG GTC GCC GAG CCT ACC ACG ACC CAG ACG CCG TCG
              Leu Arg Tyr Gln Gly Ala Pro Val Ala Glu Pro Thr Thr Thr Gln Thr Pro Ser

FIG.2G
```

```
1703         1712         1721         1730         1739         1748            1761
 |            |            |            |            |            |               |
GTG ATC CCG CTC ATC GAG ACG AAC TTG CAC CCG CTC GCG CGC ATG CCA GTG GTATGTCTCT
Val Ile Pro Leu Ile Glu Thr Asn Leu His Pro Leu Ala Arg MET Pro Val 1771         1781         1791         1801         1811         1821         1882
                                                                            |            |
TTTTCTGATC ATCTGAGTTG CCCGTGTTG ACCGCATTAT GTGTTACTAT CTAG CCT GGC AGC
                                                            Pro Gly Ser 1830         1839         1848         1857         1866                    1882
 |            |            |            |            |                       |
CCG ACA CCC GGG GTC GAC AAG GCG CTC AAC CTC GCG TTT AAC TTC GTAAGTATCT
Pro Thr Pro Gly Gly Val Asp Lys Ala Leu Asn Leu Ala Phe Asn Phe 1892         1902         1912         1922         1931         1940
                                                              |            |
CTACTACTTA GGCTGGAGGC TCGTCGCTGA TCATACGGTG CTTCAG AAC GGC ACC AAC TTC
                                                        Asn Gly Thr Asn Phe
```

FIG. 2H

```
      1949       1958       1967       1976       1985       1994
       |          |          |          |          |          |
TTC ATC AAC AAC GCG ACT TTC ACG CCG ACC GTC CCG GTA CTC CTC CAG ATT
Phe Ile Asn Asn Ala Thr Phe Thr Pro Thr Val Pro Val Leu Leu Gln Ile 2003       2012       2021       2030       2039       2048
       |          |          |          |          |          |
CTG AGC GGT GCG CAG ACC GCA CAA GAC CTG CTC CCC GCA GGC TCT GTC TAC CCG
Leu Ser Gly Ala Gln Thr Ala Gln Asp Leu Leu Pro Ala Gly Ser Val Tyr Pro 2057       2066       2075       2084       2093       2102
       |          |          |          |          |          |
CTC CCG GCC CAC TCC ACC ATC GAG ATC ACG CTG CCC GCG ACC GCC TTG GCC CCG
Leu Pro Ala His Ser Thr Ile Glu Ile Thr Leu Pro Ala Thr Ala Leu Ala Pro 2111       2120       2129          2145       2155       2165
       |          |          |             |          |          |
GGT GCA CCG CAC CCC TTC CAC CTG CAC GGT GTATGTTCCC CTGCCTTCCC TTCTTATCCC
Gly Ala Pro His Pro Phe His Leu His Gly
```

FIG. 2I

```
                                                     2195              2204              2213              2222
2175         2185
CGAACCAGTG CTCACGTCCG TCCCATCTAG CAC GCC TTC GCG GTC GTT CGC AGC GCG
                                    His Ala Phe Ala Val Val Arg Ser Ala 2231              2240              2249              2258              2267              2276
GGG  AGC  ACC  ACG  TAT  AAC  TAC  AAC  GAC  CCG  ATC  TTC  CGC  GAC  GTC  GTG  AGC  ACG
Gly  Ser  Thr  Thr  Tyr  Asn  Tyr  Asn  Asp  Pro  Ile  Phe  Arg  Asp  Val  Val  Ser  Thr 2285              2294              2303              2312              2321              2330
GGC  ACG  CCC  GCC  GCG  GGC  GAC  AAC  GTC  ACG  ATC  CGC  TTC  CAG  ACG  GAC  AAC  CCC
Gly  Thr  Pro  Ala  Ala  Gly  Asp  Asn  Val  Thr  Ile  Arg  Phe  Gln  Thr  Asp  Asn  Pro 2339              2348              2357              2366              2375              2384
GGG  CCG  TGG  TTC  CTC  CAC  TGC  CAC  ATC  GAC  TTC  CAC  CTC  GAC  GCA  GGC  TTC  GCG
Gly  Pro  Trp  Phe  Leu  His  Cys  His  Ile  Asp  Phe  His  Leu  Asp  Ala  Gly  Phe  Ala
```

FIG. 2J

```
          2393        2402        2411        2420        2429        2438
            |           |           |           |           |           |
ATC GTG TTC GCA GAG GAC GTT GCG GAC GTG AAG GCG AAC CCG GTT CCG AAG
Ile Val Phe Ala Glu Asp Val Ala Asp Val Lys Ala Asn Pro Val Pro Lys 2447        2456        2465        2474        2483        2499
            |           |           |           |           |      >    |
GCG TGG TCG GAC CTG TGC CCG ATC TAC GAC GGG CTG AGC GAG GCT AAC CAG TGAGCGGAGG
Ala Trp Ser Asp Leu Cys Pro Ile Tyr Asp Gly Leu Ser Glu Ala Asn Gln 2509        2519        2529        2539        2549        2559        2569
       |           |           |           |           |           |           |
GCGTGGTGTT GAGCGTAAAG CTCGGGCGTC GACCTGGGGG GTTGAAGGTG TTCTGATTGA AATGGTCTTT 2579        2589        2599        2609        2619        2629        2639
       |           |           |           |           |           |           |
GGGTTTATTT GTTGTTATTC TAACTCGGTT CTCTACGCAA GGACCGAGGA TTGTATAGGA TGAAGTAACT 2649        2659        2669        2679        2689
       |           |           |           |           |
TTCCTAATGT ATTATGATAT CAATTGACGG AGGCATGGAC TGCGAAGTGT
```

FIG. 2K

```
  10         20         30         40         50         60         70
TTTCCGACT  AAACCAATCT CAGNCCGCTT CCTCCTAGGG AACCGAGCGA TGTGGCGGCC CTCTCTATCC 80         90        100        110        120        130        140
AAGCTGTCCA TAAGAAGACG TTCAAATGCC GCAGCAAGCG AGGAAATAAG CATCTAACAG TGTTTTTCCC 150        160        170        180        190        200        210
ATAGTCGCAT TTGCGCCGCC TGTCGGACCG ACGCCCCTAG AGCGCTTTGG GAAACGTCGC AAGTGGCGGG 220        230        240        250        260        270        280
TGTTATTCGT GTAGACGAGA CGGTATTTGT CTCATCATTC CCGTGCTTCA GGTTGACACA GCCCAAAGT
```

FIG. 3A

```
                                                                          350
                                                           340
                                            330
                             320
              310
300
290
      CTATGTACGG CCCTTCACAT TCCCTGACAC ATTGACGCAA CCCTCGGTGC GCCTCCGACA GTGCCTCGGT 420
                                                           410
                                            400
                             390
              380
370
360
      TGTAGTATCG GGACGCCCTA GGATGCAAGA TTGGAAGTCA CCAAGGCCCG AAGGTATAA AATACCGAGA 480
                                            470
                             460
              450
440
430
      GGTCCTACCA CTTCTGCATC TCCAGTCGCA GAGTTCCTCT CCCTTGCCAG CCACAGCTCG AG
```

```
                                                               536
                                                  527
                                       518
                            509
              500
491
>
ATG TCC TTC TCT AGC CTT CGC CGT GCC CTG GTC TTC CTG GGT GCT TGC AGC AGT
MET Ser Phe Ser Ser Leu Arg Arg Ala Leu Val Phe Leu Gly Ala Cys Ser Ser 590
                                                  581
                                       572
                            563
              554
545
GCC TCC ATC GGC CCA GTC ACT GAG CTC GAC ATC GTT AAC AAG GTC ATC
Ala Ser Ile Gly Pro Val Thr Glu Leu Asp Ile Val Asn Lys Val Ile
```

GCG CTG
Ala Leu

FIG. 3B

```
     599            608            617            626            635            644
      |              |              |              |              |              |
GCC CCG GAT GGC GTC GCT CGT GAT ACA GTC CTC GCC GGG GGC ACG TTC CCG GGC
Ala Pro Asp Gly Val Ala Arg Asp Thr Val Leu Ala Gly Gly Thr Phe Pro Gly 653            662            675            685            695            705
      |              |              |              |              |              |
CCA CTC ATC ACA GGA AAG AAG GTATGCTAAG TAGTCCCGCC CCCATCATCC TGTGGCTGAC
Pro Leu Ile Thr Gly Lys Lys 715            726            735            744            753
      |              |              |              |              |
GTTCGACGCC GCCAG GGT GAC AAC TTC CGC ATC AAC GTC GTC GAC AAG TTG GTT
            Gly Asp Asn Phe Arg Ile Asn Val Val Asp Lys Leu Val 762            771            780            789            799       809            819
      |              |              |              |              |         |              |
AAC CAG ACT ATG CTG ACA TCC ACC ATT GTATGTCACT AGCTCTCGCT ATCTCGAGAC
Asn Gln Thr MET Leu Thr Ser Thr Ile
```

FIG.3C

```
                829        839                   848        857        866        875
CCGCTGACCG ACAACATTG CCGTAG CAC TGG CAC GGG ATG TTC CAG CAT ACG ACG
                              His Trp His Gly MET Phe Gln His Thr Thr 884        893        902        911        920        929
AAC TGG GCG GAT GGT CCC GCC TTT GTG ACT CAA TGC CCT ATC ACC ACT GGT GAT
Asn Trp Ala Asp Gly Pro Ala Phe Val Thr Gln Cys Pro Ile Thr Thr Gly Asp 938        947        956        965           976        986
GAT TTC CTG TAC AAC TTC CGC GTG CCC GAC CAG ACA G   GTACGCAAAG GGCAGCATGC
Asp Phe Leu Tyr Asn Phe Arg Val Pro Asp Gln Thr Gly 996        1006       1016       1026       1035       1044
GTACTCAAAG ACATCTCTAA GCATTGCTA CCTAG GA ACG TAC TGG TAC CAT AGC CAT
                                        Thr Tyr Trp Tyr His Ser His
```

FIG. 3D

```
        1053              1062              1071              1080              1089              1098
          |                 |                 |                 |                 |                 |
CTG GCC TTG CAG TAC TGT GAT GGG CTT CGC GGC CCC CTG GTG ATT TAC GAT CCC
Leu Ala Leu Gln Tyr Cys Asp Gly Leu Arg Gly Pro Leu Val Ile Tyr Asp Pro 1107              1116              1125              1134              1145       1155
          |                 |                 |                 |                 |          |
CAT GAT CCG CAG GCA TAC CTG TAT GAC GTC GAT GAC G    GTACGCAGCA CAGTTCCCT
His Asp Pro Gln Ala Tyr Leu Tyr Asp Val Asp Asp Glu 1165              1175              1185              1198              1207
          |                 |                 |                 |                 |
AAAACGGTTA ACTTCTAATT CTGTAAATAT CTTCATAG AG AGC ACC GTT ATC ACT CTG
                                             Ser Thr Val Ile Thr Leu 1216              1225              1234              1243              1252       1267
          |                 |                 |                 |                 |          |
GCA GAC TGG TAC CAT ACC CCG GCG CCT CTG CCG CCT GCC GC  GTACGCCTCC
Ala Asp Trp Tyr His Thr Pro Ala Pro Leu Pro Pro Ala Ala
```

```
            1277        1287        1297        1307        1317              1328
ACACATCTGC ACAGGTTCC GTATCTCATA CCCTTAAAGT TTATCGGACA G C ACT TTG ATT
                                                           Thr Leu Ile 1337        1346        1355        1364        1373              1382
AAT GGC CTG GGT CGC TGG CCT GGC AAC CCC ACC GCC GAC CTA GCC GTC ATC GAA
Asn Gly Leu Gly Arg Trp Pro Gly Asn Pro Thr Ala Asp Leu Ala Val Ile Glu 1391        1409        1419        1429        1439              1449
GTC CAG CAC GGA AAG CG  GTATGTCATA GCTCGGTTAT CTATTCATAC TCGGGCCCTC GAAGCTAAAA
Val Gln His Gly Lys Arg 1459        1470        1479        1488        1497
CCTTGTTCCA G C TAC CGG TTC CGA CTG GTC AGC ACC TCA TGC GAC CCC AAC TAC
              Tyr Arg Phe Arg Leu Val Ser Thr Ser Cys Asp Pro Asn Tyr
```

```
1506            1515           1524           1533           1542           1551
 |               |              |              |              |              |
AAC TTC ACT ATC GAT GGC CAC ACC ATG ACA ATC ATC GAG GCG GAT GGG CAG AAC
Asn Phe Thr Ile Asp Gly His Thr MET Thr Ile Ile Glu Ala Asp Gly Gln Asn 1560            1569           1578           1587           1596           1605
 |               |              |              |              |              |
ACC CAG CCA CAC CAA GTC GAC GGA CTT CAG ATC CAG ATC TTC GCG GCA CAG CGG TAC TCC
Thr Gln Pro His Gln Val Asp Gly Leu Gln Ile Gln Ile Phe Ala Ala Gln Arg Tyr Ser 1614          1627          1637          1647          1657          1667
         |             |             |             |             |             |
TTC GTT GTATGTTTC CGCATTCGG GAAAAGGAAT TGCGCTGACA GCTCGAGTGT GGGTAG
Phe Val 1676            1685           1694           1703           1712           1721
 |               |              |              |              |              |
CTT AAC GCT AAC CAA GCG GTC AAC AAC TAC TGG ATC CGT GCG AAC CCT AAC CGT
Leu Asn Ala Asn Gln Ala Val Asn Asn Tyr Trp Ile Arg Ala Asn Pro Asn Arg 1730            1739           1748           1757           1766           1775
 |               |              |              |              |              |
GCT AAC ACT ACG GGC TTC GCC AAC GGC ATC GCC ATC TCC GCC ATC CTG CGC TAC AAG
Ala Asn Thr Thr Gly Phe Ala Asn Gly Ile Ala Ile Ser Ala Ile Leu Arg Tyr Lys
```

*FIG. 3G*

```
1784         1793         1802         1811         1820         1829
 |            |            |            |            |            |
GGG GCG CCG ATT AAG GAG CCT ACG AAC CAG ACT ACC ATC CGG AAC TTT TTG
Gly Ala Pro Ile Lys Glu Pro Thr Asn Gln Thr Thr Ile Arg Asn Phe Leu 1838         1847         1856         1865         1874         1884    1894
 |            |            |            |            |            |      |
TGG GAG ACG GAC TTG CAC CCG CTC ACT GAC CCA CGT GCA GTAAGTTCTA CACAGTCACC
Trp Glu Thr Asp Leu His Pro Leu Thr Asp Pro Arg Ala 1904         1914         1924         1933         1942        1951
                        |            |            |            |            |           |
AACGGTGAGC TGTTGTCTGA TTGCACTGTG TTATAG CCT GGC CTT CCT TTC AAG GGG GGC
                                        Pro Gly Leu Pro Phe Lys Gly Gly 1960         1969         1978         1987         1997         2007        2017
 |            |            |            |            |            |           |
GTT GAC CAC GCT TTG AAC CTC AAC CTC ACT TTC GTACGTAGCG CCTCAGATAT CGAGTAGTCT
Val Asp His Ala Leu Asn Leu Asn Leu Thr Phe
```

*FIG. 3H*

```
                                                                              2073
                         2037        2046        2055        2064        |
     2027                 |           |           |           |          TTC
      |                  GGA         TCG         TTC         AAC    GAT  GCG  CCT
ATCTCCTGAC CGATTGACAG    AAT         GAG         ATC         GAT    Asn  Ala  Pro Phe
                         Asn   Gly   Ser   Glu   Phe   Phe   Ile    Asp

2127
                                                                               |
         2082        2091        2100        2109        2118
          |           |           |           |           |
         GTC   CCT   CCG   ACT   GTC   CCG   CTA   CTG   CAG   ATC   CTG   AAC   GGA   ACG   CTC   GAC   GCG
         Val   Pro   Pro   Thr   Val   Pro   Val   Leu   Gln   Ile   Leu   Asn   Gly   Thr   Leu   Asp   Ala 2181
         2136        2145        2154        2163        2172                  |
          |           |           |           |           |
         AAC   GAC   CTC   CTG   CCG   CCC   GGC   AGC   GTC   TAC   AAC   CTT   CCT   CCG   GAC   TCC   ACC   ATC
         Asn   Asp   Leu   Leu   Pro   Pro   Gly   Ser   Val   Tyr   Asn   Leu   Pro   Pro   Asp   Ser   Thr   Ile 2235
         2190        2199        2208        2217        2226                  |
          |           |           |           |           |
         GAG   CTG   TCC   ATT   CCC   GGA   GGT   GTG   ACG   GGT   GGC   CCG   CAC   CCA   TTC   CAT   TTG   CAC
         Glu   Leu   Ser   Ile   Pro   Gly   Gly   Val   Thr   Gly   Gly   Pro   His   Pro   Phe   His   Leu   His 2297
         2248        2258        2268        2278        2288  |
          |           |           |           |           |
         GGG   GTAATAATCT CTCTTTATAC TTTGGTCTCC CGATGCTGAC TTTCACTGCT CATCTTCAG
         Gly
```

FIG. 31

```
     2306          2315          2324          2333          2342          2351
      |             |             |             |             |             |
     CAC GCT TTC TCC GTC GTG CGT AGC GCC GGC AGC ACC GAA TAC AAC TAC GCG AAC
     His Ala Phe Ser Val Val Arg Ser Ala Gly Ser Thr Glu Tyr Asn Tyr Ala Asn 2360          2369          2378          2387          2396          2405
           |             |             |             |             |             |
          CCG GTG AAG CGC GAC ACG GTC AGC ATT GGT CTT GCG GGC GAC AAC GTC ACC GTG
          Pro Val Lys Arg Asp Thr Val Ser Ile Gly Leu Ala Gly Asp Asn Val Thr Val 2414          2424          2434          2444          2454          2464
                |             |             |             |             |             |
               CGC TTC GTG GTATGTTTTA CAGCCTCTCT ATCTCCGTGG GCGGTTCGGAA GTTGACTGGG CGCGTAG
               Arg Phe Val 2474          2483          2492          2501          2510          2519
                     |             |             |             |             |             |
                    ACC GAC AAC CCC GGC CCG TGG TTC CTC CAC TGT CAC ATC GAC TTC CAT TTG CAA
                    Thr Asp Asn Pro Gly Pro Trp Phe Leu His Cys His Ile Asp Phe His Leu Gln
```

FIG.3J

```
2528        2537            2546            2555            2564            2573
  |           |               |               |               |               |
GCA  GGC CTC GCC ATC  GTG TTC GCG GAG  GAC GCG CAG  ACG AAG CTT  GTG AAC
Ala  Gly Leu Ala Ile  Val Phe Ala Glu  Asp Ala Gln  Thr Lys Leu  Val Asn 2582                            2599            2609            2619            2629            2639
              |                               |               |               |               |               |
CCC  GTC CCT G   GTACGTCTTC TGGATGCATG CGCTCCGCAC AGTGACTCAT CTTTTGCAAC
Pro  Val Pro Glu 2649            2658            2667            2676            2685
       |               |               |               |               |
AG  AG  GAC TGG AAC AAG  CTG TGC CCC ACC  TTC GAT AAG GCG  ATG AAC ATC ACG
    Asp Trp Asn Lys  Leu Cys Pro Thr  Phe Asp Lys Ala  MET Asn Ile Thr 2694            2704            2714            2724            2734            2744            2754
  |               |               |               |               |               |               |
 -->
GTT TGAGCGATGC GTGGCGCTCA TGTCATTTT CTTGGAATCT TTGCATAGGG CTGCAGCACG
Val 2764            2774            2784            2794            2804            2814            2824
  |               |               |               |               |               |               |
CTGGATACTC TTTCCCTTAG CAGGATATTA TTTAATGACC CCTGGCGTTTA GTGCTTAGTT AGCTTTACTA
```

*FIG. 3K*

```
2834       2844       2854       2864       2874       2884       2894
CTGGTTGTAA TGTACGCAGC ATGCGTAATT CGGATAATGC TATCAATGTG TATATTATGA CACGCGTCAT 2904       2914       2924       2934       2944       2954       2964
GCGCGATGCT TGAGTTGCAA GGTCGGTTTC CGATGCTCGA CATAAACGTT TCACTTACAT ACACATTGGG 2974       2984       2994       3004       3014       3024       3034
TCTAGAACTG GATCTATCCA TGTATACAAA AACTCCTCAT ACAGCTGACT GGGGCGCTCT AGAGCATGGG 3044       3054       3064       3074       3084       3094       3104
TCCGATTGAT CAGATGTCGC GAACACGAGC CTCCTGAGCT CGAGGACTCT GAGAAGCGGC GGTGCGTTCT
```

FIG. 3L

```
        10         20         30         40         50         60         70
GCGCGTTGGC CGATTCATTA ATGCAGCTGG CACGACAGGT TTCCCGACTG GAAAGCGGGC AGTGAGCGCA 80         90        100        110        120        130        140
ACGCAATTAA TGTGAGTTAG CTCACTCATT AGGCACCCCA GGCTTTACAC TTTATGCTTC CGGCTCGTAT 150        160        170        180        190        200        210
GTTGTGTGGA ATTGTGAGCG GATAACAATT TCACACAGGA AACAGCTATG ACATGATTAC GAATTCCGAT 220        230        240        250        260        270        280
CGGCTTGCCC TCATTCCTCC ATGTTCCCCC GACCGAGCGG GCGGTCAAT GGCCCGTTTG CGAACACATA
```

```
               290        300        310        320        330        340        350
        TGCAGGATAA ACAGTGCGAA ATATCAATGT GGCGGCGACA CAACCTCGCC GGCCGACACT CGACGCTGTT 360        370        380        390        400        410        420
        GATCATGATC ATGTCTTGTG AGCATTCTAT ACGCAGCCTT GGAAATCTCA GGCGAATTTG TCTGAATTGC 430        440        450        460        470        480        490
        GCTGGGAGGC TGGCAGGCA  GATCGGTGTG TCGGTGCAGT AGCCGACGCA GCACCTGGCG GAAGCCGACA 500        510        520        530        540        550        560
        TCTCGGGTAC GACTTGATCT CCGCCAGATC ACTGCGGTTC CGCCATCGGC CGGGGGCCC  ATTCTGTGTG 570        580        590        600        610        620        630
        TGCGCTGTAG CACTCTGCAT TCAGGCTCAA CGTATCCATG CTAGAGGACC GTCCAGCTGT TGGCGCACGA
```

```
                                640         650         660         670         680         690         700
TTCGGCCAGA AAGCTGTACA GGCAGATATA AGGATGTCCG TCCGTCAGAG ACTCGTCACT CACAAGCCTC 710         720         730         740         750         760         770
TTTTCCTCTT CGCCTTTCCA GCCTCTTCCA ACGCCTGCCA TCGTCCTCTT AGTTCGCTCG TCCATTCTTT
```

```
              780             790             799     808         817         826
               >
CTGGGTAGTT AATC ATG GGC AGG TTC TCA TCT CTC TGC GCG CTC ACC GCC GTC ATC
               MET Gly Arg Phe Ser Ser Leu Cys Ala Leu Thr Ala Val Ile 835         844         853         862         871         880
CAC TCT TTT GGT CGT GTC TCC GCC GCT ATC GGG CCT GTG ACC GAC CTC ACC ATC
His Ser Phe Gly Arg Val Ser Ala Ala Ile Gly Pro Val Thr Asp Leu Thr Ile
```

FIG. 4C

```
        889            898            907            916            925            934
         |              |              |              |              |              |
TCC AAT GGG GAC GTT TCT CCC GAC GGC TTC ACT CGT GCC GCA GTG CTT GCA AAC
Ser Asn Gly Asp Val Ser Pro Asp Gly Phe Thr Arg Ala Ala Val Leu Ala Asn 943            952            961            970            980            990
         |              |              |              |              |              |
GGC GTC TTC CCG GGT CCT CTT ATC ACG GGA AAC AAG GTACGTGGCA TGCGTTCAGT
Gly Val Phe Pro Gly Pro Leu Ile Thr Gly Asn Lys 1000           1010           1020           1029           1038           1047
         |              |              |              |              |              |
CTACACCCTA CAAGCTTCT AACTCTTTTA CCACAG GGC GAC AAC TTC CAG ATC AAT GTT
                                      Gly Asp Asn Phe Gln Ile Asn Val 1056           1065           1074           1083           1092           1105
         |              |              |              |              |              |
ATC GAC AAC CTC TCT AAC GAG ACG ATG TTG AAG TCG ACC TCC ATC GTATGTGCTT
Ile Asp Asn Leu Ser Asn Glu Thr MET Leu Lys Ser Thr Ser Ile
```

*FIG. 4D*

```
                                                                      1115           1125           1135           1145           1156           1165
                                                                       |              |              |              |              |              |
                                                                      CTACTGCTTC  TTAGTCTTGG  CAATGGCTCA  AGTCTCCCTC  CGCAG CAT TGG CAC GGC TTC
                                                                                                                           His Trp His Gly Phe 1174           1183           1192           1201           1210           1219
 |              |              |              |              |              |
TTC CAG AAG GGT ACT AAC TGG GCT GAT GGA GCT GCC TTC AAC CAG TGC CCT
Phe Gln Lys Gly Thr Asn Trp Ala Asp Gly Ala Ala Phe Asn Gln Cys Pro 1228           1237           1246           1255           1264           |
 |              |              |              |              |
ATC GCG ACG GGG AAC TCT TTC CTT TAC GAC TTC ACC GCG ACG GAC CAA GCA G
Ile Ala Thr Gly Asn Ser Phe Leu Tyr Asp Phe Thr Ala Thr Asp Gln Ala Gly 1281           1291           1301           1311           1321           1331
 |              |              |              |              |              |
GTCAGTGCCT  GTGGCGCTTA  TGTTTCCCG  TAATCAGCAG  CTAACACTCC  GCACCCACAG  GC
```

*FIG. 4E*

```
        1342         1351         1360         1369         1378         1387
          |            |            |            |            |            |
ACC TTC TGG TAC CAC AGT CAC TTG TCT ACG CAG TAC TGC GAT GGT TTG CGG GGC
Thr Phe Trp Tyr His Ser His Leu Ser Thr Gln Tyr Cys Asp Gly Leu Arg Gly 1396         1405         1414         1423         1432         1441
          |            |            |            |            |            |
CCG ATG GTC GTA TAC GAC CCG AGT GAC CCG CAT GCG GAC CTT TAC GAC GTC GAC
Pro MET Val Val Tyr Asp Pro Ser Asp Pro His Ala Asp Leu Tyr Asp Val Asp 1450         1459         1468         1477         1486         1495
          |            |            |            |            |            |
GAC GAG ACC ACG ATC ATC ACG CTC TCT GAT TGG TAT CAC ACC GCT GCT TCG CTC
Asp Glu Thr Thr Ile Ile Thr Leu Ser Asp Trp Tyr His Thr Ala Ala Ser Leu 1504         1519         1529         1539         1549         1559
          |            |            |            |            |            |
GGT GCT GCC TTC CC GTAAGTTTAC CCCAGCGCAC GGAGTTAAGA CCGGATCTAA CTGTAATACG
Gly Ala Ala Phe Pro
```

FIG. 4F

```
                          1568                    1577                   1586                         1604        1614
                           |                       |                      |                             |           |
                       TTCAG G ATT GGC TCG GAC TCT ACC CTG ATT AAC GG    GTTGGCCGCT TCGCGGGTGG
                             Ile Gly Ser Asp Ser Thr Leu Ile Asn Gly 1624    1633       1642    1651                                    1669
                           |        |          |       |                                       |
                       TGACAG C ACT GAC CTT GCG GTT ATC ACT GTC GAG CAG GGC AAG CG    GTTAGTGATA
                               Thr Asp Leu Ala Val Ile Thr Val Glu Gln Gly Lys Arg 1679       1689      1699        1709                 1719              1728
                           |          |          |           |                    |                 |
                       CCCTCTACAG TTGACACTGT GCCATTGCTG ACAGTACTCT CAG C TAC CGT ATG CGT CTT
                                                                      Tyr Arg MET Arg Leu 1737      1746      1755       1764              1773              1782
                           |         |          |          |                 |                 |
                       CTC TCG CTG TCT TGC GAC CCC AAC TAT GTC TTC TCC ATT GAC GGC CAC AAC ATG
                       Leu Ser Leu Ser Cys Asp Pro Asn Tyr Val Phe Ser Ile Asp Gly His Asn MET
```

FIG.4G

```
      1791       1800       1809       1818       1827      1836
       |          |          |          |          |         |
ACC ATC ATC GAG GCC GAC GCC GTC AAC CAC GAG CCC CTC ACG GTT GAC TCC ATC
Thr Ile Ile Glu Ala Asp Ala Val Asn His Glu Pro Leu Thr Val Asp Ser Ile 1845       1854       1863       1872       1881      1890      1899
       |          |          |          |          |         |         |
CAG ATC TAC GCC GGC CAA CGT TAC TCC TTC GTC GTACGTATTC CGAACAGCCA TGATCACGCC
Gln Ile Tyr Ala Gly Gln Arg Tyr Ser Phe Val

AAGCCCGATG CTAACGCGCC TACCCTCAG CTT ACC GCT GAC CAG GAC ATC GAC AAC TAC
                                Leu Thr Ala Asp Gln Asp Ile Asp Asn Tyr
      1909       1919       1928       1937       1946      1955

1964       1973       1982       1991       2000      2009
       |          |          |          |          |         |
TTC ATC CGT GCC CTG CCC AGC GCC GGT ACC ACC TCG TTC GAC GGC ATC AAC
Phe Ile Arg Ala Leu Pro Ser Ala Gly Thr Thr Ser Phe Asp Gly Ile Asn
```

FIG. 4H

```
         2018           2027           2036           2045           2054           2063
          |              |              |              |              |              |
         TCG GCT ATC CTG CGC TAC TCT GGT GCC TCC GAG GTT GAC CCG ACG ACC ACG GAG
         Ser Ala Ile Leu Arg Tyr Ser Gly Ala Ser Glu Val Asp Pro Thr Thr Thr Glu 2072           2081           2090           2099           2108           2117
          |              |              |              |              |              |
         ACC ACG AGC GTC CTC CCC CTC GAC GAG GCG AAC CTC GTG CCC CTT GAC AGC CCC
         Thr Thr Ser Val Leu Pro Leu Asp Glu Ala Asn Leu Val Pro Leu Asp Ser Pro 2126           2136           2146           2156           2166           2176
          |              |              |              |              |              |
         GCT GCT GTACGTCGTA TTCTGGCTT GCAAGGATCG CACATACTAA CATGCTCTG TAG CCC
         Ala Ala                                                              Pro 2185           2194           2203           2212           2221           2230
          |              |              |              |              |              |
         GGT GAC CCC AAC ATT GGC GGT GTC GAC TAC GCG CTG AAC TTG GAC TTC AAC TTC
         Gly Asp Pro Asn Ile Gly Gly Val Asp Tyr Ala Leu Asn Leu Asp Phe Asn Phe
```

FIG. 41

```
2239              2248        2257        2266        2275        2284
 |                 |           |           |           |           |
GAT GGC ACC AAC TTC TTC ATC AAC GAC GTC TCC TTC GTG TCC CCC ACG GTC CCT
Asp Gly Thr Asn Phe Phe Ile Asn Asp Val Ser Phe Val Ser Pro Thr Val Pro 2293              2302        2311        2320        2329        2338
 |                 |           |           |           |           |
GTC CTC CTC CAG ATT CTT AGC GGC ACC ACC TCC GCG GCC GAC CTT CTC CCC AGC
Val Leu Leu Gln Ile Leu Ser Gly Thr Thr Ser Ala Ala Asp Leu Leu Pro Ser 2347              2356        2365        2374        2383        2392
 |                 |           |           |           |           |
GGT AGT CTC TTC GCG GTC CCG TCC AAC TCG ACG ATC GAG ATC TCG TTC CCC ATC
Gly Ser Leu Phe Ala Val Pro Ser Asn Ser Thr Ile Glu Ile Ser Phe Pro Ile 2401              2410        2419        2428        2437        2446        2456
 |                 |           |           |           |           |           |
ACC GCG ACG AAC GCT CCC GGC GCG CCG CAT CCC TTC CAC TTG CAC GGT GTACGTGTCC
Thr Ala Thr Asn Ala Pro Gly Ala Pro His Pro Phe His Leu His Gly
```

*FIG. 4J*

```
                              2466         2476         2486         2496         2506         2515
                               |            |            |            |            |            |
                        CATCTCATAT GCTACGGAGC TCCACGCTGA CCGCCCTATA G CAC ACC TTC TCT ATC GTT
                                                                      His Thr Phe Ser Ile Val 2524         2533         2542         2551         2560         2569
       |            |            |            |            |            |
 CGT ACC GCC GGC AGC ACG GAT ACG AAC TTC GTC AAC CCC GTC CGC CGC GAC GTC
 Arg Thr Ala Gly Ser Thr Asp Thr Asn Phe Val Asn Pro Val Arg Arg Asp Val 2578         2587         2596         2605         2614         2624
       |            |            |            |            |            |
 GTG AAC ACC GGT ACC GTC GGC GAC AAC GTC ACC ATC CGC TTC ACG GTACGCAGCA
 Val Asn Thr Gly Thr Val Gly Asp Asn Val Thr Ile Arg Phe Thr
```

FIG. 4K

```
      2634       2644       2654       2664       2673       2682
                                                    |          |
CTCTCCTAAC ATTCCCACTG CGGGATCACT GACTCCCTGC CCACAG ACT GAC AAC CCC GGC
                                                    Thr Asp Asn Pro Gly 2691       2700       2709       2718       2727       2736
  |          |          |          |          |          |
CCC TGG TTC CTC CAC TGC CAC ATC GAC TTC CAC TTG GAG GCC GGT TTC GCC ATC
Pro Trp Phe Leu His Cys His Ile Asp Phe His Leu Glu Ala Gly Phe Ala Ile 2745       2754       2763       2772       2781
  |          |          |          |          |          ─ 2798
GTC TTC AGC GAG GAC ACC GCC GAC GTC TCG AAC ACG ACC ACG CCC TCG A   GTACGTTGTG
Val Phe Ser Glu Asp Thr Ala Asp Val Ser Asn Thr Thr Thr Pro Ser Thr 2808       2818       2828       2838       2850       2859
                                                    |          |
CTCCCGTGCC CATCTCCGCG CGCCTGACTA ACGAGCACCC CTTACAG CT GCT TGG GAA GAT
                                                    Ala Trp Glu Asp
```

FIG. 4L

```
        2868         2877         2886        2895                         2908         2918
                                                            ˅
          |            |            |           |            |             |            |
       CTG TGC CCC ACG TAC AAC GCT CTT GAC TCA TCC GAC CTC TAATCGGTTC AAAGGGTCGC
       Leu Cys Pro Thr Tyr Asn Ala Leu Asp Ser Ser Asp Leu 2928         2938         2948         2958         2968         2978         2988

TCGCTACCTT AGTAGGTAGA CTTATGCACC GGACATTATC TACAATGGAC TTTAATTTGG GTTAACGGCC 2998         3008         3018         3028         3038         3048         3058

GTTATACATA CGGCCACGTA GTATAAAGGT TCTCTCGATT GGTCGGACCT ACAGACTGCA ATTTTCGTGA 3068         3078         3088         3098

CCTATCAACT GTATATTGAA GCACGACAGT GAATGGAAAT AGAGACA
```

FIG. 4M

```
        10          20          30          40          50          60          70
CTCATAACTC  TTCGCTTCTA  GCATGGGGGC  TGCGCACACC  TGACAGACCC  TTCGGGAGGC  GAACTCGAAT 80          90         100         110         120         130         140
GCAGCGTACT  CTATCNCACC  TCCAGGAAAG  GTAGGGATGG  ACNCCGTGCA  CCAACAACTG  TCTCTCCACC 150         160         170         180         190         200         210
AGCAACCATC  CCTTGGATAT  GTCTCCACAC  ACCCGGTGTC  TACAAGCGGG  GATCTGTGCT  GGTGAAGTGC 220         230         240         250         260         270         280
TGTCTCCGGA  GCGGGCGGCGG  CGAGCGACCA  GAACCCGAAC  CAGTGCTAGT  GCCCGACACC  CGGCGAGACAA 290         300         310         320         330         340         350
TTGTGCAGGG  TGAGTTATAT  TCTTCGTGAG  ACGGGCCTGC  GCGTCGGCAC  TGAAAGCGTC  GCAGTTAGGT
```

FIG.5A

```
                                                          360         370         380         390         400         410         420
                                                GATGCAGCGG TCCGCGCTAT TTTTGACGTC TGGCAGCTAT CCTAAGCCGC GCCTCCATAC ACCCCAGGCG 430         440         450         460         470         480         490
                                                CTCTCGTTTG CTATAGGTAT AAATCCCTCA GCTTCAGAGC GTCGATCCTC ATCCCACACG ACACCCGTTT 500         510         520         530         540                 550
                                                                                                                        >
                                                CAGTCTTCTC GTAGCGCATT CCCTAGCCGC CCAGCCTCCG CTTTCGTTTT CAAC ATG GGC AAG
                                                                                                              MET Gly Lys 559          568          577          586          595                                                       604
|TAT |CAC |TCT |TTT |GTG |AAC |GTC |GCC |CTT |TCT |AGT |CTT |TCT |TTG |AGC |GGT |CGT |GTG
 Tyr  His  Ser  Phe  Val  Asn  Val  Ala  Leu  Ser  Ser  Leu  Ser  Leu  Ser  Gly  Arg  Val 613          622          631          640          649                                                       658
|TTC |GGC |GCC |ATT |GGG |CCC |GTC |ACC |GAC |TTG |ACT |ATC |TCT |AAC |GCC |GAT |GTT |ACG
 Phe  Gly  Ala  Ile  Gly  Pro  Val  Thr  Asp  Leu  Thr  Ile  Ser  Asn  Ala  Asp  Val  Thr
```

FIG. 5B

```
     667        676        685        694        703        712
 CCT GAC GGC ATT ACT CGT GCT GTC CTC GCG GGC GGC GTT TTC CCC GGG CCC
 Pro Asp Gly Ile Thr Arg Ala Val Leu Ala Gly Gly Val Phe Pro Gly Pro 721        730        743        753        763        773   783
 CTC ATT ACC GGC AAC AAG GTGAGCCCGCG AAACCTTCTA CTAGCGCGCT CGTACGGTGC ACCGTTACTG
 Leu Ile Thr Gly Asn Lys 793        803        814        823        832    841
 AAGCCACACT TTGCGCTGTC AACAG GGG GAT GAA TTC CAG ATC AAT GTC ATC GAC AAC
                              Gly Asp Glu Phe Gln Ile Asn Val Ile Asp Asn 850        859        868        877        887        897
 CTG ACC AAC GAG ACC ATG TTG AAG TCG ACC ACA ATC GTAAGGTGCT TGCTCCCATA
 Leu Thr Asn Glu Thr MET Leu Lys Ser Thr Thr Ile 907        917        927        938        947     956
 ATTAAGCCCG TCGCTGACTC GAAGTTTATC TGTAG CAC TGG CAT GGT ATC TTC CAG GCC
                                        His Trp His Gly Ile Phe Gln Ala
```

FIG. 5C

```
                965           974           983           992          1001          1010
     GGC ACC AAC TGG GCA GAC GGC GCG GCC TTC GTG AAC CAG TGC CCT ATC GCC ACG
     Gly Thr Asn Trp Ala Asp Gly Ala Ala Phe Val Asn Gln Cys Pro Ile Ala Thr 1019          1028          1037          1046                    1063
     GGA AAC TCG TTC TTG TAC GAC TTC ACC GTT CCT GAT CAA GCC G    GTACGTTTAT
     Gly Asn Ser Phe Leu Tyr Asp Phe Thr Val Pro Asp Gln Ala Gly 1073          1083          1093          1103          1112          1121
     ACACTTCCCT TCTGCGGCA TACTCTGACG CGCCGCTGGA TCAG GC ACC TTC TGG TAC CAC
                                                       Thr Phe Trp Tyr His 1130          1139          1148          1157          1166          1175
     AGC CAC CTG TCC ACC CAG TAC TGT GAC GGC CTG CGC GGT CCT CTT GTG GTC TAC
     Ser His Leu Ser Thr Gln Tyr Cys Asp Gly Leu Arg Gly Pro Leu Val Val Tyr 1184          1193          1202          1211          1220          1231
     GAC CCC GAT CCC AAC GCG TCT CTT TAC GAC GTC GAT GAC G    GTAAGCAGGC
     Asp Pro Asp Pro Asn Ala Ser Leu Tyr Asp Val Asp Asp
```

FIG. 5D

```
                                              1241        1251        1261        1271        1281        1290
                                    TACTGTGTGGA CTTGTATGGA TGTATCTCAC GCTCCCCTAC AG AT ACT ACG GTT ATT ACG
                                                                                        Thr Thr Val Ile Thr 1299        1308        1317        1326        1335              1347
CTT GCG GAC TGG TAC CAC ACT GCG GCG AAG CTG GGC CCT GCC TTC CC  GTGAGTCTAC
Leu Ala Asp Trp Tyr His Thr Ala Ala Lys Leu Gly Pro Ala Phe Pro 1357        1367        1377        1387        1397        1408
TCTTCCTCGT GTGTTAACAT AGGTGACGGC CGCTGATACG AGAGCTACCA G C GCG GGT CCG
                                                          Ala Gly Pro 1417        1426        1435        1444        1453        1462
GAT AGC GTC TTG ATC AAT GGT CTT GGT CGG TTC TCC GGC GAT GGT GGA GGA GCG
Asp Ser Val Leu Ile Asn Gly Leu Gly Arg Phe Ser Gly Asp Gly Gly Gly Ala 1471        1480        1489        1498        1510        1520
ACA AAC CTC ACC GTG ATC ACC GTC ACG CAA GGC AAA CG  GTGAGTCCGC CCTGAGCTGG
Thr Asn Leu Thr Val Ile Thr Val Thr Gln Gly Lys Arg
```

*FIG. 5E*

```
                                           1530         1540         1550         1561              1570         1579
                      CCTCAATAGC GATATTGACG AGTCCATGCC CTCCCCAG G TAC CGC TTC CGC CTT GTG TCG
                                                                 Tyr Arg Phe Arg Leu Val Ser 1588            1597             1606             1615             1624             1633
ATC TCG TGC GAC CCC AAC TTC ACG TTC TCG ATC GAC GGG CAC AAC ATG ACC ATC
Ile Ser Cys Asp Pro Asn Phe Thr Phe Ser Ile Asp Gly His Asn MET Thr Ile 1642            1651             1660             1669             1678             1687
ATC GAG GTG GAC GGT GTC AAC CAC GAG GCC TTG GAC GTC GAC TCC ATT CAG ATT
Ile Glu Val Asp Gly Val Asn His Glu Ala Leu Asp Val Asp Ser Ile Gln Ile 1696            1705             1714             1724             1734             1744
TTT GCG GGG CAG CGG TAC TCC TTC ATC GTACGTTCCC TTGCCCTGT GCTATATCCG
Phe Ala Gly Gln Arg Tyr Ser Phe Ile 1754            1764             1774             1785             1794             1803
CCCGTCTGCT CACAGAGGCT TCTATATCGC AG CTC AAC GCC AAC CAG TCC ATC GAC AAC
                                       Leu Asn Ala Asn Gln Ser Ile Asp Asn
```

```
                1812      1821      1830      1839      1848      1857
TAC TGG ATC CGC GCG ATC CCC AAC ACC GGT ACC ACC GAC ACC ACG GGC GGC GTG
Tyr Trp Ile Arg Ala Ile Pro Asn Thr Gly Thr Asp Thr Thr Gly Gly Val 1866      1875      1884      1893      1902      1911
AAC TCT GCT ATT CTT CGC TAC GAC GCA GAA GAT ATC GAG CCT ACG ACC AAC
Asn Ser Ala Ile Leu Arg Tyr Asp Ala Glu Asp Ile Glu Pro Thr Thr Asn 1920      1929      1938      1947      1956      1965
GCC ACC ACC TCC GTC ATC CCT CTC ACC GAG ACG GAT CTG GTG CCG CTC GAC AAC
Ala Thr Ser Val Ile Pro Leu Thr Glu Thr Asp Leu Val Pro Leu Asp Asn 1974      1983      1992      2001      2010      2019
CCT GCG GCT CCC GGT GAC CCC CAG GGC GGT GTT GAC CTG GCT ATG AGT CTC
Pro Ala Ala Pro Gly Asp Pro Gln Val Gly Gly Val Asp Leu Ala MET Ser Leu 2028      2041      2051      2061      2071      2081
GAC TTC TCC TTC GTGAGTCCCA CAGCACTCCG CGCCATTCCG CTTATTTACG CAGGAGTATT
Asp Phe Ser Phe
```

```
         2090         2099         2108         2117         2126         2135
GTTCAG AAC GGT TCC AAC TTC TTT ATC AAC AAC GAG ACC TTC GTC CCG CCC ACA
       Asn Gly Ser Asn Phe Phe Ile Asn Asn Glu Thr Phe Val Pro Pro Thr
                 2144              2153              2162              2171              2180              2189

GTT CCC GTG CTC CTG CAG ATT TTG AGT GGT GCG CAG GAC GCG GCG AGC CTG CTC
Val Pro Val Leu Leu Gln Ile Leu Ser Gly Ala Gln Asp Ala Ala Ser Leu Leu
       2198              2207              2216              2225              2234              2243

CCC AAC GGG AGT GTC TAC ACA CTC CCT TCG AAC TCG ACC ATT GAG ATC TCG TTC
Pro Asn Gly Ser Val Tyr Thr Leu Pro Ser Asn Ser Thr Ile Glu Ile Ser Phe
       2252              2261              2270              2279              2288              2297

CCC ATC ATC ACC ACC GAC GGT GTT CTG AAC GCG CCC GGT GCT CCG CAC CCG TTC
Pro Ile Ile Thr Thr Asp Gly Val Leu Asn Ala Pro Gly Ala Pro His Pro Phe
       2306              2319              2329              2339              2349              2359

CAT CTC CAC GGC GTAAGTCCTT GCTTCCTCA GTGCCTCGCT TCCACGAGT CCACTGATCC
His Leu His Gly
```

FIG. 5H

```
                2369        2380         2389         2398         2407         2416
     CACACATCCC ATGTGCAG CAC ACC TTC TCG GTG CGC AGC GCC GGG AGC TCG ACC
                         His Thr Phe Ser Val Arg Ser Ala Gly Ser Ser Thr 2425        2434         2443         2452         2461         2470
     TTC AAC TAC GCC AAC CCA GTC CGC GAC ACC GTC AGT ACT GGT AAC TCT GGC
     Phe Asn Tyr Ala Asn Pro Val Arg Asp Thr Val Ser Thr Gly Asn Ser Gly 2479        2488         2504         2514         2524         2534
     GAC AAC GTC ACT ATC CGC TTC ACG GTACGTCTTC TCCGGAGCCC TCCCACCCGT GTGTCCGCTG
     Asp Asn Val Thr Ile Arg Phe Thr 2544        2554         2564         2574         2583         2592
     AGCGCTGAAC ACCGCCCACC GTGCTGCTGC TGGCGCAG ACC GAC AAC CCA GGC CCG TGG
                                               Thr Asp Asn Pro Gly Pro Trp 2601        2610         2619         2628         2637         2646
     TTC CTC CAC TGC CAC ATC GAC TTC CAC CTG GAG GCC GGC TTC GCC ATC GTC TGG
     Phe Leu His Cys His Ile Asp Phe His Leu Glu Ala Gly Phe Ala Ile Val Trp
```

FIG. 5I

```
     2655           2664           2673           2682                2699
 GGG GAG GAC ACT GCG GAC ACC GCG TCC GCG AAT CCC GTT CCT A          GTACGTCGTG
 Gly Glu Asp Thr Ala Asp Thr Ala Ser Ala Asn Pro Val Pro Thr 2709           2719           2729           2739           2749           2759
CCTGCTGAGC TCTTTGTGCC CGAACAGGGT GCTGATCGTG CCTTCCTCCG TGCAG  CG  GCG TGG
                                                                    Ala Trp 2768           2777           2786           2795      2804              2817
                                                           ⌒
 AGC GAT TTG TGC CCC ACT TAC GAT GCT TTG GAC TCG TCC GAC CTC TGATCGACAA
 Ser Asp Leu Cys Pro Thr Tyr Asp Ala Leu Asp Ser Ser Asp Leu 2827           2837           2847           2857           2867           2877           2887
GGCATGAAGG CTGAAGCAGC TGCGGTCAAT TCTCGAACAC ACTTTACTCG AACATTCATT TTTCTTTGGC
       2897           2907           2917
TCGGGATCGG AACAAATCAT GGGGGGGCCG GACCGTCT
```

FIG.5J

DYE COMPOSITIONS CONTAINING PURIFIED POLYPORUS LACCASES AND NUCLEIC ACIDS ENCODING SAME

This application is a divisional of Ser. No. 08/441,147 filed May 15, 1995.

FIELD OF THE INVENTION

The present invention relates to isolated nucleic acid fragments encoding a fungal oxidoreductase enzyme and the purified enzymes produced thereby. More particularly, the invention relates to nucleic acid fragments encoding a phenol oxidase, specifically a laccase, of a basidiomycete, Polyporus.

BACKGROUND OF THE INVENTION

Laccases (benzenediol:oxygen oxidoreductases) are multi-copper-containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, Polyporus and perfect forms of Rhizoctonia. Laccases exhibit a wide range of substrate specificity, and each different fungal laccase usually ditters only quantitatively from others in its ability to oxidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima, and these may also differ depending on the specific substrate. A number of these fungal laccases have been isolated, and the genes for several of these have been cloned. For example, Choi et al. (Mol. Plant-Microbe Interactions 5: 119–128, 1992) describe the molecular characterization and cloning of the gene encoding the laccase of the chestnut blight fungus, *Cryphonectria parasitica*. Kojima et al. (J. Biol. Chem. 265: 15224–15230, 1990; JP 2-238885) provide a description of two allelic forms of the laccase of the white-rot basidiomycete *Coriolus hirsutus*. Germann and Lerch (Experientia 41: 801,1985; PNAS USA 83: 8854–8858, 1986) have reported the cloning and partial sequencing of the *Neurospora crassa* laccase gene. Saloheimo et al. (J. Gert. Microbiol. 137: 1537–1544, 1985; WO 92/01046) have disclosed a structural analysis of the laccase gene from the fungus *Phlebia radiata*.

Attempts to express laccase genes in heterologous fungal systems frequently give very low yields (Kojima et al., supra; Saloheimo et al., Bio/Technol. 9: 987–990, 1991). For example, heterologous expression of *Phlebia radiata* laccase in *Trichoderma reesei* gave only 20 mg per liter of active enzyme in lab-scale fermentation (Saloheimo, 1991, supra). Although laccases have great commercial potential, the ability to express the enzyme in significant quantities is critical to their commercial utility. Previous attempts to express basidiomycete laccases in recombinant hosts have resulted in very low yields. The present invention now provides novel basidiomycete laccases which are well expressed in Aspergillus.

SUMMARY OF THE INVENTION

The present invention relates to a DNA construct containing a nucleic acid sequence encoding a Polyporus laccase. The invention also relates to an isolated laccase encoded by the nucleic acid sequence. Preferably, the laccase is substantially pure. By "substantially pure" is meant a laccase which is essentially (i.e., $\geq 90\%$) free of other non-laccase proteins.

In order to facilitate production of the novel laccase, the invention also provides vectors and host cells comprising the claimed nucleic acid sequence, which vectors and host cells are useful in recombinant production of the laccase. The sequence is operably linked to transcription and translation signals capable of directing expression of the laccase protein in the host cell of choice. A preferred host cell is a fungal cell, most preferably of the genus Aspergillus. Recombinant production of the laccase of the invention is achieved by culturing a host cell transformed or transfected with the construct of the invention, or progeny thereof, under conditions suitable for expression of the laccase protein, and recovering the laccase protein from the culture.

The laccases of the present invention are useful in a number of industrial processes in which oxidation of phenolics is required. These processes include lignin manipulation, juice manufacture, phenol polymerization and phenol resin production.

BRIEF DESCRIPTION OF THE FIGURES

FIGS. 1A–1I show the DNA sequence and translation of genomic clone 21GEN, containing LCC1 (SEQ ID NO. 1)

FIGS. 2A–2K show the DNA sequence and translation of genomic clone 23GEN, containing LCC2 (SEQ ID NO. 3)

FIGS. 3A–3L show the DNA sequence and translation of genomic clone 24GEN, containing LCC3 (SEQ ID NO. 5)

FIGS. 4A–4M show the DNA sequence and translation of genomic clone 31GEN, containing LCC4 (SEQ ID NO. 7)

FIGS. 5A–5J show the DNA sequence and translation of genomic clone 41GEN, containing LCC5 (SEQ ID NO. 9)

DETAILED DESCRIPTION OF THE INVENTION

Figure 6:
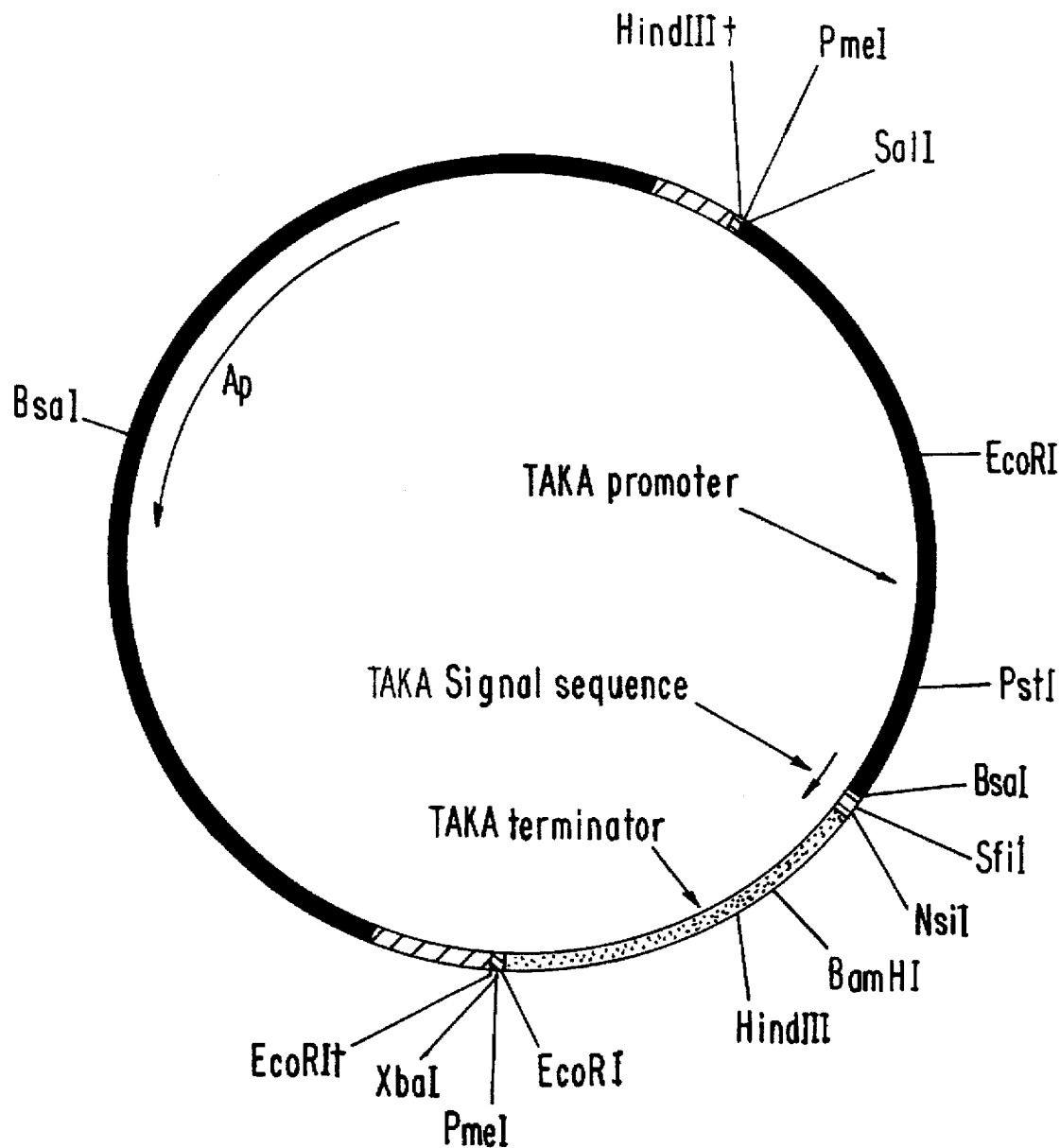
FIG. 6 shows the structure of vector pMWR1

*Polyporus pinsitus* is a basidiomycete, also referred to as *Trametes villosa*. Polyporus species have previously been identified as laccase producers (Fahraeus and Lindeberg, Physiol. Plant. 6: 150–158, 1953). However, there has been no previous description of a purified laccase from *Polyporus pinsitus*. It has now been determined that *Polyporus pinsitus* produces at least two different laccases, and the genes encoding these laccases can be used to produce relatively large yields of the enzyme in convenient host systems such as Aspergillus. In addition, three other genes which appear to code for laccases have also been isolated.

Initial screenings of a variety of fungal strains indicate that *Polyporus pinisitus* is a laccase producer. The production of laccase by *P. pinsitus* is induced by 2,5-xylidine. Attempts are first initiated to isolate the laccase from the supernatant of the induced strains. Anion exchange chromatography identifies an approximately 65 kD (on SDS-PAGE) protein which exhibits laccase activity. The enzyme is purified sufficiently to provide several internal peptide sequences, as well as an N-terminal sequence. The initial sequence information indicates the laccase has significant homology to that of *Coriolus hirsutus*, as well as to an unidentified basidiomycete laccase (Coll et al., Appl. Environ. Microbiol. 59: 4129–4135, 1993. Based on the sequence information, PCR primers are designed and PCR carried out on cDNA isolated from *P. pinsitus*. A band of the expected size is obtained by PCR, and the isolated fragment linked to a cellulase signal sequence is shown to express an active laccase in *A. oryzae*, but at low levels. One of the PCR fragments is also used as a probe in screening a *P. pinsitus* cDNA library. In this manner, more than 100 positive clones are identified. The positive clones are characterized and the ends of the longest clones sequenced; none of the clones are found to be full-length.

Further attempts to isolate a full length clone are made. A 5–6 kb BamHI size-selected *P. pinsitus* genomic library is probed with the most complete cDNA fragment isolated as described above. Initial screening identifies one clone 24GEN(LCC3) having homology to the cDNA, but which is not the cDNA-encoded laccase and also not full length. Subsequent screening of a 7–8 kb BamHI/EcoRi size-selected library indicates the presence of at least two laccases; partial sequencing shows that one, called 21GEN (LCC1), is identical to the original partial cDNA clone isolated, and the second, called 31GEN(LCC4) is a new, previously unidentified laccase. Secondary screenings of an EMBL4 genomic bank with LCC1 as probe identifies a class of clone containing the entire LCC1 insert as well as the 5' and 3' flanking regions. Screening of the EMBL bank with LCC3 identifies two additional clones encoding laccases which had not previously been identified, 41GEN(LCC5) and 23GEN(LCC2) and which differed structurally from the other three clones LCC1, LCC3, and LCC4. The nucleic acid and predicted amino acid sequences of each of the laccases is presented in FIGS. 1–5, and in SEQ ID NOS. 1–10. A comparison of the structural organization of each of the laccases is presented in Table 2. The laccases are generally optimally active at acid pH, between about 4–5.5.

LCC1 is used to create expression vectors, which are in turn used to transform various species of Aspergillus. Transformation is successful in all species tested, although expression levels are highest in *Aspergillus niger*. Shake flask cultures are capable of producing 15 or more mg/liter of laccase, and in lab-scale fermentors, yields of over 300 mg/liter are observed. This is a significant improvement over laccase levels observed previously with other laccases and other fungal host cells.

According to the invention, a Polyporus gene encoding a laccase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American., 1980, 242:74–94; and in Sambrook et al., Molecular Cloning, 1989.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been ingrated.

In the vector, the laccase DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), or the promoters of the *Bacillus subtilis* xylA and xylB genes. In a yeast host, a useful promoter is the eno-1 promoter. For transcription in a fungal host, examples of useful promoters are those derived from the gene encoding A. oryzae TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae triose* phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B.subtilis* or *B.licheniformis*, or one which confers antibiotic resistance such as ampicillin, kanamycin, chloramphenicol or tetracycline resistance. Examples of Aspergillus selection markers include amdS, pyrG, argB, niaD, sC, trpC and hygB, a marker giving rise to hygromycin resistance. Preferred for use in an Aspergillus host cell are the amdS and pyrG markers of *A. nidulans* or *A. oryzae*. A frequently used mammalian marker is the dihydrofolate reductase (DHFR) gene. Furthermore, selection may be accomplished by co-transformation, e.g. as described in WO 91/17243.

It is generally preferred that the expression gives rise to a product which is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the signal sequence for *A. oryzae* TAKA amylase, *A. niger* neutral amylase, the *Rhizomucor miehei* aspartic proteinase signal, the *Rhizomucor miehei* lipase signal, the martogenic amylase from Bacillus NCIB 11837, *B. stearothermophilus* α-amylase, or *B. licheniformis* subtilisin.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtills*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus Churingiensis*, or *Streptomyces lividans* or *Screptomyces murinus*, or gram negative bacteria such as *E. coli*. The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e.g. *Saccharomyces cerevisiae*. Useful filamentous fungi may be selected from a species of Aspergillus, e.g. *Aspergillus oryzae* or *Aspergillus niger*. Alternatively, a strain of a Fusarium species, e.g. *F. oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

The present invention thus provides a method of producing a recombinant laccase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g. in catalogues of the American Type Culture Collection).

In a preferred embodiment, the recombinant production of laccase in culture is achieved in the presence of an excess amount of copper. Although trace metals added to the culture medium typically contain a small amount of copper, experiments conducted in connection with the present invention show that addition of a copper supplement to the medium can increase the yield of active enzyme many-fold. Preferably, the copper is added to the medium in soluble form, preferably in the form of a soluble copper salt, such as copper chloride, copper sulfate, or copper acetate. The final concentration of copper in the medium should be in the range of from 0.2–2 mM, and preferably in the range of from 0.05–0.5 mM. This method can be used in enhancing the yield of any recombinantly produced fungal laccase, as well as other copper-containing enzymes, in particular oxidoreductases.

The resulting enzyme may be recovered from the medium by conventional procedures including separating the cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of laccase is achieved in a fungal host cell, such as Aspergillus. As described in detail in the following examples, the laccase gene is ligated into a plasmid containing the *Aspergillus oryzae* TAKA α-amylase promoter, and the *Aspergillus nidulans* amdS selectable marker. Alternatively, the amdS may be on a separate plasmid and used in co-transformation.

The plasmid (or plasmids) is used to transform an Aspergillus species host cell, such as *A. oryzae* or *A. niger* in accordance with methods described in Yelton et al. (PNAS USA 81: 1470–1474,1984).

It is of particular note that the yields of Polyporus laccase in the present invention, using Aspergillus as host cell are unexpectedly and considerably higher than has previously been reported for expression of other laccases in other host cells. It is expected that the use of Aspergillus as a host cell in production of laccases from other basidiomycetes, such as Coriolus or Trametes, will also produce larger quantities of the enzyme than have been previously obtainable. The present invention therefore also encompasses the production of such Polyporus-like laccases in Aspergillus recombinant host cells.

Those skilled in the art will recognize that the invention is not limited to use of the nucleic acid fragments specifically disclosed herein, for example, in FIGS. 1–5. It will also be apparent that the invention encompasses those nucleotide sequences that encode the same amino acid sequences as depicted in FIG. 1–5, but which differ from the specifically depicted nucleotide sequences by virtue of the degeneracy of the genetic code. Also, reference to FIGS. 1–5 in the specification and the claims will be understood to encompass both the genomic sequence depicted therein as well as the corresponding cDNA and RNA sequences, and the phrases "DNA construct" and "nucleic acid sequences" as used herein will be understood to encompass all such variations. "DNA construct" shall generally be understood to mean a DNA molecule, either single- or double-stranded, which may be isolated in partial form from a naturally occurring gene or which has been modified to contain segments of DNA which are combined and juxtaposed in a manner which would not otherwise exist in nature.

In addition, the invention also encompasses other Polyporus laccases, including alternate forms of laccase which may be found in *Polyporus pinsitus* and as well as laccases which may be found in other fungi falling within the definition of Polyporus as defined by Fries, or synonyms thereof as stated in Long et al., 1994, ATCC Names of Industrial Fungi, ATCC, Rockville, Md. Identification and isolation of laccase genes from sources other than those specifically exemplified herein can be achieved by utilization of the methodology described in the present examples, with publicly available Polyporus strains. Alternately, the sequence disclosed herein can be used to design primers and/or probes useful in isolating laccase genes by standard PCR or southern hybridization techniques. Other named Polyporus species include, but are not limited to, *P. zonatus, P. alveolaris, P. arcularius, P. australiensis, P. badius, P. biformis, P. brumalis, P. ciliatus, P. colensoi, P. eucalyptorum, P. meridionalis, P. varius, P. palustris, P. rhizophilus, P. rugulosus, P. squamosus, P. tuberaster*, and *P. tumulosus*. Also encompassed are laccases which are synonyms, e.g., anamorphs or perfect states of species or strains of the genus Polyporus. Strains of Polyporus are readily accessible to the public in a number of culture collections, such as the American Type Culture Collection (ATCC), e.g., ATCC 26721, 9385, 11088, 22084, Deutsche Sammlung yon Mikroorganismen und Zellkulturen GmbH (DSM),e.g., DSM 1021, 1023, and 1182; and Centraalbureau Voor Schimmelcultures (CBS), e.g., CBS 678.70, 166.29, 101.15, 276.31, 307.39, 334.49, and 332.49. The invention also encompasses any variant nucleotide sequence, and the protein encoded thereby, which protein retains at least about an 80% homology, preferably at least about 85%, and most preferably at least about 90–95% homology with any one of the amino acid sequences depicted in FIGS. 2–5, and which qualitatively retains the laccase activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by conducting a standard ABTS oxidation method, such as is described in the present examples.

The protein can be used in number of different industrial processes. These processes include polymerization of lignin, both Kraft and lignosulfates, in solution, in order to produce a lignin with a higher molecular weight. Such methods are described in, for example, Jin et al., Holzforschung 45(6): 467–468, 1991; U.S. Pat. No. 4,432,921; EP 0 275 544; PCT/DK93/00217, 1992.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, Current opinion in Biotechnology 3: 261–266, 1992; J. Biotechnol. 25: 333–339, 1992; Hiroi et al., Svensk papperstidning 5: 162–166, 1976.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406, WO 92/18683, EP 0495836 and Calvo, Mededelingen van de Faculteit Landbouw-wetenschappen/ Rijiksuniversitet Gent. 56: 1565–1567, 1991; Tsujino et al., J. Soc. Chem. 42: 273–282, 1991.

The laccase is particularly well-suited for use in hair dyeing. In such an application, the laccase is contacted with a dye precursor, preferably on the hair, whereby a controlled oxidation of the dye precursor is achieved to convert the precursor to a dye, or pigment producing compound, such as a quinoid compound. The dye precursor is preferably an aromatic compound belonging to one of three major chemical families: the diamines, aminophenols (or aminonaphthols) and the phenols. The dye precursors can be used alone or in combination. At least one of the intermediates in the copolymerization must be an ortho- or para-diamine or aminophenol (primary intermediate). Examples of such are found in Section V, below, and are also described in U.S. Pat. No. 3,251,742, the contents of which are incorporated herein by reference. In one embodiment, the starting materials include not only the enzyme and a primary intermediate, but also a modifier (coupler) (or combination of modifiers), which modifier is typically a meta-diamine, meta-aminophenol, or a polyphenol. The modifier then reacts with the primary intermediate in the presence of the laccase, converting it to a colored compound. In another embodiment, the laccase can be used with the primary intermediate directly, to oxidize it into a colored compound. In all cases, the dyeing process can be conducted with one or more primary intermediates, either alone or in combination with one or more modifiers. Amounts of components are in accordance with usual commericial amounts for similar components, and proportions of components may be varied accordingly.

The use of this laccase is an improvement over the more traditional use of $H_2O_2$, in that the latter can damage the hair, and its use usually requires a high pH, which is also damaging to the hair. In contrast, the reaction with laccase can be conducted at alkaline, neutral or even acidic pH, and the oxygen needed for oxidation comes from the air, rather than via harsh chemical oxidation. The result provided by the use of the Polyporus laccase is comparable to that achieved with use of $H_2O_2$, not only in color development, but also in wash stability and light fastness. An additional commercial advantage is that a single container package can be made containing both the laccase and the precursor, in an oxygen free atmosphere, which arrangement is not possible with the use of $H_2O_2$.

The present laccase can also be used for the polymerization of phenolic or aniline compounds present in liquids. An example of such utility is the treatment of juices, such as apple juice, so that the laccase will accelerate a precipitation of the phenolic compounds present in the juice, thereby producing a more stable juice. Such applications have been described in Stutz, Fruit processing 7/93, 248–252, 1993; Maier et al., Dr. Lebensmittel-rindschau 86(5): 137–142, 1990; Dietrich et al., Fluss. Obst 57(2): 67–73, 1990.

Laccases such as the Polyporus laccase are also useful in soil detoxification (Nannipieri et al., J. Environ. Qual. 20: 510–517,1991; Dec and Bollag, Arch. Environ. Contam. Toxicol. 19: 543–550, 1990).

The invention is further illustrated by the following non-limiting examples.

EXAMPLES

I. ISOLATION OF A POLYPORUS PINISITUS LACCASE ENZYME MATERIALS AND METHODS

1. Enzymatic assays

Unless otherwise stated, throughout the examples, laccase activity is determined by syringaldazine and 2,2'-bisazino (3-ethylbenzthiazoline-6-sulfonic acid) (ABTS), as follows. The oxidation of syringaldazine is monitored at 530 nm with 19 µM substrate. In 25 mM sodium acetate, 40 µM cupric sulfate, pH 5.5, at 30° C., the activity is expressed as LACU (µmole/min). For pH profile studies, Britton & Robinson (B&R) buffers are used, and are prepared according to the protocol described in Quelle, Biochemisches Taschenbuch, H. M. Raven, II. Teil, S.93 u. 102, 1964. ABTS oxidation is carried out with 1 mM ABTS in 0.1M NaAc, pH 5.0 at room temperature by monitoring either $\Delta Abs_{405}$ in a 96-well plate (Costar) or $\Delta Abs_{418}$ in a quartz cuvette. The overlay ABTS oxidase activity assay is carried out by pouring cooled ABTS-agarose (0.03–0.1 g ABTS, 1 g agarose, 50 ml $H_2O$, heated to dissolve agarose) over a native IEF gel or PAGE and incubating at room temperature.

2. Initial isolation of laccase

In order to isolate the laccase, 800 ml of culture fluid is filtered by HFSC on a Supra filter (slow filtering). The clear filtrate is then concentrated and washed on an Amicon cell with a GR81 PP membrane to a volume of 72 ml.

One ml aliquots of laccase are bound to a Q-sepharose HP (Pharmacia, Sweden) column, equilibrated with 0.1M phosphate, pH7 and the laccase is eluted with a NaCl gradient. In all, 10×1 ml samples are purified, pooled, concentrated and washed by ultrafiltration using a membrane with a molecular weight cut-off of 6 kD.

3. Secondary purification

In a second purification, a fermentation broth is filtered and concentrated by ultrafiltration. The starting material contains 187 LACU/ml. The concentrate is quick-filtered on a Propex 23 filter (P & S Filtration), with 3% Hyflo Cuper-Cel (HSC; Celite Corporation), followed by two ultrafiltration on a Filtron filter with two membranes, each with a molecular weight cut of of 3 kD. The resulting sample (2.5 mS/cm, pH 7.0, at 4° C.) is applied to a 130 ml Q-Sepharose column, equilibrated with sodium phosphate, 1.1 mS/cm, pH 7.0. Under these conditions the laccase does not bind to the column, but elutes slowly from the column during the application and wash with the equilibration buffer, resulting in a partial separation from other brownish material.

This partially purified preparation of 1.0 mS, pH 7.0 at 20° C. is applied to a Q-sepharose column. The column is equilibrated with 20 mM sodium phosphate, 2.2 mS, pH 7.0. Under these conditions, the laccase binds to the column and is eluted by a gradient of 0–1M NaCl over 20 column volumes.

3. Sequencing

For internal peptide sequencing, the purified protein is digested with trypsin, followed by peptide purification with HPLC. Purified peptides are sequenced in an Applied Biosystems 473A sequencer.

B. RESULTS AND DISCUSSION

1. Initial characterization

Total yield of the initial purification is about 50 mg (estimated at A280 nm). The purified enzyme has a rich blue color, and appears as only two very close bands on SDS-PAGE at about 65 kd. A native PAGE overlaid with substrate shows that both bands have laccase activity with ABTS. The absorption spectrum shows that besides an absorption at A280 nm, the purified laccase also shows absorption at about 600 nm.

2. Sequencing

A N-terminal determination of the protein initially purified shows a single sequence:

Gly-Ile-Gly-Pro-Val-Ala-Asp-Leu-Thr-Ile-Thr-Asn-Ala-Ala-Ala-Val-Ser-Pro-Asp-Gly-Phe-Pro.

Since the N-terminal sequence is not the ideal sequence for constructing a probe, additional experiments with a trypsin digest are conducted, followed by further purification (described above) and sequencing of fragments 2. Secondary purification and characterization In the second purification, the second Q-Sepharose chromatographic step yields the following pools:

Q-Sepharose-2-pool-1 40 ml 112 LACU 47 $LACU/A_{280}$
Q-Sepharose-2-pool-3 80 ml 385 LACU 65 $LACU/A_{280}$ The elution yields >80% of the applied amount. The highly purified preparation Q-Sepharose-2-pool-3 has an $A_{280}$=5.9, and $A_{280}/A_{260}$=1.4. The purity of the laccase in the starting material is extremely high on a protein basis but the starting material is a very dark brown color. In SDS-PAGE, a double band is seen, with a dominating 65 kD band and a smaller 62 kD band. By anionic chromatography, only the dominating band is seen in the first peak (Q-Sepharose-2-pool-1), whereas both bands are seen in the second peak (Q-Sepharose-2-pool-3).

3. Sequence

A number of internal peptide sequences are determined, and compared with the *Coriolus hirsutus*(Ch) laccase sequence. The identified fragments are as follows:

Tryp 13: Ser-Pro-Ser-Thr-Thr-Thr-Ala-Ala-Asp-Leu

Tryp 14: Ser-Ala-Gly-Ser-Thr-Val-Tyr-Asn-Tyr-Asp-Asn-Pro-Ile-Phe Arg

Tryp 16:

Sequence 1: Ser-Thr-Ser-Ile-His-Trp-His-Gly-Phe-Phe-Gln-Lys

Sequence 2: Gly-Ile-Gly-Pro-Val-Ala-Asp-Leu-Thr-Ile-Thr-Asn-Ala-Ala-Val

Tryp 18: Gly-Ile-Gly-Pro-Val-Ala-ASp-Leu-Thr-Ile-Thr-Asn

Tryp 19:

Sequence 1: Leu-Gly-Pro-Ala-Phe-Pro-Leu-Gly-Ala-Asp-Ala-Thr-Leu-Ile

Sequence 2: Phe-Gln-Leu-Asn-Val-Ile-Asp-Asn-Asn-Thr-Thr-His-Thr-Met

Tryp 25: Tyr-Ser-Phe-Val-Leu-Glu-Ala-Asn-Gln-Ala-Val-Asp-Asn-Tyr-Trp-Ile-Arg

Tryp 27 Gly-Thr-Asn-Trp-Ala-Asp-Gly-Pro-Ala-Phe

II. ISOLATION OF A *POLYPORUS PINISITUS* LACCASE CDNA CLONE

A. MATERIALS AND METHODS

1. RNA preparation

RNA is isolated from 10 grams of *P. pinsitus* mycelium grown under xylidine induction for 6.5 hours, using the guanidium/CsCl cushion method. The RNA is poly-A selected on an oligo-dT column, using standard conditions. 120 μg mRNA is obtained and stored as lyophilized pellet in 5 μg aliquots at −80° C.

2. Single stranded cDNA

Single stranded cDNA is synthesized using the reverse transcriptase "Super Script" (BRL) according to manufacturer's directions.

3. Construction of cDNA library

A cDNA library is constructed using the librarian IV cDNA kit (Invitrogen). Fifty cDNA pools, each containing approximately 5000 individual transformants, are obtained.

4. PCR

PCR is conducted under the following standard conditions: 100 pmol of each primer, 10 μl 10× PCR buffer (Perkin-Elmer), 40 μl dNTP 0.5 mM, 2 μl single stranded cDNA(or approximately 100 ng chromosomal DNA or 100 ng PCR fragment), H$_2$O to 100 μl, 2.5U Taq polymerase. The cycles are 3×(40° C./two minutes, 72° C./two minutes, 94° C./one minute) followed by 30×(60° C./two minutes, 72° C./two minutes, 94° C./1 minute).

B. RESULTS AND DISCUSSION

1. Cloning of *Polyporus pinsitus* laccase

PCR is carried out with the primer #3331:

ACCAGNCTAGACACGGGNTC/AGATACTG/ACGNGAGAGCGGAC/TTGCTGGTC ACTATCT-TCGAAGATCTCG and primer #3332:

CGCGGCCGCTAGGATCCTCACAATGGCCAA/CTCTCTG/CCTCG/ACCTTC.

A clear band of about 1500 bp is obtained. The DNA is digested with NotI/HindIII, and fractionated on an agarose gel. The upper band (fragment #42) is purified and cloned into the Aspergillus vector pHD423. No transformants are obtained. Several attempts are carried out in order to clone the fragment, including redigestion with the restriction enzymes, phosphorylation of the ends, filling in with klenow and blunt-end cloning in SmaI cut puC18, without success. Hybridization with a laccase probe based on the laccase described in Coll et al., supra, indicates that the PCR product could be the *P. pinsitus*, laccase. In a new attempt to clone the PCR fragment, a new PCR reaction is carried out, using the same conditions as for fragment #42. Again the result is a fragment of about 1500 bp (fragment #43). This time the fragment is cut with HindIII/BamHI, and ligated to HindIII/BamHI-cut pUC18. Three clones, #43-/A,-B,-G are found to contain a fragment of 1500 bp. Partial sequencing reveals that these fragments are laccase related.

2. Expression of *Polyporus pinsitus* laccase

To express the laccase, the fragment #43 is joined to a signal sequence from a 43 kD cellulase. The primer pHD433 (TAGCGGATCCCACAATGCGTTCCTCCCCCCTCCTC-CCGTCCGCCGTTGTGGCCGCCCTGCCGGTGTTGGC-CCTTGCCGGCATTGGGCCCGTCGCGGACC) is used in a standard PCR reaction with a pUC forward primer (New England Biolabs). All three clones are used as templates in order to minimize the risk of working with DNA containing errors.

The PCR generated DNA from the reaction with a primer pHD433 and template 43-A and 43-G is cut with HindIII/BamHI and cloned into the Aspergillus expression vector pHD414(described in detail below). Several transformants are obtained.

Clones pHD433/43A-1,2, pHD433/43G-2,-3 are transformed into *A. oryzae*. The transformants from each transformation (between 3–10) are analyzed for laccase production. Activity is only obtained with pHD433/43G-3. The positive transformants (numbers 1, 4, 6) are reisolated on amdS plates, and retested. In an additional transformation round a further ten transformants are obtained with pHD433/43G-3. The clones #20, 23, 26, 28, and 29 are positive. The clones are reisolated and two single isolates are analyzed for laccase expression semiquantitatively by color development in an ABTS assay at pH 4.5. On a scale of +—+++, several clones show moderate to strong expression of laccase.

Further cloning is conducted to identify a full length clone. A xylidine-induced cDNA library consisting of approximately 350,000 transformants is screened using fragment #42-4 as a probe. More than 100 positive clones are detected. The clones are purified, rescreened, and analyzed on Southern blots. Two of the longest clones are further characterized by DNA sequence determination. The longest clones are found to be identical and found to contain a poly-A stretch in the 3' end and to start at the amino acid number 4 in the amino terminus. A partial DNA sequence is determined from different clones.

pHD433/43G-3 is then used in further cloning studies as described in the following Section IV.

III. PURIFICATION AND CHARACTERIZATION OF ADDITIONAL *POLYPORUS PINSITUS* LACCASE WILD-TYPE ENZYMES

A. MATERIALS AND METHODS

1. Culture conditions

Shake flasks (250 ml medium/2.8 l baffled flask) are inoculated with several agar plugs taken from a week-old PDA plate of *P. pinsitus*. The medium contains, per liter, 10 g glucose, 2.5 g L-asparagine, 0.2 g L-phenylalanine, 2.0 g yeast extract, 2.0 g KH$_2$PO$_4$, 0.5 g MgSO$_4$.7H$_2$O, 2.0 mlAMG trace metals, 0.002 g CuSO$_4$.7H$_2$O, 1.0 g citric acid, made with tape water, pH 5.0 before autoclaving. The cultures are grown at 18°–22° C. on a rotary shaker with low agitiation (~100 rpm). After 7 days, the pH of each shake flask is adjusted to ~6.0 by the addition of 0.25 ml 5N NaOH and the cultures are induced by adding 0.5 ml of a 2,5-xylidine stock solution (xylidine diluted 1:10 into ethanol) to each flask. Flasks are incubated for an additional 24 hours, at which time the culture supernatant from each flask is recovered.

2. Materials.

Chemicals used as buffers are commercial products of at least reagent grade. Endo/N-glucosidase F is from Boehringer-Mannheim. Chromatography is performed on Pharmacia FPLC. Spectroscopic assays are conducted on either a spectrophotometer (Shimadzu PC160) or a microplate reader (Molecular Devices).

3. Purification

Culture broth is filtered first on cheesecloth and centrifuged at 1000× g to remove gelatinous pinkish xylidine polymer. The supernatant is then filtered on Whatman #2 paper and concentrated from 1500 to 250 ml on S1Y100 (Amicon, Spiral concentrator) at 4° C. The concentrated broth is diluted with water until it reaches 0.8 mS (from 2.5 mS) and then concentrated on S1Y100 to 250 ml. The washed broth, thawed from −20° C. freezing overnight, is subjected to Whatman #2 paper filtration to remove residual pinkish material, and then pH adjusted by NaOH from pH 6.1 to pH 7.7. This yellowish broth, 275 ml with 0.8 mS, is applied on a Q-Sepharose XK-26 column (~64 ml gel) equilibrated with 10 mM Tris-HCl, pH 7.7, 0.7 mS. The first active laccase fraction runs through during loading and washing by the equilibrating buffer. The elution is carried out by a linear gradient of 0–0.5M NaCl in the equilibrating buffer over 8.8 bed-volume. The second and third active fractions are eluted around 0.15 and 0.35M NaCl, respectively. NO more active fractions are detected when the column is washed sequentially with 2M NaCl and with 1 mM NaOH. The active fractions are pooled, adjusted to ~10 mS, concentrated on Centricon-10(Amicon), and then applied onto Superdex 75(HR10/30, 24 ml, Pharmacia) equilibrated with 10 mMTris-HCl, 0.15M NaCl, pH 8, 14 mS. During elution with the application buffer, laccase fractions are eluted off using the same elution volume for all three Q-Sepharose fractions, indicating very similar native molecular weight. The purity of the laccase is tested on SDS-PAGE.

4. Protein analysis

PAGE and native IEF are carried out on a Mini Protean II and a Model 111 Mini IEF cells(Bio-Rad). Western blots are carried out on a Mini trans-blot cell(Bio-Rad) with an alkaline phosphatase assay kit(Bio-Rad). The primary antibodies are diluted 1000-fold during blotting. N-terminus sequencing is performed on an Applied Biosystems (ABI) 476A protein sequencer using liquid phase TFA delivery for cleavage and on-line HPLC for identification of PTH-amino acids. Standard Fast Cycles and Pre-Mix Buffer System is used according to manufacturer's instructions. Deglycosylation with glycosidase is done as follows: 3 μg of protein and 3.6 units of glycosidase in 0.25M NaAc, pH 5, 20 mM EDTA, 0.05% 2-mercaptoethanol is incubated at 37° C. for 18 hours with ovalbumin and bovine serum albumin serving as positive and negative control, respectively, and the mobility is detected by SDS-PAGE.

Amino acid analysis for determining extinction coefficients is done using Amino Quant 1090 HPLC system from Hewlett Packard. Microwave facilitated vapor phase hydrolysis of lyophilized samples is done using the MDS-2000 hydrolysis-station(CEM, Matthews, N.C.). 6N HCl containing 1% phenol as a scavenger is used to create the acid vapors. Hydrolysis time is 20 minutes at 70 psi (~148° C.). Hydrolyzed samples are lyophilized and redissolved in 20 μl of 500 pmol/μl sarcosine and norvaline as internal standards. 1 μl is injected and analyzed according to manufacturer's instructions.

B. RESULTS AND DISCUSSION

1. Purification

The previously characterized *P. pinsitus* laccase has a pI of ~3.5. However, considerable laccase activity is detected in the run-through fraction of Q-Sepharose pre-equilibrated at pH 7.7. Upon a gradient elution, one more active fraction comes off the column before the active fraction initially anticipated. UV-visible spectra and SDS-PAGE show that all three fractions contain mainly laccase. After further purification by gel filtration, different pI's under native non-denaturing conditions are detected for the two new fractions and shown to be consistent with the elution order.

2. Characterization

The pure laccase preparations derived from Q-Sepharose eluates behave as a rather well-defined band on SDS-PAGE at ~63 kDa. Deglycosylation detects ~14% w/w carbohydrates based on mobility change on SDS-PAGE. On native-IEF, the laccase preparations have bands of pI 6–6.5, 5–6.5, and 3.5. ABTS-agarose overlay show that all bands are active. Each form in turn shows multiple isoforms under the IEF conditions.

The neutral and acidic forms have a typical UV-visible spectrum with maxima at 605 and 275 nm. The ratio of $A_{275}/A_{605}$ is 30–40. The spectrum for the acidic-neutral form has a peak at 276 nm and a shoulder around 600 nm.

The N-terminal sequencing shows that the neutral and neutral-acidic forms have the same first 29 residues (Table 1). The N-terminus of the acidic form matches 100% to that of the previously characterized form. All three forms exhibit comparable cross-reactivity toward antibodies raised against previously characterized form.

TABLE 1

Structural and enzymatic properties of *P. pinsitus* laccases

| Form | N-terminus | LACU | $\Delta A_{405}$min-1 (ABTS) |
|---|---|---|---|
| Acidic | GIGPVA D LTTTNAAVSPDGFSRQAVVVNG | 92 | 4000 |
| Acidic-Neutral | A*****(*)*VVAp****L*D*I**** | 75 | 4000 |
| Neutral | A*****(*)*VVAp****L*D*I**** | 32 | 1000 |

*: Same residue as compared with the acidic form.
(): weak signal

3. Laccase Activity

The specific activities (per $A_{275}$) of the three forms are tested by both ABTS and syringaldazine oxidations. The shapes and optima of the pH activity profiles for the three forms are very close: all have optima at ≦pH4 and pH 5–5.5 for ABTS and syringaldazine oxidations, respectively.

IV. ISOLATION OF MULTIPLE COPIES OF POLYPORUS PINSITUS LACCASE ENZYMES AND GENES

A. MATERIALS AND METHODS

1. Strains.

The following strains are employed in the methods described below: *E. coli* K802(e14-(mrca), mcrB, hsdR2, galK2, galT22, supE44, metB1; Clonetech); *E. coli* XL-1 Blue(recA1, endA1, gyrA96, thi-1, hsdR17, supE44, relA1, lac[F'proAB, lacIqZDM15, Tn10(tet$^r$)]; Stratagene) and *Polyporus pinsitus* CBS 678.70.

2. Genomic DNA isolation

Cultures of *P. pinsitus* are grown in 500 ml YG (0.5% yeast extract, 2% dextrose) at room temperature for 3 to 4 days. Mycelia are harvested through miracloth, washed twice with TE and frozen quickly in liquid nitrogen. The frozen mycelia are stored at −80° C. To isolate DNA, the mycelia are ground to a fine powder in an electric coffee grinder. The powdered mycelia are resuspended in TE to a final volume of 22 ml. Four ml 20% SDS is added with mixing by inversion followed by incubation at room temperature for 10 minutes. The sample is gently extracted with phenol:chloroform and centrifuged to separate the phases. The aqueous phase is collected and 400 µl proteinase A(10 mg/ml stock) is added. The sample is incubated at 37° C. for 30 minutes followed by a phenol:chloroform extraction. The aqueous phase is precipitated by the addition of 0.1 volumes of 3M Na acetate, pH 5.2 and 2.5 volumes 95% ethanol and freezing at 20° C. for one hour. After centrifugation to precipitate the DNA, the pellet is resuspended in 6 ml TE, and 200 µl boiled RNase A(10 mg.ml stock) is added. After incubation at 37° C., 100 µl proteinase A(10 mg/ml stock) is added followed by incubation at 37° C. for 30 minutes. The sample is phenol:chloroform extracted twice. To the aqueous phase, 0.1 volumes 3M Na acetate and 2.5 volumes are added, and the sample is frozen at −20° C. for 1 hour. Following centrifugation, the pellet is gently resuspended in 400 µl TE, and 40 µl Na acetate and 1 ml 95% ethanol are added. The DNA is pelleted by centrifugation, and the pellet is washed in 70% ethanol. The final pellet is resuspended in 250 µl TE.

3. RNA preparation

RNA is isolated from mycelia which are harvested from *P. pinisitus* cultures which are either induced for laccase expression by the addition of 2,5-xylidine or are uninduced. The mycelia are washed and frozen quickly in liquid N$_2$. Frozen mycelia are ground to a fine powder in an electric coffee grinder. The powder is immediately suspended in 20 ml extraction buffer (0.2M Tris-HCl, 0.25M NaCl, 50 mM EGTA, 0.8% tri-isopropyl naphthalene sulfonic acids, 4.8% p-aminosalicylic acid, pH 8.5). All solutions for RNA extraction are made with diethylpyrocarbonate (DEP)-treated water. The sample is kept on ice and 0.5 volumes TE-saturated phenol:chloroform is added. The sample is mixed well by inversion for 2 minutes, and the phases are separated by centrifugation. The aqueous phase is saved, and the organic phase is extracted with 2 ml extraction buffer and incubated at 68° C. for 5 minutes. After centrifugation to separate the phases, the aqueous phases are pooled and extracted several time with phenol:chloroform until there is no longer any protein at the interface. To the aqueous phase 0.1 volume 3M Na-acetate, pH 5.2 and 2.5 volumes 95% ethanol are added to precipitate the RNA, and the sample is frozen at −20° C. for 2 hours. The RNA is pelleted and resuspended in DEP water with RNase inhibitor.

4. DNA sequencing

Nucleotide sequences are determined using TAQ polymerase cycle sequencing with fluorescent-labeled nucleotides, and reactions are electrophoresed on an Applied Biosystems automatic DNA sequencer(Model 363A, version 1.2.0).

5. Preparation of genomic libraries

Two size-selected genomic libraries of *P. pinsitus* are constructed. A library of 5 to 6 kb BamHI fragments are constructed in pBluescript+. Genomic DNA is digested with BamHI, and the digest is electrophoresed on a preparative agarose(IBI) gel. The region containing the 5 to 6 BamHI fragments is sliced from the gel. The DNA is isolated from the gel using a Geneclean kit(BIO 101). The DNA is ligated into pBluescript plasmid previously digested with BamHI and dephosphorylated with BAP(GIBCO BRL), *E. coli* XL-1 Blue competent cells (Stratagene) are transformed with the ligation, and 12,000 white colonies are obtained.

A library of 7 to 8 kb BamHI/EcoRI fragments is constructed in pUC118. Ten µg genomic DNA is digested with BamHI and EcoRI and treated with BAP(GIBCO BRL). Competent *E. coli* XL-1 Blue cells are transformed with the ligation, and the library contains ~8000 recombinants.

For the preparation of a total genomic library in lambda EMBL4, 25 µg of *P. pinsitus* genomic DNA is partially digested with Sau3A. After digestion, the DNA is electrophoresed on a preparative low-melt agarose gel, and a band containing the 9 to 23 kb sized DNA is sliced from the gel. The DNA is extracted from the gel using β-agarose(New England Biolabs). The isolated EMBL4 arms (Clonetech) according to the supplier's directions. The ligation is packaged in vitro using a Gigapack II kit(Stratagene). The library is titered using *E. coli* K802 cells. The unamplified library is estimated to contain 35,000 independent recombinants. The library is amplified using *E. coli* K802 cells.

6. Southern and Northern Blots

DNA samples are electrophoresed on agarose gels in TAE buffer using standard protocols. RNA samples are electrophoresed on agarose gels containing formaldehyde. Both DNA and RNA gels are transferred to Zeta-Probe membrane (BIO-RAD) using either capillary action under alkaline conditions or a vacuum blotter. After transfer, the DNA gels are UV crosslinked. Blots are prehybridized at 65° C. in 1.5× SSPE, 1% SDS, 0.5% non-fat dried milk and 200 µg/ml salmon sperm DNA for 1 hour. Radioactive probes are added directly to the prehybridization solutions, and hybridizations are continued overnight at 65° C. Blots are washed with 2× SSC for 5 minutes at 65° C. and with 0.2× SSC, 1%SDS, 0.1% Na-pyrophosphate at 65° C. for 30 minutes twice.

Radioactive labeled probes are prepared using a α-$^{32}$p-dCTP and a nick translation kit(GIBCO-BRL).

7. Library screening

For screening of the size-selected 5–6 kb BamHI and 7–8 kb BamHI/EcoRI libraries ~500 colonies on LB carb plates and lifted the colonies to Hybond N$^+$ filters (Amersham) using standard procedures. The filters are UV crosslinked following neutralization. The filters are prehybridized at 65° C. in 1.5× SSPE, 1% SDS, 0.5% non-fat dried milk, 200 µg/ml salmon sperm DNA for 1 hour. Nick-translated probes are added directly to the prehybridization solution, and hybridizations are done overnight at 65° C.

For screening of the genomic bank in EMBL, appropriate dilutions of the amplified library are plated with *E. coli* K802 cells on 100 mM NZY top agarose. The plaques are lifted to Hybond N$^+$ membranes (Amersham) using standard procedures. The DNA is crosslinked to the membranes using UV crosslinking. The filters are prehybridized and hybridized using the same conditions as those mentioned above.

RESULTS AND DISCUSSION

1. Isolation of multiple copies of laccase gene

*P. pinisitus* genomic DNA is digested with several different restriction enzymes for southern analysis. The blot is probed with the cDNA insert (isolated as a BamHI/SphI fragment from the pYES vector) which is labeled with $\alpha$-P$^{32}$-dCTP. The blot is hybridized and washed as described above. The cDNA hybridizes to several restriction fragments for most of the enzymes suggesting that there are multiple laccase genes in the genome. Because the cDNA hybridizes to a BamHI fragment of ~5.5 kb, a library of 5–6 kb BamHI fragments from *P. pinisitus* is constructed.

2. Screening of Genomic Libraries

The results from screening of the libraries are summarized in Table 2. The 5–6 kb BamHI size-selected library is screened with the original cDNA clone labeled with $^{32}$P. Approximately 30,000 colonies are screened with hybridizations done at 65° C. Plasmid DNA is isolated from two positive colonies and digested with BamHI to check for insert size. Both clones contain an ~5.5 kb BamHI insert. The cloned insert(LCC3) is sequenced from either end; the sequence has homology to the cDNA, but is clearly not the cDNA encoded laccase. The partial DNA sequence of LCC3 also indicates that the LCC3 pUC118 clone does not contain the full gene.

From a southern blot of BamHI/EcoRI double digested DNA it is demonstrated that the cDNA hybridizes to an ~7.7 kb fragment. A size-selected library in pUC118 is constructed containing 7–8 BamHI/EcoRI fragments. A total of ~8000 independent colonies are obtained and screened by hybridization with a $^{32}$P labeled insert. Plasmid DNA is isolated from the positive colonies and digested with BamHI and EcoRI. Restriction analysis of the plasmids demonstrate that they fall into two classes. One class (LCC4) contains four clones which are all identical and have an ~7.7 kb BamHI/EcoRI insert which hybridizes to the cDNA. A second class(LCC1) contains two clones which are identical and have inserts of ~7.2 kb which hybridize to the cDNA. Partial DNA sequencing of clones LCC1 and LCC4 demonstrate that clone 21 is the genomic clone of the original cDNA, while LCC4 codes for another laccase. The partial DNA sequence of LCC1 shows that the pUC118 clone does not contain the full gene and that a fragment upstream of the EcoRI site is needed.

At the same time the size selected 7–8 BamHI/ECoRI library is being constructed, a *P. pinisitus* genomic bank in EMBL4 is constructed containing ~35,000 independent recombinant phage. Ten positive plaques are picked and purified. DNA is isolated from the purified phage lysates. Restriction digests of EMBL DNAs demonstrates than there are three classes of clones. The first class(11GEN) is defined by two sibs whose inserts contain a BamHI/EcoRI fragment of the same size as LCC1 which hybridizes to the LCC1 insert. The second class (12GEN) contains one clone which has a different restriction pattern than the 11GEN class and whose insert contains a different restriction pattern than the 11GEN class and whose insert contains an ~5.7 kb BamHI/EcoRI fragment. The third class is defined by a single clone whose insert contains an ~3.2 kb BamHI/EcoRI fragment which hybridizes to the LCC1 insert. DNA sequence analysis demonstrates that clone 11GEN contains the LCC1 BamHI/EcoRI fragment and both 5' and 3" flanking regions. It is also demonstrated that clone 12GEN contains a portion of the LCC1 insert.

The *P. pinisitus* EMBL genomic bank is also screened with the LCC3 BamHI insert in order to clone the full gene. Approximately 30,000 plaques are plated and lifted from hybridization. Five plaques which hybridize to the LCC3 (BamHI/EcoRI) insert are identified and purified. DNA is isolated from the purified phage stocks. Southern analysis of *P. pinisitus* genomic DNA demonstrates that the LCC3 BAmHI insert hybridizes to an ~7 kb EcoRI fragment. Restriction digests and southerns demonstrate that 4 of the clones contain restriction fragments which hybridize to the EcoRI/BamHI (1.6 kb) fragment and that the clones fall into three classes. Class one is defined by a single clone (LCC5) whose insert contains a 3 kb EcoRI fragment which hybridizes to the LCC3 BamHI/EcoRI fragment. Another class is defined by clone (LCC2) whose insert contains an ~11 kb EcoRI fragment which hybridizes to the LCC3 BamHI/EcoRI insert. The third class is defined by two clones which are not identical but contain many of the same restriction fragments; these clones both contain an ~7.5 kb EcoRI fragment which hybridizes to the LCC3 insert. Further analysis of this third class indicates that they are identical to clone LCC4. Partial DNA sequencing of LCC5 and LCC2 indicates that both of these clones code for laccases; however, neither is identical to any of the above mentioned laccase genes (LCC1, LCC3, or LCC4). At this point, five unique laccase genes are cloned; however, the fragments subcloned from LCC5 and LCC2 do not contain the full genes.

From the DNA sequencing of the 3 kb EcoRI fragment from clone LCC5 it is determined that ~200 base pairs of the N-terminus are upstream of the ECoRI site. A 380 bp EcoRI/MluI fragment from LCC5 is used to identify for subcloning a MluI fragment from the LCC5 EMBL clone. An ~4.5 MluI fragment from the LCC5 EMBL clone is subcloned for sequencing and shown to contain the N-terminal sequence.

To clone the N-terminal half of the LCC3 laccase gene, the *P. pinisitus* EMBL genomic bank is probed with an ~750 bp BamHI/StuI restriction fragment from the LCC3 pUC118 clone. Approximately 25,000 plaques are screened and five plaques appear to hybridize with the probe. Upon further purification only three of the clones are still positive. Two of the clones give very strong signals and the restrictions digests of DNA isolated from these phage demonstrate that both contain an ~750 bp BamHI/StuI fragment in their inserts and that the two clones are not identical but overlapped. Based on results of Southern analysis, an ~8.5 kb fragment from these clones are subcloned for sequencing. The EcoRI fragment is shown to contain the entire gene.

To clone the N-terminal half of the LCC2 laccase gene, the *P. pinisitus* genomic bank in EMBL4 is probed with an ~680 bp EcoRI/PvuI of the EMBL LCC2 clone. Thirty thousand plaques are screened by hybridization at 65° C., and 15 plaques appear to hybridize with the probe. All fifteen are purified, and DNA is isolated. The clones can be placed in four classes based on restriction patterns. Seven of the clones are all sibs, and are identical to the original EMBL clone of LCC2. The second class is defined by 3 clones which are sibs. An ~4 kb HindIII fragment is subcloned from this class for sequencing and is shown to contain the N-terminal half of LCC2. A third class is defined by a single clone and is not characterized further.

3. DNA sequencing

The complete DNA sequences of the five genomic clones is determined as described in Materials and Methods. Sequencing of clone LCC2 demonstrate that it probably codes for the second form of laccase (neutral pI) isolated from culture broth from an induced *P. pinisitus* culture as described above. The N-terminal protein sequence from the neutral pI laccase and the predicted N-terminus for the protein coded for by LCC2 are compared, and show identity. The predicted pI for the protein coded for by clone LCC2 is 5.95, which is in good agreement with the experimental pI determined for the second form of laccase being between 5.0 and 6.5. FIGS. 1–5 (SEQ ID NOS. 1–5) show the DNA sequences and predicted translation products for the genomic clones. For LCC1, the N-terminus of the mature protein as determined by protein sequencing and predicted by Von Heijne rules is Gly at position 22. The N-terminus is Gly-Ile-Gly-Pro-Val-Ala-. For LCC2 the N-terminal amino acid of the mature protein as determined by protein sequencing is Ala at position 21. The N-terminus is Ala-Ile-Gly-Pro-Val-Ala-. For LCC3 the predicted N-terminal amino acid of the mature protein is Ser at position 22, with the N terminus being Ser-Ile-Gly-Pro-Val-Thr-Glu-Leu-. For LCC4, the predicted N-terminal amino acid is Ala at position 23 with the N-terminus being Ala-Ile-Gly-Pro-Val-Thr-. For LCC5 the predicted N-terminal amino acid is Ala at position 24 with the N-terminus being Ala-Ile-Gly-Pro-Val-Thr-Asp. A comparison of the structural organization of the genes and the predicted proteins they code for is presented in Table 1. It will be seen that the five genes have different structural organizations and code for proteins of slightly different sizes. Comparisons between the predicted proteins of the genomic clones and other fungal laccase are also done. Table 2 shows a comparison of the predicted laccase to each other and to other fungal laccases. Clone LCC1(the induced laccase first characterized) has the most identity(90%) to the *Coriolus hirsutus* laccase and the PM1 basidiomycete laccase (Coll et al., supra). The other four laccases have between 64 and 80% identity to the *C. hirsutus* laccase. The laccase coded for by LCC3 has the least identity to the LCC1 laccase and the other fungal laccases shown in Table 2. LCC2 appears to be the second wild-type laccase isolated as described above; based on the N-terminal sequences of the isolated clones, it also appears that the "neutral" and acidic neutral" wild-type laccases are the same enzyme which is encoded by the LCC2 sequence.

TABLE 1

Comparison of Structural Organization and Predicted Proteins of the *P. pinsitis* Genomic Clones.

| Gene | # Introns | Size of Predicted Precursor Protein | Size of Predicted Mature Protein | Predicted Isolelectric Point |
|---|---|---|---|---|
| 21GEN | 8 | 520 | 499 | 4.49 |
| 23GEN | 10 | 519 | 498 | 5.95 |
| 24GEN | 12 | 516 | 495 | 5.23 |
| 31GEN | 11 | 510 | 488 | 4.06 |
| 41GEN | 11 | 527 | 504 | 4.07 |

TABLE 2

Amino Acid Identity Between *P. pinsitis* Laccases and Other Fungal Laccases.

| | 21GEN | 23GEN | 24GEN | 31GEN | 41GEN | CRIPHA | CRIPHE | PBILAC | PM1 |
|---|---|---|---|---|---|---|---|---|---|
| 21GEN | — | 79% | 64% | 70% | 72% | 90% | 91% | 64% | 80% |
| 23GEN | 79% | — | 65% | 66% | 69% | 80% | 81% | 62% | 74% |
| 24GEN | 64% | 65% | — | 61% | 65% | 64% | 65% | 61% | 63% |
| 31GEN | 70% | 66% | 61% | — | 75% | 69% | 70% | 64% | 69% |
| 41GEN | 72% | 69% | 65% | 75% | — | 71% | 72% | 64% | 71% |
| CRIPHA | 90% | 80% | 64% | 69% | 71% | — | 99% | 64% | 80% |
| CRIPHE | 91% | 81% | 65% | 70% | 72% | 99% | — | 65% | 81% |
| PBILAC | 64% | 62% | 61% | 64% | 64% | 64% | 65% | — | 65% |
| PM1 | 80% | 74% | 63% | 69% | 71% | 80% | 81% | 65% | — |

21GEN, 23GEN, 24GEN, 31GEN and 41GEN = *P. pinsitis* laccase clones
CRIPHA = *Coriolus hirsutis* laccase A
CRIPHE = *C. hirsutis* laccase B
PBILAC = *Phlebia radiata* laccase
PM1 = Basidiomycete PM1 laccase (CECT2971)

5. Northern blots

RNA is isolated from mycelia from both a xylidine-induced culture and an uninduced culture. RNA is blotted to membrane after electrophoresis, and the blot is probed with the cDNA insert, or a small fragment containing ~100 bp of the 23GEN promoter and the first 100 bp of the coding region. A transcript of about 1.8 kb hybridizes to both the induced and uninduced RNA samples; however, transcription of this message is clearly induced by the addition of xylidine to the culture.

III. EXPRESSION OF *P. PINSITUS* LACCASE IN ASPERGILLUS

MATERIALS AND METHODS
1. Strains

*A. oryzae* A1560, *A. oryzae* HowB104 (fungamyl delete, pyrg),*A. oryzae* HowB101pyrg, *A. niger* Bo-1, *A. niger* Bo-80, *A. niger* ATCC1040, *A. niger* NRRL337, *A. niger* NRRL326, *A. niger* NRRL326, *A. niger* NRRL2295, *A. niger* ATCC11358, *A. niger* NRRL322, *A. niger* AT10864, *A. japonicus* A1438, *A. phoenicis*, *A. foetidus* N953.

2. Media

For the shake flask cultivation of the *A. niger*, *A. foetidus*, and *A. phoenicis* MY50 (per liter:50 g maltodextrin, 2 g MgSO$_4$, 10 g KH$_2$PO$_4$, 2 g K$_2$SO$_4$, 2 g citric acid, 10 g yeast extract, 0.5 ml trace metals, 2 g urea, pH 6.0) media is used. For the shake flask cultivation of the *A. oryzae* A1560 and HowB101 strains MY51 (per liter: 30 g maltodextrin, 2 mg MgSO$_4$, 10 g KH$_2$PO$_4$, 2 g K$_2$SO$_4$, 2 g citric acid, 10 g yeast extract, 0.5 ml trace metals, 1 g urea, 2 g(NH$_4$)$_2$SO$_4$, pH 6.0) is used. For the shake flask analysis of the *A.oryzae* HowB104 strains, MY51 maltose(same as MY51 but with 50 g of maltose instead of maltodextrin) media is used. For the shake flask analysis of the *A. japonicus* strains M400 media (per liter: 50 g maltodextrin, 2 g MgSO$_4$, 2 g KH$_2$PO$_4$, 4 g citric acid, 8 g yeast extract, 0.5 ml trace metals, 2 g urea, pH 6.0.

Cultures grown overnight for protoplast formation and subsequent transformation are grown in YEG (0.5% yeast extract, 2% dextrose). For strains that are pyrg, uridine is supplemented to 10 mM final concentration.

3. Screening for laccase production

Primary transformants are screened first on a minimal medium plates containing 1% glucose as the carbon source and 1 mM ABTS to test for production of laccase. Transformants that give green zones on the plates are picked and spore purified before shake flask analysis is done.

Shake flask samples are centrifuged to clear the broth. Dilute or undiluted broth samples are assayed with ABTS

RESULTS AND DISCUSSION

1. Expression in shake flasks

Figure 7:
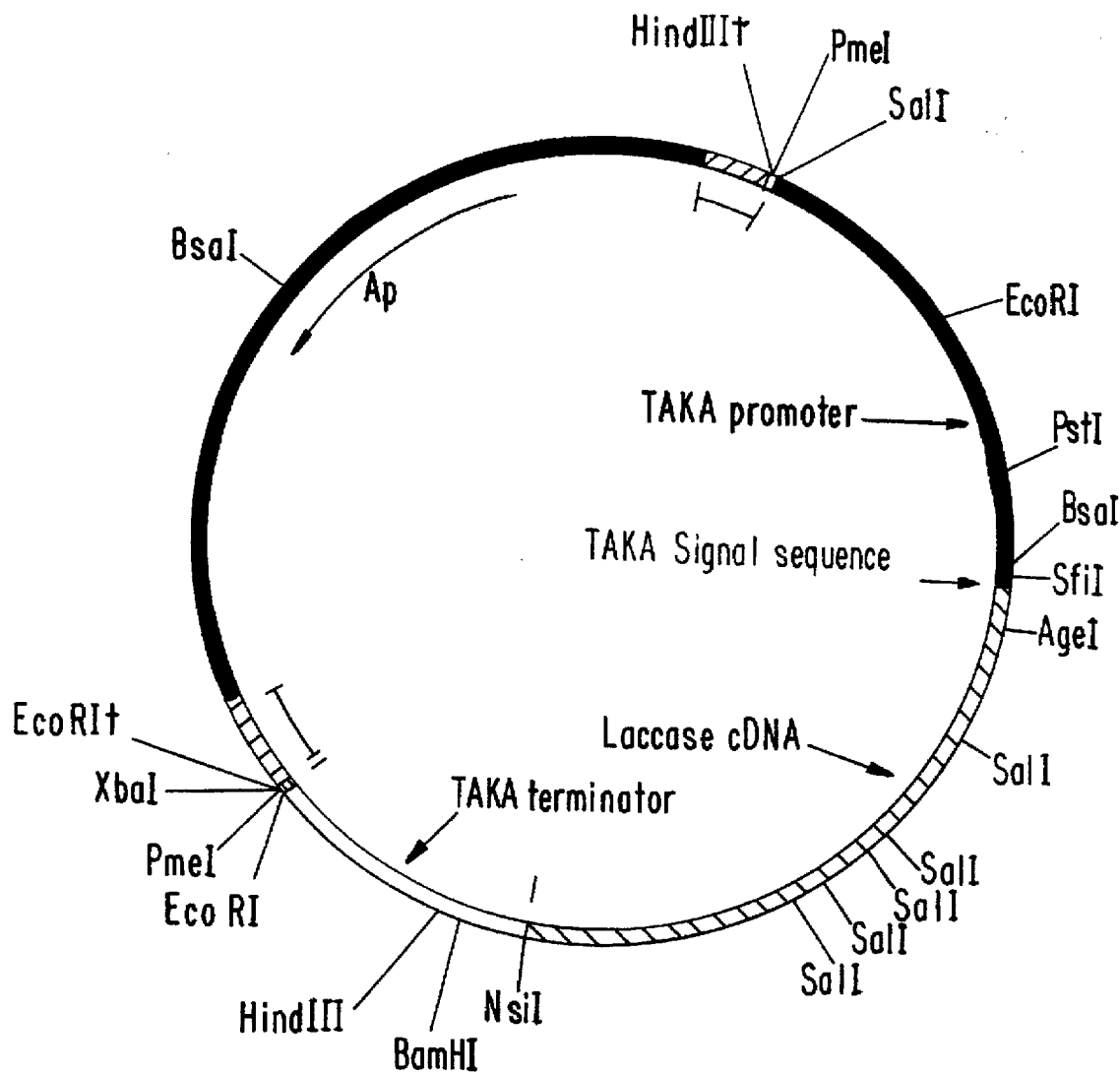
FIG. 7 shows the structure of vector pDSY1

The first expression vector constructed is pDSY1, which contains the TAKA promoter, TAKA signal sequence, *P. pinisitus* laccase cDNA beginning at the mature N-terminus and the AMG terminator. The TAKA signal sequence: laccase insert is constructed in 2 steps. First by site directed mutagenesis, an AgeI site beginning at bp 107 of the laccase mature coding region is created by a single base change and a NsiI site is created ~120 bp downstream of the laccase stop codon(ACG GGT->ACC GGT and TTC GCT->ATG CAT, respectively). A small PCR fragment beginning with an SfiI site and ending with the AgeI site at 107 bp in laccase is PCR amplified. This fragment contains a piece of the TAKA signal sequence and the first ~107 bp of the mature laccase cDNA. Further DNA sequencing of this fragment shows it has a single base change that leads to a substitution of Asn for Thr at position 9 in mature laccase. This substitution creates a potential N-linked glycosylation site. The PCR fragment and AgeI/NsiI fragments are cloned into pMWR1 (FIG. 6) which has been digested with SfiI/NsiI. The vector pMWR1 contains the TAKA promoter, a portion of the TAKA signal sequence which ends with an SfiI site, and the TAKA terminator with a NsiI site inserted directly 5' to the terminator. The resulting expression vector (FIG. 7) is used to cotransform several hosts. Methods for cotransformation of Aspergillus strains are as described in Christensen et al., supra.

In the second laccase expression vector, the base change in DSY1 which leads to the substitution of Asn for Thr at amino acid 9 is reverted back to wild type by a PCR reaction. The second expression vector pDSY2 is identical to pDSY1 except for this single base change. Three different *A. oryzae* strains and several *A. niger* strains are cotransformed With pDSY2 and either pTOC90 (WO 91/17243) which carries the *A. nidulans* amdS gene or pSO2 which carries the *A. oryzae* pyrG gene.

Expression of laccase is observed in all hosts tested, with both DSY1 and DSY2. Yields range from 0.1–12.0 Δabs/ min/ml, with highest yields being observed with *A. niger* strains.

Figure 8:
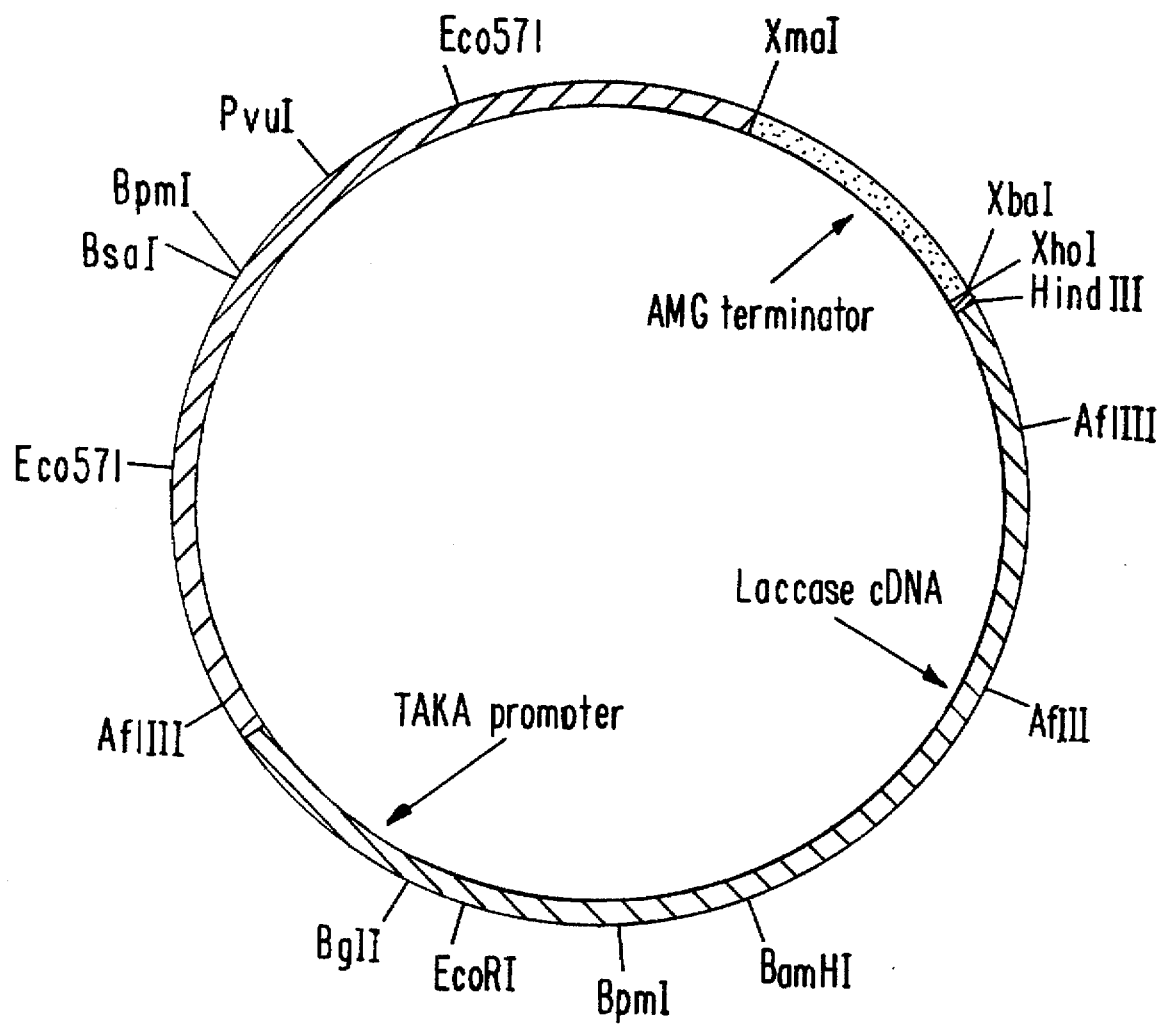
FIG. 8 shows the structure of vector pDSY10

A construct pDSY10 is made which contains the TAKA promoter, laccase full-length cDNA including its own signal sequence and the AMG terminator. A 200 bp BamHI/AgeI fragment which has a BamHI site immediately 5' to the ATG of the initiation codon and an AgeI site at the same position as in pDSY1 is PCR amplified using lacI as template. A MluI/HindIII fragment is PCR amplified using pDSY2 as template and begins with the MluI site present in the cDNA and ends with a HindII site directly 3' to the stop codon of laccase. The above two fragments and the AgeI/MluI fragment from pDSY2 are ligated into pHD414 to yield pDSY10 (FIG. 8).

The vector pHD414 used in expression of laccase is a derivative of the plasmid p775 (EP 238 023). In contrast to this plasmid, pHD414 has a string of unique restriction sites between the TAKA promoter and the AMG terminator. The plasmid is constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region is removed by cleavage with NarI (positioned in the pUC vector) and XbaI (just 3' to the terminator), subsequent filling in the generated ends with Klenow DNA polymerase+ dNTP, purification of the vector fragment on a gel and religation of the vector fragment. This plasmid is called pHD413. pHD413 is cut with StuI (positioned in the 5' end of the promoter) and PvuII (in the pUC vector), fractionated on gel and religated, resulting in pHD414. Cotransformation of *A. oryzae* HowB104 and *A. niger* Bo-1 are done using pToC90 for selection. Yields in shake flask are comparable to those seen with pDSY2.

2. Expression in fermentors

A 1 ml aliquot of a spore suspension of *Aspergillus niger* transformant Bo-1-pDSY10-4 (approximately 10$^9$ spores/ ml) is added aseptically to a 500 ml shake flask containing 100 ml of sterile shake flask medium (glucose, 75 g/l ; soya meal, 20 g/l; MgSO$_4$.7H$_2$O, 2 g/l; KH$_2$PO$_4$, 10 g/l; K$_2$SO$_4$, 2g/l; CaCl$_2$.2H$_2$O 0.5 g/l; Citric acid, 2 g/l; yeast extract, 10 g/l; trace metals[ZnSO$_4$.7H$_2$O, 14.3 g/l; CUSO$_4$.5H$_2$O, 2.5 g/l; NiCl$_2$.6H$_2$O, 0.5. g/l; FeSO$_4$.7H$_2$O, 13.8 g/l, MnSO$_4$.H$_2$O, 8.5 g/l; citric acid, 3.0 g/l], 0.5 ml/l ; urea, 2 g/l, made with tap water and adjusted to pH 6.0 before autoclaving), and incubated at 37° C. on a rotary shaker at 200 rpm for 18 hours. 50 ml of this culture is aseptically transferred to a 3 liter fermentor containing 1.8 liters of the fermentor media (maltodextrin MD01 300 g/l; MgSO$_4$.7H$_2$O, 2 g/l; KH$_2$PO$_{4, 2}$ g/l; citric acid 2 g/l; K$_2$SO$_4$, 2.7 g/l; CaCl$_2$.2H$_2$O, 2 g/l; trace metals, 0.5 ml/l; pluronic antifoam, 1 ml/l; made with tap water and pH adjusted to 6.0 before autoclaving). The fermentor temperature is maintained at 34° C. by the circulation of cooling water through the fermentor jacket. Sterile air is sparged through the fermentor at a rate of 1.8 liter/min (1 v/v/m). The agitation rate is maintained at 800 rpm for the first 24 hours after inoculation and at 1300 rpm for the remainder of the fermentation. The DH of the fermentation is kept at 4.0 by the automatic addition of 5N NaOH or H$_3$PO$_4$. Sterile feed (urea, 50 g/l; pluronic antifoam, 1.5 ml/l; made up with distilled water and autoclaved) is added to the fermentor by use of a peristaltic pump. The feed rate profile during the fermentation is as follows: 40 g of feed is added initially before inoculation; after inoculation, feed is at a constant rate of 2.5 g/l h.

Copper is made as a 400× stock in water or a suitable buffer, filter sterilized and added aseptically to the tank to a final level of 0.5 mM. Samples for enzyme activity determination are withdrawn and filtered through Miracloth to remove mycelia. These samples are assayed for laccase activity by a LACU assay. Laccase activity is found to increase continuously during the course of the fermentation, with a value of approximately 55 LACU/ml is achieved after 190 hours. This corresponds to approximately 350 mg/l of recombinant laccase expressed.

IV. PURIFICATION OF RECOMBINANT LACCASE

MATERIALS AND METHODS

1. Materials.

Chemicals used as buffers and substrates are commercial products of at least reagent grade. Endo/N-glycosidase G is from Boehringer-Mannheim. Chromatography is performed on either a Pharmacia's FPLC or a conventional open column low pressure system. Spectroscopic assays are conducted on a Shimadzu PC160 spectrophotometer.

2. Purification (a) DSY2

2.8 liters cheese-cloth filtered broth (pH 7, 19 mS) obtained from an *A. oryzae* pDSY2 transformant as described above is filtered on 0.45 μ Corning filter and concentrated on Spiral Concentrator (Amicon) with S1Y30 membrane to 200 ml. The concentrate pH is adjusted to 7.5, diluted with 4.8 l water to achieve 1.2 mS, and concentrated on SLY30 to 200 ml. 50 ml of this broth solution is applied onto a Q-Sepharose column (XK16, 34 ml gel), pre-equilibrated with 10 mM Tris, pH 7.5, 0.7 mS (Buffer A). The blue laccase band that migrates slowly during Loading is eluted by a linear gradient of Buffer B (Buffer A plus 0.5M NaCl). 24 ml of pooled laccase fractions are concentrated on Centricon-100 (Amicon) to 4.5 ml and applied onto a Superdex 200 column (HiLoad 16/60, 120 ml gel). During the development with Buffer C (Buffer A plus 0.15M NaCl, 14.4 mS), the blue laccase fractions elute followed by brownish contaminant fractions. Only the first half of the elution band(detected by $Abs_{600}$) show a high laccase to contaminant ratio and are pooled. The pooled fractions are dialyzed in 10 mM Bis-Tris, pH 6.8, 0.6 mS (Buffer D), applied onto a Mono-Q column (Mono-Q 5/5, 1 ml) equilibrated with Buffer D, and eluted with Buffer E (Bufer D plus 0.5M NaCl) using a linear gradient. The laccase fractions, which ome out round 27% Buffer E, are pure as judged by SDS-PAGE. At each step, the laccase fractions are routinely checked by ABTS oxidation, SDS-PAGE, and Western Blot.

(b) DSY10

2.8 liners cheese-cloth filtered broth(pH 7.3, 24 mS) obtained from HowB104-pDSYI10 is filtered on Whatman #2 paper and concentrated on Spiral Concentrator(Amicon) with SLY100 membrane to 210 ml. The concentrate pH is diluted with water to achieve 1.2 mS, and concentrated on SLY100 to 328 ml. This broth solution is applied onto a Q-Sepharose column (XK26, 120 ml gel), pre-equilibrated with 10 mM Tris, pH 7.5, 0.7 mS (Buffer A). The blue laccase band that migrates slowly during loading is eluted by a linear gradient of Buffer B (Buffer A plus 2M NaCl). 120 ml of pooled laccase fractions are diluted with water to achieve 1.1 mS and then concentrated on SIY100 to 294 ml and applied onto a Mono-Q column (HiLoad 16/10, 40 ml gel) pre-equilibrated with Buffer A. The laccase slowly passes through the column during loading and washing with Buffer A. The pooled fractions which have a pH reading of 5.6, are loaded on a Mono-Q column (HiLoad 16/10, 40 ml gel), pre-equilibrated with Buffer C (10 mM MES, pH 5.5, 0.1 mS). The laccase fractions elute by a very shallow gradient of Buffer D (Buffer C+1M NaCl). Enzymatic assays are conducted as described above.

3. Protein analysis

Total amino acid analysis, N-terminal sequencing, deglycosylation, SDS-PAGE, IEF, and Western blots are performed as decribed above.

B. RESULTS AND DISCUSSION

1. Purification and Characterization

Overall a 256-fold purification and a yield of 37% are achieved for DSY10, and a 246-fold purification and a yield of 14% are achieved for DSY2 In terms of electorphoretic pattern, spectral properties and activity, purified DSY2 and DSY10 are indistinguishable. Purified recombinant laccases behave as a dimer on gel filtration, and exhibit subunit molecular weight which is somewhat larger than that of the wild type laccase, indicating a post-translational processing in *A. oryzae* that results in the extra glycosylation on the recombinants. Deglycosylation has confirmed the difference in mass arising from extra sugars (Table 3).

TABLE 3

Molecular and spectral properties of recombinant and wild-type laccase

| | MW, kDa | | Carbohydrate | | |
|---|---|---|---|---|---|
| | Native | subunit | w/w % | pI | $\lambda_{max}$, nm (ε, l/g*cm) |
| WT | ~130 | ~63 | ~7 | 3.5 | 275 (1.8) 615 (0.12) |
| Rec. | ~130 | ~67 | ~13 | 3.5 | 275 (1.7) 615 (0.11) |

Figure 9A:
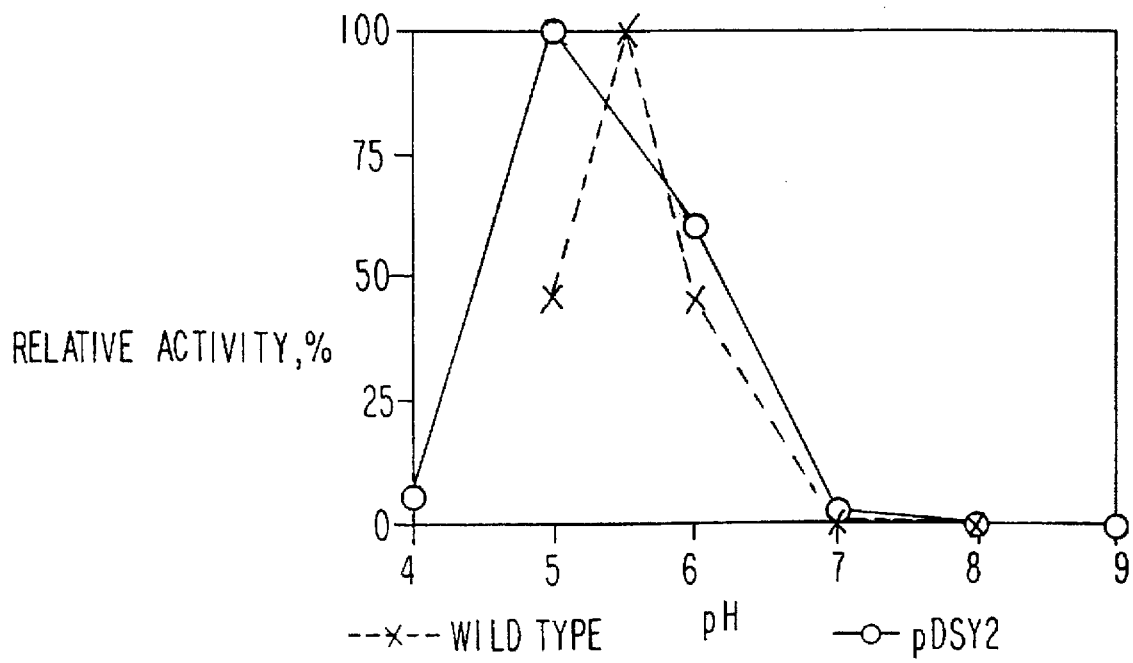
FIGS. 9A–9B show the pH profile of the laccase produced by pDSY2;(A) syringaldazine oxidation; (B) ABTS oxidation.
Figure 9B:
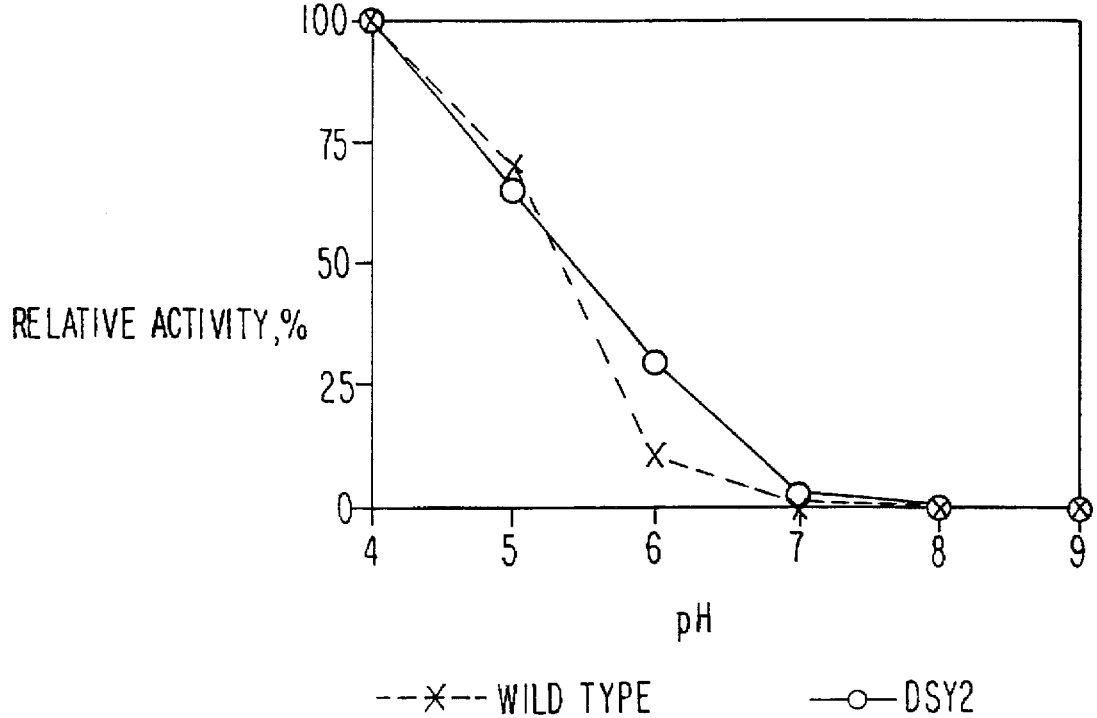

The spectra of the purified laccases have maxima of 615 nm and 275, with the ratio of absorbance at 275 nm to that at 615 nm being 16, indicating one Type I Cu per subunit. The ratio of absorbance at 330 nm to that at 615 nm is 1.0, close to the 0.75 value of *Rhus vernicefera* laccase, suggesting the presence of one Type II and two Type III copper ions per subunit. The extinction coefficient determined by amino acid analysis is 1.7/(g*cm), 3. Activity The laccase activity is measured by syringaldazine and ABTS oxidations. Expressed per $A_{275}$, the laccase has a value of 83 for LACU. Expressed per mg, it has a LACU of 141. The pH profile of the laccase is provided in FIG. 9.

V. USE OF POLYPORUS LACCASE TO DYE HAIR

The dyeing effect of *Polyporus pinsitus* laccase is tested and compared to the dyeing effect of 3% $H_2O_2$ on various dye precursors (listed below) and further on 0.1% p-phenylenediamine compared with a number of modifiers.

Materials:

Dye precursors:

0.1% p-phenylene-diamine in 0.1M K-phosphate buffer, pH 7.0. (pPD)
0.1% p-toluylene-diamine in 0.1M K-phosphate buffer, pH 7.0.
0.1% chloro-p-phenylenediamine in 0.1M K-phosphate buffer, pH 7.0.
0.1% p-aminophenol in 0.1M K-phosphate buffer, pH 7.0.
0.1% o-aminophenol in 0.1M K-phosphate buffer, DH 7.0.
0.1% 3,4-diaminotoluene in 0.1M K-phosphate, buffer pH 7.0.

Modifiers:

0.1% m-phenylene-diamine in 0.1M K-phosphate buffer, pH 7.0.
0.1% 2,4-diaminoanisole in 0.1M K-phosphate buffer, pH 7.0.
0.1% α-naphthol in 0.1M K-phosphate buffer, pH 7.0.
0.1% hydroquinone in 0.1M K-phosphate buffer, pH 7.0.
0.1% pyrocatechol in 0.1M K-phosphate buffer, pH 7.0.
0.1% resorcinol in 0.1M K-phosphate buffer, pH 7.0.
0.1% 4-chlororesorcinol in 0.1M K-phosphate buffer, pH 7.0.

When a modifier is used, the dye precursor p-phenylenediamine is combined with one of the above indicated modifiers so that the final concentration in the dyeing solution is 0.1% with respect to precursor and 0.1% with respect to modifier. The enzyme used is a recombinant laccase from *Polyporus pinisitus*, at a concentration of 10 LACU/ml.

Other solutions used in the process are 3% $H_2O_2$ (in the final dye solution), and a commercial shampoo. The quantitative color of the hair tresses is determined on a Datacolor Textflash 2000 (CIE-Lab) by the use of CIE-Lab parameters L* ("0"=black and "100"=white) combined with a* ("–"= green and "+"=reed). DL* and Da* are the delta values of L* and a*, respectively, of a sample when compared to L* and a* of untreated hair. The Light fastness is determined under a day light bulb (D65) at 1000 LUX.

Hair tresses of blond European hair (1 gram) are used. 4 ml dye precursor solution (including modifier)is mixed with 1 ml laccase or 1 ml $H_2O_2$ On a Whirley mixer, applied to the hair tresses and kept at 30° C. for 60 minutes. The hair tresses are then rinsed with running water, combed, and air dried.

Figure 10:
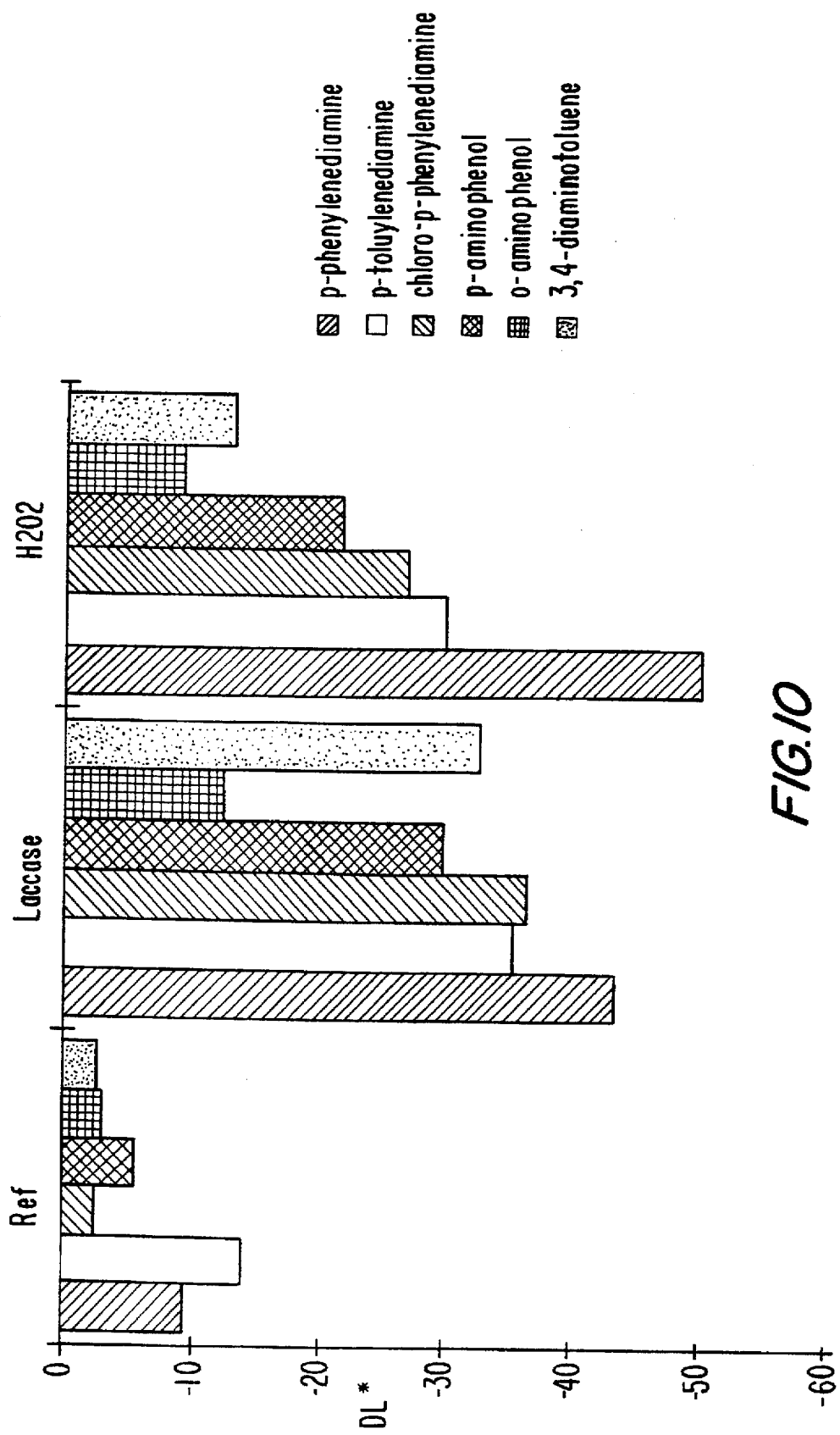
FIG. 10 illustrates a comparison of the use of laccase vs. $H_2O_2$, with various dye precursors, in hair dyeing, as a measurement of DL*.
Figure 11:
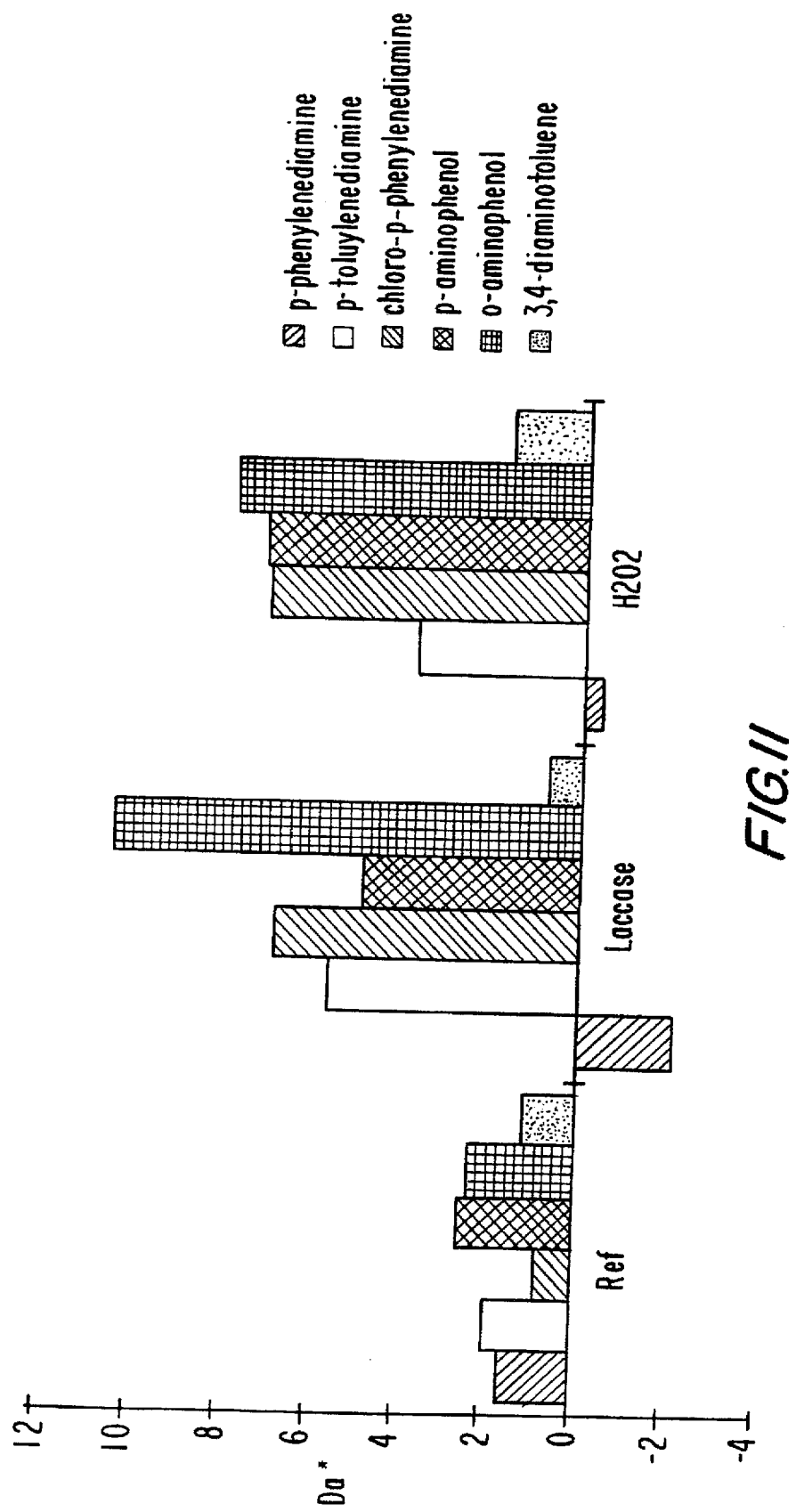
FIG. 11 illustrates a comparison of the use of laccase vs. $H_2O_2$, with various dye precursors, in hair dyeing, as a measurement of Da*.
Figure 12:
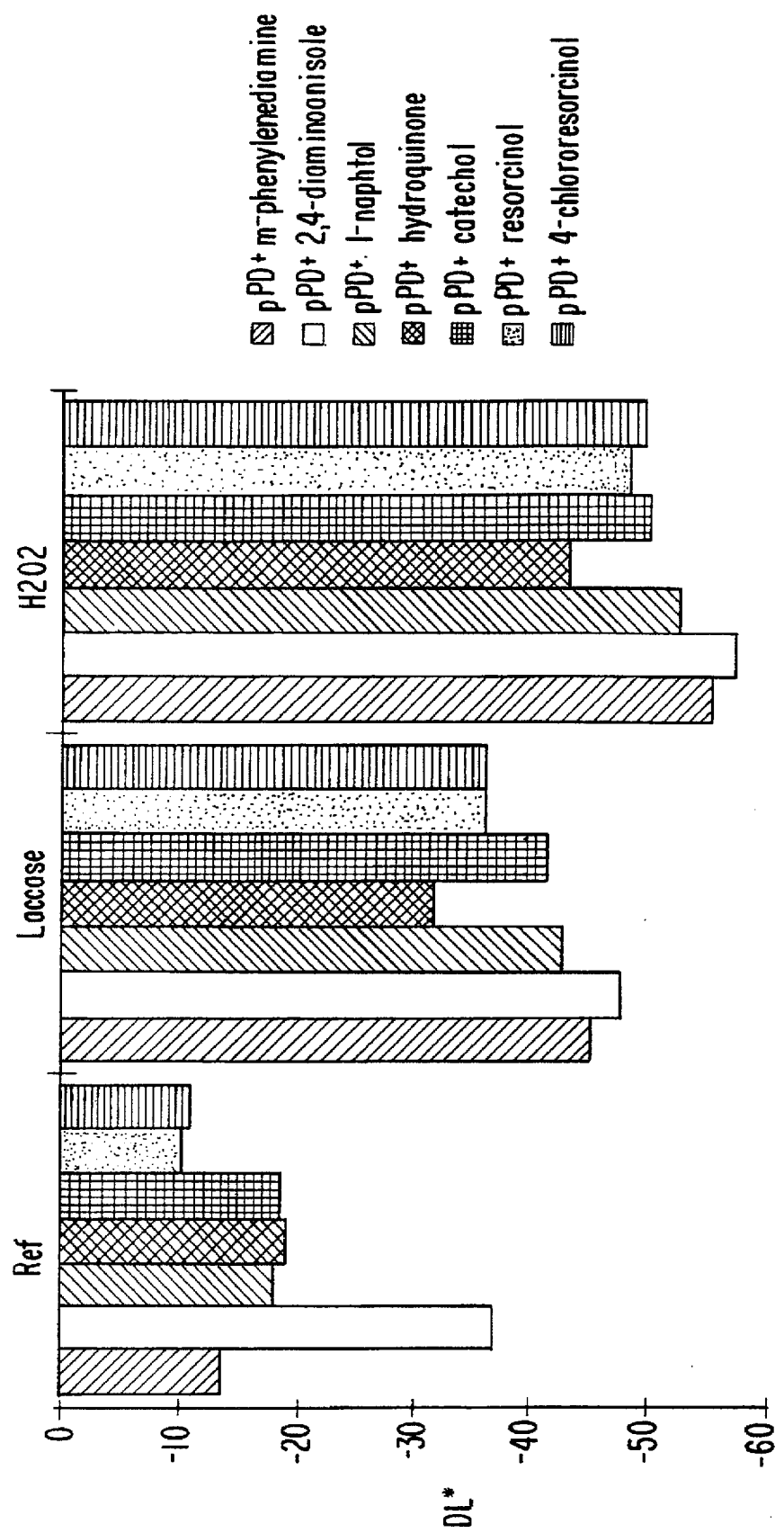
FIG. 12 illustrates a comparison of the use of laccase vs. $H_2O_2$, with various dye precursors and modifiers, in hair dyeing, as a measurement of DL*.

The results of the dyeing effect test are displayed below in Table 4–6 and further in the graphs in FIGS. 10 to 12.

TABLE 4

| Sample no. | Sample ID | L* | a* | DL* | Da* |
|---|---|---|---|---|---|
|  | Untreated blond hair | 72.25 | 2.42 |  |  |
| 1 | p-phenylenediamine (Reference) | 62.85 | 4.03 | –9.41 | 1,61 |
| 2 | p-phenylenediamine + Laccase | 28.70 | 0.33 | –43.56 | –2,10 |
| 3 | p-phenylenediamine + 3% $H_2O_2$ | 21.88 | 2.04 | –50.37 | –0,39 |
| 4 | p-Toluylenediamine (Reference) | 58.14 | 4.34 | –14.11 | 1.92 |
| 5 | p-Toluylenediamine + Laccase | 36.70 | 8.09 | –35.56 | 5.67 |
| 6 | p-Toluylenediamine + 3% $H_2O_2$ | 42.30 | 6.24 | –29.95 | 3.81 |
| 7 | chloro-p-phenylenediamine (Reference) | 69.82 | 3.23 | –2.43 | 0.81 |
| 8 | chloro-p-phenylenediamine + Laccase | 35.58 | 9.36 | –36.68 | 6.93 |
| 9 | chloro-p-phenylenediamine + 3% $H_2O_2$ | 45.42 | 9.59 | –26.84 | 7.17 |
| 10 | p-aminophenol (Reference) | 66.62 | 5.03 | –5.63 | 2.61 |
| 11 | p-aminophenol + Laccase | 42.42 | 7.38 | –29.84 | 4.95 |
| 12 | p-aminophenol + 3% $H_2O_2$ | 50.54 | 9.42 | –21.72 | 7.26 |
| 13 | o-aminophenol (Reference) | 69.39 | 4.82 | –2.89 | 2.39 |
| 14 | o-aminophenol + Laccase | 60.20 | 12.92 | –12.05 | 10.50 |
| 15 | o-aminophenol + 3% $H_2O_2$ | 63.49 | 10.38 | –8.77 | 7.96 |
| 16 | 3,4-diaminotoluene (Reference) | 69.62 | 3.57 | –2.63 | 1.15 |
| 17 | 3,4-diaminotoluene + Laccase | 39.51 | 3.15 | –32.74 | 0.73 |
| 18 | 3,4-diaminotoluene + 3% $H_2O_2$ | 59.32 | 4.16 | –12.94 | 1.74 |

L*: 0 = black, 100 = white
a*: – = green, + = red

TABLE 5

| Sample no. | Sample ID | L* | a* | DL* | Da* |
|---|---|---|---|---|---|
|  | Untreated blond hair | 72.25 | 2.42 |  |  |
| 19 | p-phenylenediamine, m-phenylenediamin (Reference) | 58.82 | 0.43 | –13,44 | –1,99 |
| 20 | p-phenylenediamine + m-phenylenedimin + Laccase | 27.20 | 0.83 | –45,05 | –1,59 |
| 21 | p-phenylenediamine + m-phenylenediamine + 3% $H_2O_2$ | 16.96 | 0.13 | –55,29 | –2,59 |
| 22 | p-phenylenediamine + 2,4-diaminoanisole (Reference) | 35.37 | –0.02 | –36,99 | –2,45 |
| 23 | p-phenylenediamine + 2,4-diaminoanisole + Laccase | 24.56 | 2.99 | –47,70 | –0,57 |
| 24 | p-phenylenediamine + 2,4-diaminoanisole + 3% $H_2O_2$ | 15.06 | 2.21 | –57,20 | –0,21 |
| 25 | p-phenylenediamine + α-naphthol (Reference) | 54.33 | 2.54 | –17,93 | 0,12 |
| 26 | p-phenylenediamine α-naphthol + Laccase | 29.53 | 4.03 | –42,72 | 1,60 |
| 27 | p-phenylenediamine + α-naphthol + 3% $H_2O_2$ | 19.58 | 3.90 | –52,68 | 1,47 |
| 28 | p-phenylenediamine + hydroquinone (Reference) | 53.25 | 4.08 | –19,01 | 1,65 |
| 29 | p-phenylenediamine + hydroquinone + Laccase | 40.48 | 5.00 | –31,77 | 2,58 |
| 30 | p-phenylenediamine + hydroquinone + 3% $H_2O_2$ | 29.06 | 4.96 | –43,20 | 2,53 |

L*: 0 = black, 100 = white
a*: – = green, + = red

TABLE 6

| Sample no. | Sample ID | L* | a* | DL* | Da* |
|---|---|---|---|---|---|
|  | Untreated blond hair | 72.25 | 2.42 |  |  |
| 31 | p-phenylenediamine + pyrocatechol (Reference) | 53.78 | 1.68 | –18.47 | –0.74 |
| 32 | p-phenylenediamine + pyrocatechol + Laccase | 30.77 | 2.64 | –41.49 | 0.22 |
| 33 | p-phenylenediamine + pyrocatechol + 3% $H_2O_2$ | 22.15 | 3.30 | –50.11 | 0.88 |
| 34 | p-phenylenediamine + resorcinol (Reference) | 62.12 | 4.23 | –10.14 | 1.81 |
| 35 | p-phenylenediamine + resorcinol + Laccase | 36.14 | 2.91 | –36.11 | 0.49 |
| 36 | p-phenylenediamine + resorcinol + 3% $H_2O_2$ | 23.94 | 3.16 | –48.31 | 0.74 |
| 40 | p-phenylenediamine + 4-chlororesorcinol (Reference) | 61.18 | 4.70 | –11.07 | 2.28 |
| 41 | p-phenylenediamine + 4-chlororesorcinol + Laccase | 36.00 | 2.76 | –36.26 | 0.34 |
| 42 | p-phenylenediamine + 4-chlororesorcinol + 3% $H_2O_2$ | 22.63 | 2.60 | –49.63 | 0.18 |

L*: 0 = black, 100 = white
a*: – = green, + = red

The above results demonstrate that the *Polyporus pinsitus* laccase can be used for oxidative dyeing of hair.

Tresses of blond european hair (1 gram)are used for testing the wash stability of hair dyed using *Polyporus pinsitus* laccase, compared with hair dyed using $H_2O_2$, and p-phenylene-diamine (pPD) as the dye precursor. Further the wash stability is compared with a commercial oxidative dye. The oxidative hair dyeing is carried out as described above, except that 50 LACU/ml *Polyporus pinsitus* laccase was used.

To test wash stability, the dyed hair tresses are wetted and washed for 15 seconds with 50 µl of commercial shampoo, and rinsed with water for 1 minute. The hair tresses are washed up to 20 times.

Figure 13:
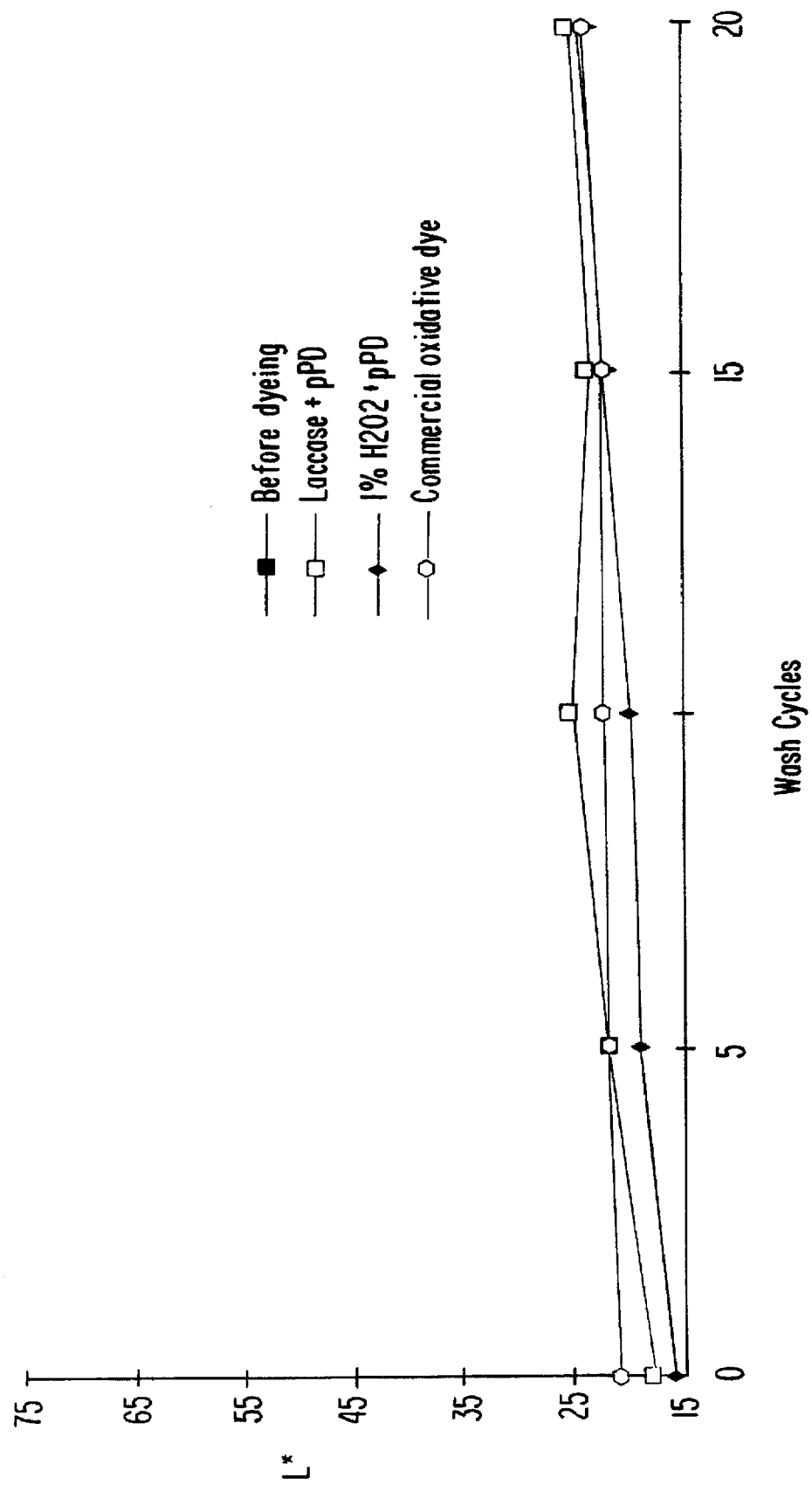
FIG. 13 illustrates a comparison of the wash stability of hair dyed with laccase vs. $H_2O_2$.

The results of the hair wash test are displayed in FIG. 13. It can be seen in FIG. 13 that the wash stability of hair washed up to 20 times is excellent, when using *Polyporus pinsitus* laccase for oxidative dyeing.

To test light fastness, tresses of blond european hair are used for testing the light fastness of hair dyed using *Polyporus pinsitus* laccase in comparison to hair dyed using $H_2O_2$. p-phenylene-diamine is the dye precursor. The dyeing of the hair is carried out as described above. One hair tress is kept dark, while an other is kept at day light (i.e. under a day light bulb (D65)), at approximately 1000 LUX) for up to 275 hours. The CIE-Lab-values are determined immediately after the dyeing of the hair, and further during exposure to day light.

Figure 14:
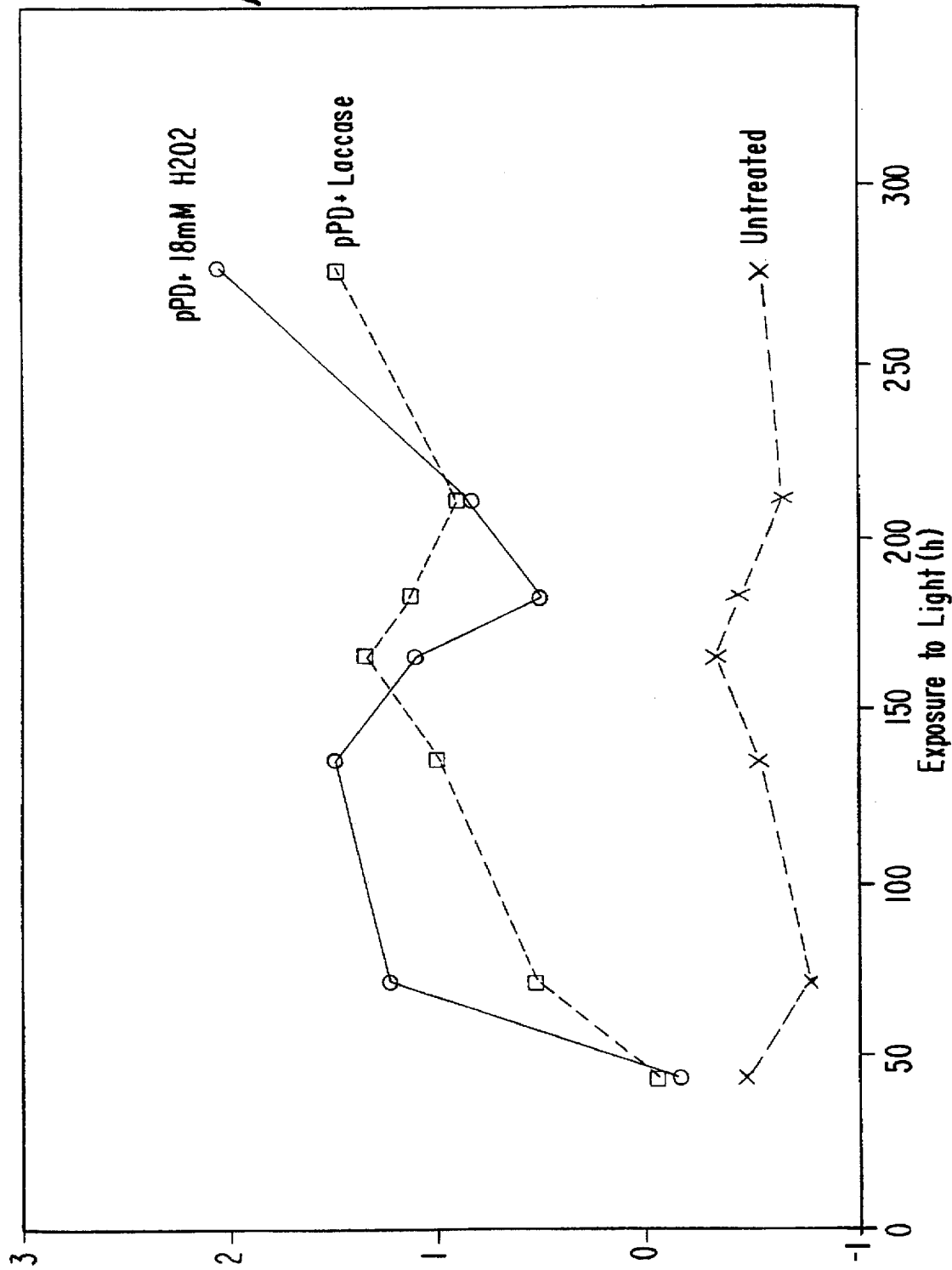
FIG. 14 illustrates the light fastness of hair dyed with laccase vs. $H_2O_2$.

The results of the test are displayed in FIG. 14. FIG. 14 shows that the hair dyed with p-phenylene-diamine using *Polyporus pinsitus* laccase has the same light fastness as hair dyed using $H_2O_2$.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604 on May 25, 1994 and given the following accession numbers.

| Deposit | Accession Number |
|---|---|
| *E. coli* DH5α containing pDSY22 (41GEN; an ~3.0 kb EcoRI insert) | NRRL B-21263 |
| *E. coli* DH5α containing pDSY23 (41GEN; an ~4.5 kb MluI insert; insert contains a small portion of the EcoRI fragment of pDSY22 and sequences 5' to the EcoRI fragment) | NRRL B-21268 |
| *E. coli* XL-1 Blue containing pDSY21 (31GEN; an ~7.7 kb EcoRI/BamHI insert) | NRRL B-21264 |
| *E. coli* XL-1 Blue containing pDSY18 (21GEN; an ~8.0 kb BamHI insert) | NRRL B-21265 |
| *E. coli* DH5α containing pDSY19 (23GEN; an ~4 kb HindIII insert) | NRRL B-21266 |
| *E. coli* DH5α containing pDSY20 (24GEN; an ~8.5 kb EcoRI insert) | NRRL B-21267 |

SEQUENCE LISTING461

( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 2418 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Polyporus pinsitus ( i x ) FEATURE:
        ( A ) NAME/KEY: intron
        ( B ) LOCATION: 414..464

( i x ) FEATURE:
        ( A ) NAME/KEY: intron
        ( B ) LOCATION: 534..589

( i x ) FEATURE:
        ( A ) NAME/KEY: intron
        ( B ) LOCATION: 710..764

( i x ) FEATURE:
        ( A ) NAME/KEY: intron
        ( B ) LOCATION: 879..934

( i x ) FEATURE:
        ( A ) NAME/KEY: intron
        ( B ) LOCATION: 1001..1050

( i x ) FEATURE:
        ( A ) NAME/KEY: intron
        ( B ) LOCATION: 1147..1197

( i x ) FEATURE:
        ( A ) NAME/KEY: intron (B) LOCATION: 1354..1410

(ix) FEATURE:
    (A) NAME/KEY: intron
    (B) LOCATION: 1609..1662

(ix) FEATURE:
    (A) NAME/KEY: CDS
    (B) LOCATION: join (413..465, 533..590, 709..765, 878..935,
        1000..1051, 1146..1198, 1353..1411, 1608..1663)

(xi) SEQUENCE DESCRIPTION: SEQ ID NO: 1:

```
AGATTTCTGA CACCGGTGCA ATCTTGACAC TGTACCAACC GGGCAAGTCT CGTCCTTGGT        60

TCTCGGGGACT GCGCCGGT CGCTACCCCT TGGTCATTCA CTCTACCAGA GCGCTGGCTT        120

CGCCGAGGTA TAAAGGATGT TGCGCGACAC CCTCAACACC CCAACTCAAG CCCCACTTGA       180

GCTTTTGCGA GATCCTCCAC ATACCACTCA CTACTTTCAA GTTCTTCAAC ATG TCG AGG     239
                                                        Met Ser Arg
                                                          1

TTT CAC TCT CTT CTC GCT TTC GTC GTT GCT TCC CTT ACG GCT GTG GCC        287
Phe His Ser Leu Leu Ala Phe Val Val Ala Ser Leu Thr Ala Val Ala
      5               10                  15

CAC GCT GGT ATC GGT CCC GTC GCC GAC CTA ACC ATC ACC AAC GCA GCG        335
His Ala Gly Ile Gly Pro Val Ala Asp Leu Thr Ile Thr Asn Ala Ala
 20              25                  30                  35

GTC AGC CCC GAC GGG TTT TCT CGC CAG GCC GTC GTC GTG AAC GGC GGC        383
Val Ser Pro Asp Gly Phe Ser Arg Gln Ala Val Val Val Asn Gly Gly
                 35                  40                  45

ACC CCT GGC CCT CTC ATC ACG GGT AAC ATG GTTCGTCTCG GCTCGCACTA          433
Thr Pro Gly Pro Leu Ile Thr Gly Asn Met
                 50                  55

GGGGGTTGTA TCGTTCCTGA CGTTGTTGGA

G GGG GAT CGC TTC CAG CTC AAT GTC ATC              491
                      Gly Asp Arg Phe Gln Leu Asn Val Ile
                                      60                  65

GAC AAC CTT ACC AAC CAC ACG ATG GTG AAG AGC ACG AGT ATT GTGAGCTGCT    543
Asp Asn Leu Thr Asn His Thr Met Val Lys Ser Thr Ser Ile
                 70                  75

ATTTCTCCGG ACGGGGCTTC ATTGTGCTAA TAATCGTCGT GTGCAG CAC TGG CAC GGT    601
                                                                80

TTC TTC CAG AAG GGT ACC AAC TGG GCC GAC GGT CCC GCC TTC ATC AAC        649
Phe Phe Gln Lys Gly Thr Asn Trp Ala Asp Gly Pro Ala Phe Ile Asn
         85                  90                  95

CAG TGC CCG ATC TCA TCT GGT CAC TCG TTC CTG TAC GAC TTC CAG GTT        697
Gln Cys Pro Ile Ser Ser Gly His Ser Phe Leu Tyr Asp Phe Gln Val
100              105                 110                 115

CCT GAC CAG GCT GTAAGTACGG TCGTTATGGA GTATACTGCG CATTGCTAAA           749
Pro Asp Gln Ala

CCACATGGTG AACAG GGT ACC TTC TGG TAT CAC AGT CAC TTG TCT ACG CAG      800
              Gly Thr Phe Trp Tyr His Ser His Leu Ser Thr Gln
                              120                 125                 130

TAC TGT GAT GGT TTG AGG GGT CCG TTC GTT GTT TAC GAC CCG AAT GAC        848
Tyr Cys Asp Gly Leu Arg Gly Pro Phe Val Val Tyr Asp Pro Asn Asp
                 135                 140                 145

CCG GCC GCC GAC CTG TAC GAC GTC GAC AAC GTAAGGACGA ATTCGAACCG         898
Pro Ala Ala Asp Leu Tyr Asp Val Asp Asn
150                 155

TAAATACTTG CTTACTGATA CTTCTCGATG AATTAG GAC GAC ACT GTC ATT           949
                                        Asp Asp Thr Val Ile
                                                        160
```

| | |
|---|---|
| ACC CTT GTG GAT TGG TAC CAC GTC GCC GCG AAG CTG GGC CCC GCA TTC<br>Thr Leu Val Asp Trp Tyr His Val Ala Ala Lys Leu Gly Pro Ala Phe<br>       165                       170                     175 | 997 |
| CCT GTAAGTCCAT GAGTATTCTG CTGTTGAATC TGTCTTAACT GTGCATATCA CTC<br>Pro                                                                               Leu<br>                                                                                180 | 1053 |
| GGC GCC GAC GCC ACC CTC ATC AAC GGT AAG GGA CGC TCC CCC AGC ACG<br>Gly Ala Asp Ala Thr Leu Ile Asn Gly Lys Gly Arg Ser Pro Ser Thr<br>                    185                       190                       195 | 1101 |
| ACC ACC GCG GAC CTC TCA GTT ATC AGC GTC ACC CCG GGT AAA CGC<br>Thr Thr Ala Asp Leu Ser Val Ile Ser Val Thr Pro Gly Lys Arg<br>                200                   205                  210 | 1146 |
| GTATGCTATA TCTTATCTTA TCTGATGGCA TTTCTCTGAG ACATTCTCCA G | 1197 |
| TAC CGT TTC CGC CTG GTG TCC CTG TCG TGC GAC CCC AAC TAC ACG TTC<br>Tyr Arg Phe Arg Leu Val Ser Leu Ser Cys Asp Pro Asn Tyr Thr Phe<br>               215                   220                     225 | 1245 |
| AGC ATC GAT GGT CAC AAC ATG ACG ATC ATC GAG ACC GAC TCA ATC AAC<br>Ser Ile Asp Gly His Asn Met Thr Ile Ile Glu Thr Asp Ser Ile Asn<br>          230                     235                     240 | 1293 |
| ACG GCG CCC CTC GTC GTC GAC TCC ATT CAG ATC TTC GCC GCC CAG CGT<br>Thr Ala Pro Leu Val Val Asp Ser Ile Gln Ile Phe Ala Ala Gln Arg<br>         245                     250                     255 | 1341 |
| TAC TCC TTC GTG GTAAGTTCGA TTCATCCTCT AACGTTGGTC GCTGTTAGTG<br>Tyr Ser Phe Val<br>260 | 1393 |
| ATCGTATGGT CATGTAG CTC GAG GCC AAC CAG GCC GTC GAC AAC TAC TGG<br>                                  Leu Glu Ala Asn Gln Ala Val Asp Asn Tyr Trp<br>                                                 265                       270 | 1443 |
| ATT CGC GCC AAC CCG AAC TTC GGT AAC GTC GGG TTC ACC GGC GGC ATT<br>Ile Arg Ala Asn Pro Asn Phe Gly Asn Val Gly Phe Thr Gly Gly Ile<br>275                     280                       285                       290 | 1491 |
| AAC TCG GCT ATC CTC CGC TAC GAT GGT GCC GCT GCC GTG GAG CCC ACC<br>Asn Ser Ala Ile Leu Arg Tyr Asp Gly Ala Ala Ala Val Glu Pro Thr<br>               295                   300                     305 | 1539 |
| ACA ACG CAA ACC ACG TCG ACT GCG CCG CTC AAC GAG GTC AAC CTG CAC<br>Thr Thr Gln Thr Thr Ser Thr Ala Pro Leu Asn Glu Val Asn Leu His<br>              310                     315                    320 | 1587 |
| CCG CTG GTT ACC ACC GCT GTG GTATGTAATA TTGTCGGTAA TGTAATACAT<br>Pro Leu Val Thr Thr Ala Val<br>         325 | 1638 |
| TGTTGCTGAC CTCGACCCCC ACAG CCT GGC TCG CCC GTC GCT GGT GGT GTC<br>                                               Pro Gly Ser Pro Val Ala Gly Gly Val<br>                                                 330                       335 | 1689 |
| GAC CTG GCC ATC AAC ATG GCG TTC AAC TTC AAC GGC ACC AAC TTC TTC<br>Asp Leu Ala Ile Asn Met Ala Phe Asn Phe Asn Gly Thr Asn Phe Phe<br>         340                     345                     350 | 1737 |
| ATC AAC GGC ACG TCT TTC ACG CCC CCG ACC GTG CCT GTC CTG CTC CAG<br>Ile Asn Gly Thr Ser Phe Thr Pro Pro Thr Val Pro Val Leu Leu Gln<br>355                     360                       365                       370 | 1785 |
| ATC ATC AGC GGC GCG CAG AAC GCG CAG GAC CTC CTG CCC TCC GGT AGC<br>Ile Ile Ser Gly Ala Gln Asn Ala Gln Asp Leu Leu Pro Ser Gly Ser<br>              375                     380                     385 | 1833 |
| GTC TAC TCG CTT CCC TCG AAC GCC GAC ATC GAG ATC TCC TTC CCC GCC<br>Val Tyr Ser Leu Pro Ser Asn Ala Asp Ile Glu Ile Ser Phe Pro Ala<br>             390                     395                     400 | 1881 |
| ACC GCC GCC GCC CCC GGT GCG CCC CAC CCC TTC CAC TTG CAC GGG CAC<br>Thr Ala Ala Ala Pro Gly Ala Pro His Pro Phe His Leu His Gly His<br>           405                     410                     415 | 1929 |
| GCG TTC GCG GTC GTC CGC AGC GCC GGC AGC ACG GTT TAC AAC TAC GAC<br>Ala Phe Ala Val Val Arg Ser Ala Gly Ser Thr Val Tyr Asn Tyr Asp | 1977 |

| | | | | | | | | | | | | | | | | |
|---|---|---|---|---|---|---|---|---|---|---|---|---|---|---|---|---|
| | | | | 420 | | | | | | 425 | | | | | 430 | |
| AAC | CCC | ATC | TTC | CGC | GAC | GTC | GTC | AGC | ACG | GGG | ACG | CCT | GCG | GCC | GGT | 2025 |
| Asn | Pro | Ile | Phe | Arg | Asp | Val | Val | Ser | Thr | Gly | Thr | Pro | Ala | Ala | Gly | |
| 435 | | | | 440 | | | | | 445 | | | | | | 450 | |
| GAC | AAC | GTC | ACC | ATC | CGC | TTC | CGC | ACC | GAC | AAC | CCC | GGC | CCG | TGG | TTC | 2073 |
| Asp | Asn | Val | Thr | Ile | Arg | Phe | Arg | Thr | Asp | Asn | Pro | Gly | Pro | Trp | Phe | |
| | | | | 455 | | | | | 460 | | | | | 465 | | |
| CTC | CAC | TGC | CAC | ATC | GAC | TTC | CAC | CTC | GAG | GCC | GGC | TTC | GCC | GTC | GTG | 2121 |
| Leu | His | Cys | His | Ile | Asp | Phe | His | Leu | Glu | Ala | Gly | Phe | Ala | Val | Val | |
| | | | 470 | | | | 475 | | | | | 480 | | | | |
| TTC | GCG | GAG | GAC | ATC | CCC | GAC | GTC | GCG | TCG | GCG | AAC | CCC | GTC | CCC | CAG | 2169 |
| Phe | Ala | Glu | Asp | Ile | Pro | Asp | Val | Ala | Ser | Ala | Asn | Pro | Val | Pro | Gln | |
| | | 485 | | | | | 490 | | | | | 495 | | | | |
| GCG | TGG | TCC | GAC | CTC | TGT | CCG | ACC | TAC | GAC | GCG | CTC | GAC | CCG | AGC | GAC | 2217 |
| Ala | Trp | Ser | Asp | Leu | Cys | Pro | Thr | Tyr | Asp | Ala | Leu | Asp | Pro | Ser | Asp | |
| | 500 | | | | 505 | | | | | 510 | | | | | | |
| CAG | TAAATGGCTT | GCGCCGGTCG | ATGATAGGAT | ATGGACGGTG | AGTTCGCACT | | | | | | | | | | | 2270 |
| Gln | | | | | | | | | | | | | | | | |
| 515 | | | | | | | | | | | | | | | | |

TGCAATACGG ACTCTCGCCT CATTATGGTT ACACACTCGC TCTGGATCTC TCGCCTGTCG    2330

ACAGAACAAA CTTGTATAAT TCGCTTAATG GTTGAAACAA ATGGAATATT GGGGTACTAT    2390

GCACGCATCT CGCTGGGTGA GCTTTCGT    2418

( 2 ) INFORMATION FOR SEQ ID NO: 2:

( i ) SEQUENCE CHARACTERISTICS:
        ( A ) LENGTH: 520 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Polyporus pinsitus ( x i ) SEQUENCE DESCRIPTION: SEQ ID NO: 2:

| | | | | | | | | | | | | | | |
|---|---|---|---|---|---|---|---|---|---|---|---|---|---|---|
| Met | Ser | Arg | Phe | His | Ser | Leu | Leu | Ala | Phe | Val | Val | Ala | Ser | Leu | Thr |
| 1 | | | | 5 | | | | | 10 | | | | | 15 | |
| Ala | Val | Ala | His | Ala | Gly | Ile | Gly | Pro | Val | Ala | Asp | Leu | Thr | Ile | Thr |
| | | | 20 | | | | | 25 | | | | | 30 | | |
| Asn | Ala | Ala | Val | Ser | Pro | Asp | Gly | Phe | Ser | Arg | Gln | Ala | Val | Val | Val |
| | | 35 | | | | | 40 | | | | | 45 | | | |
| Asn | Gly | Gly | Thr | Pro | Gly | Pro | Leu | Ile | Thr | Gly | Asn | Met | Gly | Asp | Arg |
| | 50 | | | | | 55 | | | | | 60 | | | | |
| Phe | Gln | Leu | Asn | Val | Ile | Asp | Asn | Leu | Thr | Asn | His | Thr | Met | Val | Lys |
| 65 | | | | | 70 | | | | | 75 | | | | | 80 |
| Ser | Thr | Ser | Ile | His | Trp | His | Gly | Phe | Phe | Gln | Lys | Gly | Thr | Asn | Trp |
| | | | | 85 | | | | | 90 | | | | | 95 | |
| Ala | Asp | Gly | Pro | Ala | Phe | Ile | Asn | Gln | Cys | Pro | Ile | Ser | Ser | Gly | His |
| | | | 100 | | | | | 105 | | | | | 110 | | |
| Ser | Phe | Leu | Tyr | Asp | Phe | Gln | Val | Pro | Asp | Gln | Ala | Gly | Thr | Phe | Trp |
| | | | 115 | | | | | 120 | | | | | 125 | | |
| Tyr | His | Ser | His | Leu | Ser | Thr | Gln | Tyr | Cys | Asp | Gly | Leu | Arg | Gly | Pro |
| | | 130 | | | | | 135 | | | | | 140 | | | |
| Phe | Val | Val | Tyr | Asp | Pro | Asn | Asp | Pro | Ala | Ala | Asp | Leu | Tyr | Asp | Val |
| 145 | | | | | 150 | | | | | 155 | | | | | 160 |
| Asp | Asn | Asp | Asp | Thr | Val | Ile | Thr | Leu | Val | Asp | Trp | Tyr | His | Val | Ala |
| | | | | 165 | | | | | 170 | | | | | 175 | |

| | | | | | | | | | | | | | | |
|---|---|---|---|---|---|---|---|---|---|---|---|---|---|---|
| Ala | Lys | Leu<br>180 | Gly | Pro | Ala | Phe | Pro<br>185 | Leu | Gly | Ala | Asp | Ala<br>190 | Thr | Leu | Ile |
| Asn | Gly | Lys<br>195 | Gly | Arg | Ser | Pro | Ser<br>200 | Thr | Thr | Thr | Ala | Asp<br>205 | Leu | Ser | Val |
| Ile | Ser<br>210 | Val | Thr | Pro | Gly | Lys<br>215 | Arg | Tyr | Arg | Phe | Arg<br>220 | Leu | Val | Ser | Leu |
| Ser<br>225 | Cys | Asp | Pro | Asn | Tyr<br>230 | Thr | Phe | Ser | Ile | Asp<br>235 | Gly | His | Asn | Met | Thr<br>240 |
| Ile | Ile | Glu | Thr | Asp<br>245 | Ser | Ile | Asn | Thr | Ala<br>250 | Pro | Leu | Val | Val | Asp<br>255 | Ser |
| Ile | Gln | Ile | Phe<br>260 | Ala | Ala | Gln | Arg | Tyr<br>265 | Ser | Phe | Val | Leu | Glu<br>270 | Ala | Asn |
| Gln | Ala | Val<br>275 | Asp | Asn | Tyr | Trp | Ile<br>280 | Arg | Ala | Asn | Pro | Asn<br>285 | Phe | Gly | Asn |
| Val | Gly<br>290 | Phe | Thr | Gly | Gly | Ile<br>295 | Asn | Ser | Ala | Ile | Leu<br>300 | Arg | Tyr | Asp | Gly |
| Ala<br>305 | Ala | Ala | Val | Glu | Pro<br>310 | Thr | Thr | Thr | Gln | Thr<br>315 | Thr | Ser | Thr | Ala | Pro<br>320 |
| Leu | Asn | Glu | Val | Asn<br>325 | Leu | His | Pro | Leu | Val<br>330 | Thr | Thr | Ala | Val | Pro<br>335 | Gly |
| Ser | Pro | Val | Ala<br>340 | Gly | Gly | Val | Asp | Leu<br>345 | Ala | Ile | Asn | Met | Ala<br>350 | Phe | Asn |
| Phe | Asn | Gly<br>355 | Thr | Asn | Phe | Phe | Ile<br>360 | Asn | Gly | Thr | Ser | Phe<br>365 | Thr | Pro | Pro |
| Thr | Val<br>370 | Pro | Val | Leu | Leu | Gln<br>375 | Ile | Ile | Ser | Gly | Ala<br>380 | Gln | Asn | Ala | Gln |
| Asp<br>385 | Leu | Leu | Pro | Ser | Gly<br>390 | Ser | Val | Tyr | Ser | Leu<br>395 | Pro | Ser | Asn | Ala | Asp<br>400 |
| Ile | Glu | Ile | Ser | Phe<br>405 | Pro | Ala | Thr | Ala | Ala<br>410 | Ala | Pro | Gly | Ala | Pro<br>415 | His |
| Pro | Phe | His | Leu<br>420 | His | Gly | His | Ala | Phe<br>425 | Ala | Val | Val | Arg | Ser<br>430 | Ala | Gly |
| Ser | Thr | Val<br>435 | Tyr | Asn | Tyr | Asp | Asn<br>440 | Pro | Ile | Phe | Arg | Asp<br>445 | Val | Val | Ser |
| Thr | Gly<br>450 | Thr | Pro | Ala | Ala | Gly<br>455 | Asp | Asn | Val | Thr | Ile<br>460 | Arg | Phe | Arg | Thr |
| Asp<br>465 | Asn | Pro | Gly | Pro | Trp<br>470 | Phe | Leu | His | Cys | His<br>475 | Ile | Asp | Phe | His | Leu<br>480 |
| Glu | Ala | Gly | Phe | Ala<br>485 | Val | Val | Phe | Ala | Glu<br>490 | Asp | Ile | Pro | Asp | Val<br>495 | Ala |
| Ser | Ala | Asn | Pro<br>500 | Val | Pro | Gln | Ala | Trp<br>505 | Ser | Asp | Leu | Cys | Pro<br>510 | Thr | Tyr |
| Asp | Ala | Leu<br>515 | Asp | Pro | Ser | Asp | Gln<br>520 | | | | | | | | |

(2) INFORMATION FOR SEQ ID NO:3:

(i) SEQUENCE CHARACTERISTICS:
        (A) LENGTH: 2880 base pairs
        (B) TYPE: nucleic acid
        (C) STRANDEDNESS: single
        (D) TOPOLOGY: linear (ix) FEATURE:
        (A) NAME/KEY: intron
        (B) LOCATION: 544..592

( i x ) FEATURE:
    ( A ) NAME/KEY: intron
    ( B ) LOCATION: 837..899

( i x ) FEATURE:
    ( A ) NAME/KEY: intron
    ( B ) LOCATION: 1014..1066

( i x ) FEATURE:
    ( A ) NAME/KEY: intron
    ( B ) LOCATION: 1133..1187

( i x ) FEATURE:
    ( A ) NAME/KEY: intron
    ( B ) LOCATION: 1284..1342

( i x ) FEATURE:
    ( A ) NAME/KEY: intron
    ( B ) LOCATION: 1752..1815

( i x ) FEATURE:
    ( A ) NAME/KEY: intron
    ( B ) LOCATION: 1873..1928

( i x ) FEATURE:
    ( A ) NAME/KEY: intron
    ( B ) LOCATION: 2136..2195

( i x ) FEATURE:
    ( A ) NAME/KEY: CDS
    ( B ) LOCATION: join(364..543, 593..661, 716..835, 900..1013,
          1067..1132, 1188..1283, 1343..1498, 1554..1751,
          1816..1872, 1929..2135, 2196..2489)

( i x ) FEATURE:
    ( A ) NAME/KEY: intron
    ( B ) LOCATION: 662..715

( i x ) FEATURE:
    ( A ) NAME/KEY: intron
    ( B ) LOCATION: 1499..1553

( x i ) SEQUENCE DESCRIPTION: SEQ ID NO:3:

```
GCGGCGCACA  AACCGTGGGA  GCCAACACAC  TCCCGTCCAC  TCTCACACTG  GCCAGATTCG       60

CGCGACCGCC  GCCTTTCAGG  CCCAAACAGA  TCTGGCAGGT  TTCGATGGCG  CACGCCGCCG      120

TGCCTGCCGG  ATTCAATTGT  GCGCCAGTCG  GGCATCCGGA  TGGCTCTACC  AGCGCGGTTG      180

ACTGGAAGAG  AACACCGAGG  TCATGCATTC  TGGCCAAGTG  CGGCCAAAGG  ACCGCTCGCT      240

GGTGCGGATA  CTTAAAGGGC  GGCGCGGGGA  GGCCTGTCTA  CCAAGCTCAA  GCTCGCCTTG      300

GGTTCCCAGT  CTCCGCCACC  CTCCTCTTCC  CCCACACAGT  CGCTCCATAG  CACCGTCGGC      360

GCC ATG GGT CTG CAG CGA TTC AGC TTC TTC GTC ACC CTC GCG CTC GTC           408
    Met Gly Leu Gln Arg Phe Ser Phe Phe Val Thr Leu Ala Leu Val
     1           5                  10                  15

GCT CGC TCT CTT GCA GCC ATC GGG CCG GTG GCG AGC CTC GTC GTC GCG           456
Ala Arg Ser Leu Ala Ala Ile Gly Pro Val Ala Ser Leu Val Val Ala
             20                  25                  30

AAC GCC CCC GTC TCG CCC GAC GGC TTC CTT CGG GAT GCC ATC GTG GTC           504
Asn Ala Pro Val Ser Pro Asp Gly Phe Leu Arg Asp Ala Ile Val Val
                 35                  40                  45

AAC GGC GTG GTC CCT TCC CCG CTC ATC ACC GGG AAG AAG GTCGGCGTGT            553
Asn Gly Val Val Pro Ser Pro Leu Ile Thr Gly Lys Lys
         50                  55                  60

TCGTCGTCGT CCTACTCCTT TGCTGACAGC GATCTACAG GGA GAC CGC TTC CAG            607
                                           Gly Asp Arg Phe Gln
                                                            65

CTC AAC GTC GTC GAC ACC TTG ACC AAC CAC AGC ATG CTC AAG TCC ACT           655
Leu Asn Val Val Asp Thr Leu Thr Asn His Ser Met Leu Lys Ser Thr
             70                  75                  80
```

```
AGT ATC GTAAGTGTGA CGATCCGAAT GTGACATCAA TCGGGGCTAA TTAACCGCGC       711
Ser Ile

ACAG CAC TGG CAC GGC TTC TTC CAG GCA GGC ACC AAC TGG GCA GAA GGA      760
     His Trp His Gly Phe Phe Gln Ala Gly Thr Asn Trp Ala Glu Gly
          85                  90                  95

CCC GCG TTC GTC AAC CAG TGC CCT ATT GCT TCC GGG CAT TCA TTC CTG       808
Pro Ala Phe Val Asn Gln Cys Pro Ile Ala Ser Gly His Ser Phe Leu
100                 105                 110

TAC GAC TTC CAT GTG CCC GAC CAG GCA GTAAGCAGGA TTTTCTGGGG             855
Tyr Asp Phe His Val Pro Asp Gln Ala
115                 120

TCCCCGTGTG ATGCAATGTT CTCATGCTCC GACGTGATCG ACAG GGG ACG TTC TGG      911
                                                  Gly Thr Phe Trp
                                                  125

TAC CAC AGT CAT CTG TCT ACG CAG TAC TGT GAC GGG CTG CGG GGG CCG       959
Tyr His Ser His Leu Ser Thr Gln Tyr Cys Asp Gly Leu Arg Gly Pro
        130                 135                 140

TTC GTC GTG TAC GAC CCC AAG GAC CCG CAC GCC AGC CGT TAC GAT GTT       1007
Phe Val Val Tyr Asp Pro Lys Asp Pro His Ala Ser Arg Tyr Asp Val
145                 150                 155

GAC AAT GTACGTGCGC CACGGAGTAT ATCACACAGC ATGCGTTGAC GTCGGGCCAA        1063
Asp Asn
160

CAG GAG AGC ACG GTC ATC ACG TTG ACC GAC TGG TAC CAC ACC GCT GCC       1111
Gln Glu Ser Thr Val Ile Thr Leu Thr Asp Trp Tyr His Thr Ala Ala
             165                 170                 175

CGG CTC GGT CCC AAG TTC CCA GTAAGCTCGC AATGGCTTAG TGTTCACAGG          1162
Arg Leu Gly Pro Lys Phe Pro
                180

TTCTTTGCTT ATGTTGCTTC GATAG CTC GGC GCG GAC GCC ACG CTC ATC AAC       1214
                            Leu Gly Ala Asp Ala Thr Leu Ile Asn
                                185                 190

GGT CTG GGG CGG TCG GCC TCG ACT CCC ACC GCT GCG CTT GCC GTG ATC       1262
Gly Leu Gly Arg Ser Ala Ser Thr Pro Thr Ala Ala Leu Ala Val Ile
        195                 200                 205

AAC GTC CAG CAC GGA AAG CGC GTGAGCATTC TCTTGTATGC CATTTCAATG          1313
Asn Val Gln His Gly Lys Arg
210                 215

CTTTGTGCTG ACCTATCGGA ACCGCGCAG TAC CGC TTC CGT CTC GTT TCG ATC       1366
                                Tyr Arg Phe Arg Leu Val Ser Ile
                                                220

TCG TGT GAC CCG AAC TAC ACG TTC AGC ATC GAC GGG CAC AAC CTG ACC       1414
Ser Cys Asp Pro Asn Tyr Thr Phe Ser Ile Asp Gly His Asn Leu Thr
225                 230                 235

GTC ATC GAG GTC GAC GGC ATC AAT AGC CAG CCT CTC CTT GTC GAC TCT       1462
Val Ile Glu Val Asp Gly Ile Asn Ser Gln Pro Leu Leu Val Asp Ser
240                 245                 250                 255

ATC CAG ATC TTC GCC GCA CAG CGC TAC TCC TTC GTG GTAAGTCCTG            1508
Ile Gln Ile Phe Ala Ala Gln Arg Tyr Ser Phe Val
        260                 265

GCTTGTCGAT GCTCCAAAGT GGCCTCACTC ATATACTTTC GTTAG TTG AAT GCG         1562
                                                  Leu Asn Ala
                                                  270

AAT CAA ACG GTG GGC AAC TAC TGG GTT CGT GCG AAC CCG AAC TTC GGA       1610
Asn Gln Thr Val Gly Asn Tyr Trp Val Arg Ala Asn Pro Asn Phe Gly
        275                 280                 285

ACG GTT GGG TTC GCC GGG GGG ATC AAC TCC GCC ATC TTG CGC TAC CAG       1658
Thr Val Gly Phe Ala Gly Gly Ile Asn Ser Ala Ile Leu Arg Tyr Gln
        290                 295                 300

GGC GCA CCG GTC GCC GAG CCT ACC ACG ACC CAG ACG CCG TCG GTG ATC       1706
```

```
         Gly Ala Pro Val Ala Glu Pro Thr Thr Thr Gln Thr Pro Ser Val Ile
                 305                 310                 315

CCG CTC ATC GAG ACG AAC TTG CAC CCG CTC GCG CGC ATG CCA GTG             1751
Pro Leu Ile Glu Thr Asn Leu His Pro Leu Ala Arg Met Pro Val
        320                 325                 330

GTATGTCTCT TTTCTGATC ATCTGAGTTG CCCGTTGTTG ACCGCATTAT GTGTTACTAT        1811

CTAG CCT GGC AGC CCG ACA CCC GGG GGC GTC GAC AAG GCG CTC AAC CTC        1860
     Pro Gly Ser Pro Thr Pro Gly Gly Val Asp Lys Ala Leu Asn Leu
         335                 340                 345

GCG TTT AAC TTC GTAAGTATCT CTACTACTTA GGCTGGAGGC TCGTCGCTGA             1912
Ala Phe Asn Phe
        350

TCATACGGTG CTTCAG AAC GGC ACC AAC TTC TTC ATC AAC AAC GCG ACT          1961
               Asn Gly Thr Asn Phe Phe Ile Asn Asn Ala Thr
                           355                 360

TTC ACG CCG CCG ACC GTC CCG GTA CTC CTC CAG ATT CTG AGC GGT GCG        2009
Phe Thr Pro Pro Thr Val Pro Val Leu Leu Gln Ile Leu Ser Gly Ala
        365                 370                 375

CAG ACC GCA CAA GAC CTG CTC CCC GCA GGC TCT GTC TAC CCG CTC CCG        2057
Gln Thr Ala Gln Asp Leu Leu Pro Ala Gly Ser Val Tyr Pro Leu Pro
380                 385                 390                 395

GCC CAC TCC ACC ATC GAG ATC ACG CTG CCC GCG ACC GCC TTG GCC CCG        2105
Ala His Ser Thr Ile Glu Ile Thr Leu Pro Ala Thr Ala Leu Ala Pro
                400                 405                 410

GGT GCA CCG CAC CCC TTC CAC CTG CAC GGT GTATGTTCCC CTGCCTTCCC          2155
Gly Ala Pro His Pro Phe His Leu His Gly
        415                 420

TTCTTATCCC CGAACCAGTG CTCACGTCCG TCCCATCTAG CAC GCC TTC GCG GTC        2210
                                            His Ala Phe Ala Val
                                                            425

GTT CGC AGC GCG GGG AGC ACC ACG TAT AAC TAC AAC GAC CCG ATC TTC        2258
Val Arg Ser Ala Gly Ser Thr Thr Tyr Asn Tyr Asn Asp Pro Ile Phe
                430                 435                 440

CGC GAC GTC GTG AGC ACG GGC ACG CCC GCC GCG GGC GAC AAC GTC ACG        2306
Arg Asp Val Val Ser Thr Gly Thr Pro Ala Ala Gly Asp Asn Val Thr
            445                 450                 455

ATC CGC TTC CAG ACG GAC AAC CCC GGG CCG TGG TTC CTC CAC TGC CAC        2354
Ile Arg Phe Gln Thr Asp Asn Pro Gly Pro Trp Phe Leu His Cys His
        460                 465                 470

ATC GAC TTC CAC CTC GAC GCA GGC TTC GCG ATC GTG TTC GCA GAG GAC        2402
Ile Asp Phe His Leu Asp Ala Gly Phe Ala Ile Val Phe Ala Glu Asp
475                 480                 485                 490

GTT GCG GAC GTG AAG GCG GCG AAC CCG GTT CCG AAG GCG TGG TCG GAC        2450
Val Ala Asp Val Lys Ala Ala Asn Pro Val Pro Lys Ala Trp Ser Asp
                495                 500                 505

CTG TGC CCG ATC TAC GAC GGG CTG AGC GAG GCT AAC CAG TGAGCGGAGG         2499
Leu Cys Pro Ile Tyr Asp Gly Leu Ser Glu Ala Asn Gln
        510                 515

GCGTGGTGTT GAGCGTAAAG CTCGGGCGTC GACCTGGGGG GTTGAAGGTG TTCTGATTGA      2559

AATGGTCTTT GGGTTTATTT GTTGTTATTC TAACTCGGTT CTCTACGCAA GGACCGAGGA      2619

TTGTATAGGA TGAAGTAACT TCCCTAATGT ATTATGATAT CAATTGACGG AGGCATGGAC      2679

TGCGAAGTGT GTACAATGTG GTAGTGGTCT AGGCCTTGGA GACAAGCTGT GGATTTTTCT      2739

TGGGGGATGA AGAGGCGTGA AGGCTGAGAG CTATGCTATG CCTAGTGACG TGGTTATAGT      2799

AAATGTCCAT TACATTGACC AAGAACGACA AGAACCATAA GCTTGCTGAG GATAGATGGG      2859

GGCGCGTCCG CGAACGACTT G                                                2880
```

( 2 ) INFORMATION FOR SEQ ID NO:4:

( i ) SEQUENCE CHARACTERISTICS:
        ( A ) LENGTH: 519 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Gly Leu Gln Arg Phe Ser Phe Phe Val Thr Leu Ala Leu Val Ala
 1               5                  10                  15

Arg Ser Leu Ala Ala Ile Gly Pro Val Ala Ser Leu Val Val Ala Asn
             20                  25                  30

Ala Pro Val Ser Pro Asp Gly Phe Leu Arg Asp Ala Ile Val Val Asn
         35                  40                  45

Gly Val Val Pro Ser Pro Leu Ile Thr Gly Lys Lys Gly Asp Arg Phe
     50                  55                  60

Gln Leu Asn Val Val Asp Thr Leu Thr Asn His Ser Met Leu Lys Ser
 65                  70                  75                  80

Thr Ser Ile His Trp His Gly Phe Phe Gln Ala Gly Thr Asn Trp Ala
                 85                  90                  95

Glu Gly Pro Ala Phe Val Asn Gln Cys Pro Ile Ala Ser Gly His Ser
                100                 105                 110

Phe Leu Tyr Asp Phe His Val Pro Asp Gln Ala Gly Thr Phe Trp Tyr
            115                 120                 125

His Ser His Leu Ser Thr Gln Tyr Cys Asp Gly Leu Arg Gly Pro Phe
        130                 135                 140

Val Val Tyr Asp Pro Lys Asp Pro His Ala Ser Arg Tyr Asp Val Asp
145                 150                 155                 160

Asn Glu Ser Thr Val Ile Thr Leu Thr Asp Trp Tyr His Thr Ala Ala
                165                 170                 175

Arg Leu Gly Pro Lys Phe Pro Leu Gly Ala Asp Ala Thr Leu Ile Asn
            180                 185                 190

Gly Leu Gly Arg Ser Ala Ser Thr Pro Thr Ala Ala Leu Ala Val Ile
        195                 200                 205

Asn Val Gln His Gly Lys Arg Tyr Arg Phe Arg Leu Val Ser Ile Ser
210                 215                 220

Cys Asp Pro Asn Tyr Thr Phe Ser Ile Asp Gly His Asn Leu Thr Val
225                 230                 235                 240

Ile Glu Val Asp Gly Ile Asn Ser Gln Pro Leu Leu Val Asp Ser Ile
                245                 250                 255

Gln Ile Phe Ala Ala Gln Arg Tyr Ser Phe Val Leu Asn Ala Asn Gln
            260                 265                 270

Thr Val Gly Asn Tyr Trp Val Arg Ala Asn Pro Asn Phe Gly Thr Val
        275                 280                 285

Gly Phe Ala Gly Gly Ile Asn Ser Ala Ile Leu Arg Tyr Gln Gly Ala
    290                 295                 300

Pro Val Ala Glu Pro Thr Thr Gln Thr Pro Ser Val Ile Pro Leu
305                 310                 315                 320

Ile Glu Thr Asn Leu His Pro Leu Ala Arg Met Pro Val Pro Gly Ser
                325                 330                 335

Pro Thr Pro Gly Gly Val Asp Lys Ala Leu Asn Leu Ala Phe Asn Phe
            340                 345                 350

Asn Gly Thr Asn Phe Phe Ile Asn Asn Ala Thr Phe Thr Pro Pro Thr
        355                 360                 365
```

| | | | | | | | | | | | | | |
|---|---|---|---|---|---|---|---|---|---|---|---|---|---|
| Val | Pro<br>370 | Val | Leu | Leu | Gln<br>375 | Ile | Leu | Ser | Gly | Ala<br>380 | Gln | Thr | Ala | Gln | Asp |
| Leu<br>385 | Leu | Pro | Ala | Gly | Ser<br>390 | Val | Tyr | Pro | Leu | Pro<br>395 | Ala | His | Ser | Thr | Ile<br>400 |
| Glu | Ile | Thr | Leu | Pro<br>405 | Ala | Thr | Ala | Leu | Ala<br>410 | Pro | Gly | Ala | Pro | His<br>415 | Pro |
| Phe | His | Leu | His<br>420 | Gly | His | Ala | Phe | Ala<br>425 | Val | Val | Arg | Ser | Ala<br>430 | Gly | Ser |
| Thr | Thr | Tyr<br>435 | Asn | Tyr | Asn | Asp | Pro<br>440 | Ile | Phe | Arg | Asp | Val<br>445 | Val | Ser | Thr |
| Gly | Thr<br>450 | Pro | Ala | Ala | Gly | Asp<br>455 | Asn | Val | Thr | Ile | Arg<br>460 | Phe | Gln | Thr | Asp |
| Asn<br>465 | Pro | Gly | Pro | Trp | Phe<br>470 | Leu | His | Cys | His | Ile<br>475 | Asp | Phe | His | Leu | Asp<br>480 |
| Ala | Gly | Phe | Ala | Ile<br>485 | Val | Phe | Ala | Glu | Asp<br>490 | Val | Ala | Asp | Val | Lys<br>495 | Ala |
| Ala | Asn | Pro | Val<br>500 | Pro | Lys | Ala | Trp | Ser<br>505 | Asp | Leu | Cys | Pro | Ile<br>510 | Tyr | Asp |
| Gly | Leu | Ser<br>515 | Glu | Ala | Asn | Gln |

( 2 ) INFORMATION FOR SEQ ID NO: 5:

( i ) SEQUENCE CHARACTERISTICS:
        ( A ) LENGTH: 3102 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Polyporus pinsitus ( i x ) FEATURE:
        ( A ) NAME/KEY: intron
        ( B ) LOCATION: 666..720

( i x ) FEATURE:
        ( A ) NAME/KEY: intron
        ( B ) LOCATION: 790..845

( i x ) FEATURE:
        ( A ) NAME/KEY: intron
        ( B ) LOCATION: 1125..1182

( i x ) FEATURE:
        ( A ) NAME/KEY: intron
        ( B ) LOCATION: 1390..1450

( i x ) FEATURE:
        ( A ) NAME/KEY: intron
        ( B ) LOCATION: 1607..1661

( i x ) FEATURE:
        ( A ) NAME/KEY: intron
        ( B ) LOCATION: 1863..1918

( i x ) FEATURE:
        ( A ) NAME/KEY: intron
        ( B ) LOCATION: 1976..2025

( i x ) FEATURE:
        ( A ) NAME/KEY: intron
        ( B ) LOCATION: 2227..2285

( i x ) FEATURE:
        ( A ) NAME/KEY: intron
        ( B ) LOCATION: 2403..2458

( i x ) FEATURE:
    ( A ) NAME/KEY: intron
    ( B ) LOCATION: 2576..2627

( i x ) FEATURE:
    ( A ) NAME/KEY: CDS
    ( B ) LOCATION: join (665..721, 789..846, 1124..1183, 1389..1451
        1606..1662, 1862..1919, 1975..2026, 2226..2286, 2402..245
        2575..2628).

( x i ) SEQUENCE DESCRIPTION: SEQ ID NO: 5:

| | | | | |
|---|---|---|---|---|
| TTTCCCGACT | AAACCAATCT | CAGNCCGCTT | CCTCCTAGGG | AACCGAGCGA | TGTGGCGGCC | 60 |
| CTCTCTATCC | AAGCTGTCCA | TAAGAAGACG | TTCAAATGCC | GCAGCAAGCG | AGGAAATAAG | 120 |
| CATCTAACAG | TGTTTTTCCC | ATAGTCGCAT | TTGCGCCGCC | TGTCGGACCG | ACGCCCCTAG | 180 |
| AGCGCTTTGG | GAAACGTCGC | AAGTGGCGGG | TGTTATTCGT | GTAGACGAGA | CGGTATTTGT | 240 |
| CTCATCATTC | CCGTGCTTCA | GGTTGACACA | GCCCAAAGGT | CTATGTACGG | CCCTTCACAT | 300 |
| TCCCTGACAC | ATTGACGCAA | CCCTCGGTGC | GCCTCCGACA | GTGCCTCGGT | TGTAGTATCG | 360 |
| GGACGCCCTA | GGATGCAAGA | TTGGAAGTCA | CCAAGGCCCG | AAGGGTATAA | AATACCGAGA | 420 |
| GGTCCTACCA | CTTCTGCATC | TCCAGTCGCA | GAGTTCCTCT | CCCTTGCCAG | CCACAGCTCG | 480 |

```
AG  ATG TCC TTC TCT AGC CTT CGC CGT GCC TTG GTC TTC CTG GGT GCT      527
    Met Ser Phe Ser Ser Leu Arg Arg Ala Leu Val Phe Leu Gly Ala
     1               5                  10                  15

TGC AGC AGT GCG CTG GCC TCC ATC GGC CCA GTC ACT GAG CTC GAC ATC      575
Cys Ser Ser Ala Leu Ala Ser Ile Gly Pro Val Thr Glu Leu Asp Ile
                20                  25                  30

GTT AAC AAG GTC ATC GCC CCG GAT GGC GTC GCT CGT GAT ACA GTC CTC      623
Val Asn Lys Val Ile Ala Pro Asp Gly Val Ala Arg Asp Thr Val Leu
                35                  40                  45

GCC GGG GGC ACG TTC CCG GGC CCA CTC ATC ACA GGA AAG AAG              665
Ala Gly Gly Thr Phe Pro Gly Pro Leu Ile Thr Gly Lys Lys
            50                  55                  60
```

| | | | |
|---|---|---|---|
| GTATGCTAAG | TAGTCCCGCC | CCCATCATCC | TGTGGCTGAC | GTTCGACGCC | GCCAG | 720 |

```
GGT GAC AAC TTC CGC ATC AAC GTC GTC GAC AAG TTG GTT AAC CAG ACT      768
Gly Asp Asn Phe Arg Ile Asn Val Val Asp Lys Leu Val Asn Gln Thr
                65                  70                  75

ATG CTG ACA TCC ACC ACC ATT GTATGTCACT AGCTCTCGCT ATCTCGAGAC         819
Met Leu Thr Ser Thr Thr Ile
        80

CCGCTGACCG ACAACATTTG CCGTAG CAC TGG CAC GGG ATG TTC CAG CAT         869
                              His Trp His Gly Met Phe Gln His
                                               85          90

ACG ACG AAC TGG GCG GAT GGT CCC GCC TTT GTG ACT CAA TGC CCT ATC      917
Thr Thr Asn Trp Ala Asp Gly Pro Ala Phe Val Thr Gln Cys Pro Ile
                95                 100                 105

ACC ACT GGT GAT GAT TTC CTG TAC AAC TTC CGC GTG CCC GAC CAG ACA      965
Thr Thr Gly Asp Asp Phe Leu Tyr Asn Phe Arg Val Pro Asp Gln Thr
        110                 115                 120
```

| | | | |
|---|---|---|---|
| GTACGCAAAG | GGCAGCATGC | GTACTCAAAG | ACATCTCTAA | GCATTTGCTA | CCTAG | 1020 |

```
GGA ACG TAC TGG TAC CAT AGC CAT CTG GCC TTG CAG TAC TGT GAT GGG     1068
Gly Thr Tyr Trp Tyr His Ser His Leu Ala Leu Gln Tyr Cys Asp Gly
125                 130                 135                 140

CTT CGC GGC CCC CTG GTG ATT TAC GAT CCC CAT GAT CCG CAG GCA TAC     1116
Leu Arg Gly Pro Leu Val Ile Tyr Asp Pro His Asp Pro Gln Ala Tyr
                145                 150                 155

CTG TAT GAC GTC GAT GAC GTACGCAGCA CAGTTTCCCT AAAACGGTTA            1164
Leu Tyr Asp Val Asp Asp
                160
```

-continued

| | |
|---|---|
| ACTTCTAATT CTGTAAATAT CTTCATAG GAG AGC ACC GTT ATC ACT CTG<br>                     Glu Ser Thr Val Ile Thr Leu<br>                              165 | 1213 |
| GCA GAC TGG TAC CAT ACC CCG GCG CCT CTG CTG CCG CCT GCC GCG<br>Ala Asp Trp Tyr His Thr Pro Ala Pro Leu Leu Pro Pro Ala Ala<br>170          175          180 | 1258 |
| GTACGCCTCC ACACATCTGC ACAGCGTTCC GTATCTCATA CCCTTAAAGT TTATCGGACA | 1318 |
| ACT TTG ATT AAT GGC CTG GGT CGC TGG CCT GGC AAC CCC ACC GCC GAC<br>Thr Leu Ile Asn Gly Leu Gly Arg Trp Pro Gly Asn Pro Thr Ala Asp<br>185         190          195          200 | 1366 |
| CTA GCC GTC ATC GAA GTC CAG CAC GGA AAG CGC GTATGTCATA GCTCGGTTAT<br>Leu Ala Val Ile Glu Val Gln His Gly Lys Arg<br>        205         210 | 1419 |
| CTATTCATAC TCGCGGCCTC GAAGCTAAAA CCTTGTTCCA G TAC CGG TTC CGA<br>                                    Tyr Arg Phe Arg<br>                                      215 | 1472 |
| CTG GTC AGC ACC TCA TGC GAC CCC AAC TAC AAC TTC ACT ATC GAT GGC<br>Leu Val Ser Thr Ser Cys Asp Pro Asn Tyr Asn Phe Thr Ile Asp Gly<br>        220          225          230 | 1520 |
| CAC ACC ATG ACA ATC ATC GAG GCG GAT GGG CAG AAC ACC CAG CCA CAC<br>His Thr Met Thr Ile Ile Glu Ala Asp Gly Gln Asn Thr Gln Pro His<br>        235          240          245 | 1568 |
| CAA GTC GAC GGA CTT CAG ATC TTC GCG GCA CAG CGG TAC TCC TTC GTT<br>Gln Val Asp Gly Leu Gln Ile Phe Ala Ala Gln Arg Tyr Ser Phe Val<br>250         255          260 | 1616 |
| GTATGTTTTC CGCATTTCGG GAAAAGGAAT TGCGCTGACA GCTCGAGTGT GCGTAG | 1672 |
| CTT AAC GCT AAC CAA GCG GTC AAC AAC TAC TGG ATC CGT GCG AAC CCT<br>Leu Asn Ala Asn Gln Ala Val Asn Asn Tyr Trp Ile Arg Ala Asn Pro<br>265         270          275 | 1720 |
| AAC CGT GCT AAC ACT ACG GGC TTC GCC AAC GGC ATC AAC TCC GCC ATC<br>Asn Arg Ala Asn Thr Thr Gly Phe Ala Asn Gly Ile Asn Ser Ala Ile<br>280         285          290          295 | 1768 |
| CTG CGC TAC AAG GGG GCG CCG ATT AAG GAG CCT ACG ACG AAC CAG ACT<br>Leu Arg Tyr Lys Gly Ala Pro Ile Lys Glu Pro Thr Thr Asn Gln Thr<br>         300          305          310 | 1816 |
| ACC ATC CGG AAC TTT TTG TGG GAG ACG GAC TTG CAC CCG CTC ACT GAC<br>Thr Ile Arg Asn Phe Leu Trp Glu Thr Asp Leu His Pro Leu Thr Asp<br>        315          320         325 | 1864 |
| CCA CGT GCA GTAAGTTCTA CACAGTCACC AACGGTGAGC TGTTGTCTGA<br>Pro Arg Ala<br>       330 | 1913 |
| TTGCACTGTG TTATAG CCT GGC CTT CCT TTC AAG GGG GGC GTT GAC CAC<br>              Pro Gly Leu Pro Phe Lys Gly Gly Val Asp His<br>                      335          340 | 1962 |
| GCT TTG AAC CTC AAC CTC ACT TTC GTACGTAGCG CCTCAGATAT CGAGTAGTCT<br>Ala Leu Asn Leu Asn Leu Thr Phe<br>       345 | 2016 |
| ATCTCCTGAC CGATTGACAG AAT GGA TCG GAG TTC TTC ATC AAC GAT GCG<br>                       Asn Gly Ser Glu Phe Phe Ile Asn Asp Ala<br>                       350          355 | 2066 |
| CCT TTC GTC CCT CCG ACT GTC CCG GTG CTA CTG CAG ATC CTG AAC GGA<br>Pro Phe Val Pro Pro Thr Val Pro Val Leu Leu Gln Ile Leu Asn Gly<br>360         365          370          375 | 2114 |
| ACG CTC GAC GCG AAC GAC CTC CTG CCG CCC GGC AGC GTC TAC AAC CTT<br>Thr Leu Asp Ala Asn Asp Leu Leu Pro Pro Gly Ser Val Tyr Asn Leu<br>        380          385          390 | 2162 |
| CCT CCG GAC TCC ACC ATC GAG CTG TCC ATT CCC GGA GGT GTG ACG GGT<br>Pro Pro Asp Ser Thr Ile Glu Leu Ser Ile Pro Gly Gly Val Thr Gly<br>        395          400         405 | 2210 |

```
GGC CCG CAC CCA TTC CAT TTG CAC GGG GTAATAATCT CTCTTTATAC                    2257
Gly Pro His Pro Phe His Leu His Gly
        410                 415

TTTGGTCTCC CGATGCTGAC TTTCACTGCT CATCTTCAG CAC GCT TTC TCC GTC              2311
                                           His Ala Phe Ser Val
                                                           420

GTG CGT AGC GCC GGC AGC ACC GAA TAC AAC TAC GCG AAC CCG GTG AAG            2359
Val Arg Ser Ala Gly Ser Thr Glu Tyr Asn Tyr Ala Asn Pro Val Lys
            425                 430                 435

CGC GAC ACG GTC AGC ATT GGT CTT GCG GGC GAC AAC GTC ACC GTG CGC            2407
Arg Asp Thr Val Ser Ile Gly Leu Ala Gly Asp Asn Val Thr Val Arg
            440                 445                 450

TTC GTG GTATGTTTTA CAGCCTCTCT ATCTCCGTGG GCGTTCGGAA GTTGACTGGG             2463
Phe Val
    455

GCGTAG ACC GAC AAC CCC GGC CCG TGG TTC CTC CAC TGT CAC ATC GAC             2511
       Thr Asp Asn Pro Gly Pro Trp Phe Leu His Cys His Ile Asp
                       460                 465

TTC CAT TTG CAA GCA GGC CTC GCC ATC GTG TTC GCG GAG GAC GCG CAG            2559
Phe His Leu Gln Ala Gly Leu Ala Ile Val Phe Ala Glu Asp Ala Gln
470             475                 480                 485

GAC ACG AAG CTT GTG AAC CCC GTC CCT GTACGTCTTC TGGATGCATG                  2606
Asp Thr Lys Leu Val Asn Pro Val Pro
                490

CGCTCCGCAC AGTGACTCAT CTTTTGCAAC AG GAG GAC TGG AAC AAG CTG TGC            2659
                                   Glu Asp Trp Asn Lys Leu Cys
                                   495                 500

CCC ACC TTC GAT AAG GCG ATG AAC ATC ACG GTT TGAGCGATGC                     2702
Pro Thr Phe Asp Lys Ala Met Asn Ile Thr Val
            505                 510

GTGGCGCTCA TGGTCATTTT CTTGGAATCT TTGCATAGGG CTGCAGCACG CTGGATACTC         2762
TTTCCCTTAG CAGGATATTA TTTAATGACC CCTGCGTTTA GTGCTTAGTT AGCTTTACTA         2822
CTGGTTGTAA TGTACGCAGC ATGCGTAATT CGGATAATGC TATCAATGTG TATATTATGA         2882
CACGCGTCAT GCGCGATGCT TGAGTTGCAA GGTCGGTTTC CGATGCTCGA CATAAACGTT         2942
TCACTTACAT ACACATTGGG TCTAGAACTG GATCTATCCA TGTATACAAA AACTCCTCAT         3002
ACAGCTGACT GGGGCGCTCT AGAGCATGGG TCCGATTGAT CAGATGTCGC GAACACGAGC         3062
CTCCTGAGCT CGAGGACTCT GAGAAGCGGC GGTGCGTTCT                               3102
```

( 2 ) INFORMATION FOR SEQ ID NO:6:

( i ) SEQUENCE CHARACTERISTICS:
        ( A ) LENGTH: 512 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Polyporus pinsitus ( x i ) SEQUENCE DESCRIPTION: SEQ ID NO: 6:

```
Met Ser Phe Ser Ser Leu Arg Arg Ala Leu Val Phe Leu Gly Ala Cys
1               5                   10                  15

Ser Ser Ala Leu Ala Ser Ile Gly Pro Val Thr Glu Leu Asp Ile Val
            20                  25                  30

Asn Lys Val Ile Ala Pro Asp Gly Val Ala Arg Asp Thr Val Leu Ala
            35                  40                  45

Gly Gly Thr Phe Pro Gly Pro Leu Ile Thr Gly Lys Lys Gly Asp Asn
```

-continued

```
             50                    55                      60
Phe  Arg  Ile  Asn  Val  Val  Asp  Lys  Leu  Val  Asn  Gln  Thr  Met  Leu  Thr
65                       70                       75                       80

Ser  Thr  Thr  Ile  His  Trp  His  Gly  Met  Phe  Gln  His  Thr  Thr  Asn  Trp
                    85                       90                            95

Ala  Asp  Gly  Pro  Ala  Phe  Val  Thr  Gln  Cys  Pro  Ile  Thr  Thr  Gly  Asp
               100                      105                      110

Asp  Phe  Leu  Tyr  Asn  Phe  Arg  Val  Pro  Asp  Gln  Thr  Gly  Thr  Tyr  Trp
          115                      120                      125

Tyr  His  Ser  His  Leu  Ala  Leu  Gln  Tyr  Cys  Asp  Gly  Leu  Arg  Gly  Pro
     130                 135                      140

Leu  Val  Ile  Tyr  Asp  Pro  His  Asp  Pro  Gln  Ala  Tyr  Leu  Tyr  Asp  Val
145                      150                      155                      160

Asp  Asp  Glu  Ser  Thr  Val  Ile  Thr  Leu  Ala  Asp  Trp  Tyr  His  Thr  Pro
               165                      170                      175

Ala  Pro  Leu  Leu  Pro  Pro  Ala  Ala  Thr  Leu  Ile  Asn  Gly  Leu  Gly  Arg
               180                      185                      190

Trp  Pro  Gly  Asn  Pro  Thr  Ala  Asp  Leu  Ala  Val  Ile  Glu  Val  Gln  His
          195                      200                      205

Gly  Lys  Arg  Tyr  Arg  Phe  Arg  Leu  Val  Ser  Thr  Ser  Cys  Asp  Pro  Asn
210                      215                      220

Tyr  Asn  Phe  Thr  Ile  Asp  Gly  His  Thr  Met  Thr  Ile  Ile  Glu  Ala  Asp
225                      230                      235                      240

Gly  Gln  Asn  Thr  Gln  Pro  His  Gln  Val  Asp  Gly  Leu  Gln  Ile  Phe  Ala
               245                      250                      255

Ala  Gln  Arg  Tyr  Ser  Phe  Val  Leu  Asn  Ala  Asn  Gln  Ala  Val  Asn  Asn
               260                      265                      270

Tyr  Trp  Ile  Arg  Ala  Asn  Pro  Asn  Arg  Ala  Asn  Thr  Thr  Gly  Phe  Ala
               275                      280                      285

Asn  Gly  Ile  Asn  Ser  Ala  Ile  Leu  Arg  Tyr  Lys  Gly  Ala  Pro  Ile  Lys
     290                      295                      300

Glu  Pro  Thr  Thr  Asn  Gln  Thr  Thr  Ile  Arg  Asn  Phe  Leu  Trp  Glu  Thr
305                      310                      315                      320

Asp  Leu  His  Pro  Leu  Thr  Asp  Pro  Arg  Ala  Pro  Gly  Leu  Pro  Phe  Lys
               325                      330                      335

Gly  Gly  Val  Asp  His  Ala  Leu  Asn  Leu  Asn  Leu  Thr  Phe  Asn  Gly  Ser
               340                      345                      350

Glu  Phe  Phe  Ile  Asn  Asp  Ala  Pro  Phe  Val  Pro  Pro  Thr  Val  Pro  Val
          355                      360                      365

Leu  Leu  Gln  Ile  Leu  Asn  Gly  Thr  Leu  Asp  Ala  Asn  Asp  Leu  Leu  Pro
370                      375                      380

Pro  Gly  Ser  Val  Tyr  Asn  Leu  Pro  Pro  Asp  Ser  Thr  Ile  Glu  Leu  Ser
385                      390                      395                      400

Ile  Pro  Gly  Gly  Val  Thr  Gly  Gly  Pro  His  Pro  Phe  His  Leu  His  Gly
               405                      410                      415

His  Ala  Phe  Ser  Val  Val  Arg  Ser  Ala  Gly  Ser  Thr  Glu  Tyr  Asn  Tyr
               420                      425                      430

Ala  Asn  Pro  Val  Lys  Arg  Asp  Thr  Val  Ser  Ile  Gly  Leu  Ala  Gly  Asp
          435                      440                      445

Asn  Val  Thr  Val  Arg  Phe  Val  Thr  Asp  Asn  Pro  Gly  Pro  Trp  Phe  Leu
     450                      455                      460

His  Cys  His  Ile  Asp  Phe  His  Leu  Gln  Ala  Gly  Leu  Ala  Ile  Val  Phe
465                      470                      475                      480
```

5,667,531

55 56

-continued

| Ala | Glu | Asp | Ala | Gln | Asp | Thr | Lys | Leu | Val | Asn | Pro | Val | Pro | Glu | Asp |
|  |  |  |  | 485 |  |  |  |  | 490 |  |  |  |  | 495 |  |

| Trp | Asn | Lys | Leu | Cys | Pro | Thr | Phe | Asp | Lys | Ala | Met | Asn | Ile | Thr | Val |
|  |  |  |  | 500 |  |  |  |  | 505 |  |  |  |  | 510 |  |

( 2 ) INFORMATION FOR SEQ ID NO:7:

( i ) SEQUENCE CHARACTERISTICS:
  ( A ) LENGTH: 2860 base pairs
  ( B ) TYPE: nucleic acid
  ( C ) STRANDEDNESS: single
  ( D ) TOPOLOGY: linear ( i x ) FEATURE:
  ( A ) NAME/KEY: intron
  ( B ) LOCATION: 851..905

( i x ) FEATURE:
  ( A ) NAME/KEY: intron
  ( B ) LOCATION: 1266..1320

( i x ) FEATURE:
  ( A ) NAME/KEY: intron
  ( B ) LOCATION: 1351..1376

( i x ) FEATURE:
  ( A ) NAME/KEY: intron
  ( B ) LOCATION: 1416..1468

( i x ) FEATURE:
  ( A ) NAME/KEY: intron
  ( B ) LOCATION: 1625..1683

( i x ) FEATURE:
  ( A ) NAME/KEY: intron
  ( B ) LOCATION: 1882..1934

( i x ) FEATURE:
  ( A ) NAME/KEY: intron
  ( B ) LOCATION: 2202..2252

( i x ) FEATURE:
  ( A ) NAME/KEY: intron
  ( B ) LOCATION: 2370..2425

( i x ) FEATURE:
  ( A ) NAME/KEY: intron
  ( B ) LOCATION: 2543..2599

( i x ) FEATURE:
  ( A ) NAME/KEY: CDS
  ( B ) LOCATION: join(540..725, 782..850, 906..1025, 1086..1265,
   1321..1350, 1377..1415, 1469..1624, 1684..1881,
   1935..2201, 2253..2369, 2426..2542, 2600..2653)

( x i ) SEQUENCE DESCRIPTION: SEQ ID NO:7:

| GGGGGGCGCG | TCAATGGTCC | GTTTGCGAAC | ACATATGCAG | GATAAACAGT | GCGAAATATC | 60 |
| AATGTGGCGG | CGACACAACC | TCGCCGGCCG | ACACTCGACG | CTGTTGATCA | TGATCATGTC | 120 |
| TTGTGAGCAT | TCTATACGCA | GCCTTGGAAA | TCTCAGGCGA | ATTTGTCTGA | ATTGCGCTGG | 180 |
| GAGGCTGGCA | GCGCAGATCG | GTGTGTCGGT | GCAGTAGCCG | ACGCAGCACC | TGGCGGAAGC | 240 |
| CGACATCTCG | GGTACGACTT | GATCTCCGCC | AGATCACTGC | GGTTCCGCCA | TCGGCCGCGG | 300 |
| GGCCCATTCT | GTGTGTGCGC | TGTAGCACTC | TGCATTCAGG | CTCAACGTAT | CCATGCTAGA | 360 |
| GGACCGTCCA | GCTGTTGGCG | CACGATTCGC | GCAGAAAGCT | GTACAGGCAG | ATATAAGGAT | 420 |
| GTCCGTCCGT | CAGAGACTCG | TCACTCACAA | GCCTCTTTTC | CTCTTCGCCT | TTCCAGCCTC | 480 |
| TTCCAACGCC | TGCCATCGTC | CTCTTAGTTC | GCTCGTCCAT | TCTTTCTGCG | TAGTTAATC | 539 |

| ATG | GGC | AGG | TTC | TCA | TCT | CTC | TGC | GCG | CTC | ACC | GCC | GTC | ATC | CAC | TCT | 587 |
| Met | Gly | Arg | Phe | Ser | Ser | Leu | Cys | Ala | Leu | Thr | Ala | Val | Ile | His | Ser |  |
| 1 |  |  |  | 5 |  |  |  |  | 10 |  |  |  |  | 15 |  |  |

| | | | | | | | | | | | | | | |
|---|---|---|---|---|---|---|---|---|---|---|---|---|---|---|
| TTT | GGT | CGT | GTC | TCC | GCC | GCT | ATC | GGG | CCT | GTG | ACC | GAC | CTC | ACC | ATC | 635
| Phe | Gly | Arg | Val | Ser | Ala | Ala | Ile | Gly | Pro | Val | Thr | Asp | Leu | Thr | Ile |
| | | 20 | | | | | 25 | | | | | 30 | | | |

```
TTT GGT CGT GTC TCC GCC GCT ATC GGG CCT GTG ACC GAC CTC ACC ATC            635
Phe Gly Arg Val Ser Ala Ala Ile Gly Pro Val Thr Asp Leu Thr Ile
         20                  25                  30

TCC AAT GGG GAC GTT TCT CCC GAC GGC TTC ACT CGT GCC GCA GTG CTT            683
Ser Asn Gly Asp Val Ser Pro Asp Gly Phe Thr Arg Ala Ala Val Leu
             35                  40                  45

GCA AAC GGC GTC TTC CCG GGT CCT CTT ATC ACG GGA AAC AAG                    725
Ala Asn Gly Val Phe Pro Gly Pro Leu Ile Thr Gly Asn Lys
         50                  55                  60

GTACGTGGCA TGCGTTCAGT CTACACCCTA CAAGCCTTCT AACTCTTTTA CCACAG              781

GGC GAC AAC TTC CAG ATC AAT GTT ATC GAC AAC CTC TCT AAC GAG ACG            829
Gly Asp Asn Phe Gln Ile Asn Val Ile Asp Asn Leu Ser Asn Glu Thr
                 65                  70                  75

ATG TTG AAG TCG ACC TCC ATC GTATGTGCTT CTACTGCTTC TTAGTCTTGG               880
Met Leu Lys Ser Thr Ser Ile
 80                  85

CAATGGCTCA AGGTCTCCTC CGCAG CAT TGG CAC GGC TTC TTC CAG AAG GGT            932
                       His Trp His Gly Phe Phe Gln Lys Gly
                                            90

ACT AAC TGG GCT GAT GGA GCT GCC TTC GTC AAC CAG TGC CCT ATC GCG            980
Thr Asn Trp Ala Asp Gly Ala Ala Phe Val Asn Gln Cys Pro Ile Ala
 95                  100                 105                 110

ACG GGG AAC TCT TTC CTT TAC GAC TTC ACC GCG ACG GAC CAA GCA               1025
Thr Gly Asn Ser Phe Leu Tyr Asp Phe Thr Ala Thr Asp Gln Ala
                 115                 120                 125

GTCAGTGCCT GTGGCGCTTA TGTTTTCCCG TAATCAGCAG CTAACACTCC GCACCCACAG         1085

GGC ACC TTC TGG TAC CAC AGT CAC TTG TCT ACG CAG TAC TGC GAT GGT           1133
Gly Thr Phe Trp Tyr His Ser His Leu Ser Thr Gln Tyr Cys Asp Gly
             130                 135                 140

TTG CGG GGC CCG ATG GTC GTA TAC GAC CCG AGT GAC CCG CAT GCG GAC           1181
Leu Arg Gly Pro Met Val Val Tyr Asp Pro Ser Asp Pro His Ala Asp
         145                 150                 155

CTT TAC GAC GTC GAC GAC GAG ACC ACG ATC ATC ACG CTC TCT GAT TGG           1229
Leu Tyr Asp Val Asp Asp Glu Thr Thr Ile Ile Thr Leu Ser Asp Trp
 160                 165                 170

TAT CAC ACC GCT GCT TCG CTC GGT GCT GCC TTC CCG GTAAGTTTAC                1275
Tyr His Thr Ala Ala Ser Leu Gly Ala Ala Phe Pro
 175                 180                 185

CCCAGCGCAC GGAGTTAAGA CCGGATCTAA CTGTAATACG TTCAG ATT GGC TCG             1329
                                                    Ile Gly Ser

GAC TCT ACC CTG ATT AAC GGC GTTGGCCGCT TCGCGGGTGG TGACAG ACT GAC          1382
Asp Ser Thr Leu Ile Asn Gly                           Thr Asp
 190                 195

CTT GCG GTT ATC ACT GTC GAG CAG GGC AAG CGC GTTAGTGATA CCCTCTACAG         1435
Leu Ala Val Ile Thr Val Glu Gln Gly Lys Arg
 200                 205

TTGACACTGT GCCATTGCTG ACAGTACTCT CAG TAC CGT ATG CGT CTT CTC TCG         1489
                                    Tyr Arg Met Arg Leu Leu Ser
                                     210                 215

CTG TCT TGC GAC CCC AAC TAT GTC TTC TCC ATT GAC GGC CAC AAC ATG          1537
Leu Ser Cys Asp Pro Asn Tyr Val Phe Ser Ile Asp Gly His Asn Met
             220                 225                 230

ACC ATC ATC GAG GCC GAC GCC GTC AAC CAC GAG CCC CTC ACG GTT GAC          1585
Thr Ile Ile Glu Ala Asp Ala Val Asn His Glu Pro Leu Thr Val Asp
         235                 240                 245

TCC ATC CAG ATC TAC GCC GGC CAA CGT TAC TCC TTC GTC GTACGTATTC           1634
Ser Ile Gln Ile Tyr Ala Gly Gln Arg Tyr Ser Phe Val
 250                 255                 260
```

| | | |
|---|---|---|
| CGAACAGCCA TGATCACGCC AAGCCCGATG CTAACGCGCC TACCCTCAG CTT ACC | | 1689 |
| | Leu Thr | |

```
GCT GAC CAG GAC ATC GAC AAC TAC TTC ATC CGT GCC CTG CCC AGC GCC       1737
Ala Asp Gln Asp Ile Asp Asn Tyr Phe Ile Arg Ala Leu Pro Ser Ala
            265                 270                 275

GGT ACC ACC TCG TTC GAC GGC GGC ATC AAC TCG GCT ATC CTG CGC TAC       1785
Gly Thr Thr Ser Phe Asp Gly Gly Ile Asn Ser Ala Ile Leu Arg Tyr
        280                 285                 290

TCT GGT GCC TCC GAG GTT GAC CCG ACG ACC ACG GAG ACC ACG AGC GTC       1833
Ser Gly Ala Ser Glu Val Asp Pro Thr Thr Thr Glu Thr Thr Ser Val
295                 300                 305                 310

CTC CCC CTC GAC GAG GCG AAC CTC GTG CCC CTT GAC AGC CCC GCT GCT       1881
Leu Pro Leu Asp Glu Ala Asn Leu Val Pro Leu Asp Ser Pro Ala Ala
                315                 320                 325
```

| | | |
|---|---|---|
| GTACGTCGTA TTCTGCGCTT GCAAGGATCG CACATACTAA CATGCTCTTG TAG CCC | | 1937 |
| | Pro | |

```
GGT GAC CCC AAC ATT GGC GGT GTC GAC TAC GCG CTG AAC TTG GAC TTC       1985
Gly Asp Pro Asn Ile Gly Gly Val Asp Tyr Ala Leu Asn Leu Asp Phe
            330                 335                 340

AAC TTC GAT GGC ACC AAC TTC TTC ATC AAC GAC GTC TCC TTC GTG TCC       2033
Asn Phe Asp Gly Thr Asn Phe Phe Ile Asn Asp Val Ser Phe Val Ser
        345                 350                 355

CCC ACG GTC CCT GTC CTC CTC CAG ATT CTT AGC GGC ACC ACC TCC GCG       2081
Pro Thr Val Pro Val Leu Leu Gln Ile Leu Ser Gly Thr Thr Ser Ala
360                 365                 370                 375

GCC GAC CTT CTC CCC AGC GGT AGT CTC TTC GCG GTC CCG TCC AAC TCG       2129
Ala Asp Leu Leu Pro Ser Gly Ser Leu Phe Ala Val Pro Ser Asn Ser
                380                 385                 390

ACG ATC GAG ATC TCG TTC CCC ATC ACC GCG ACG AAC GCT CCC GGC GCG       2177
Thr Ile Glu Ile Ser Phe Pro Ile Thr Ala Thr Asn Ala Pro Gly Ala
            395                 400                 405

CCG CAT CCC TTC CAC TTG CAC GGT GTACGTGTCC CATCTCATAT GCTACGGAGC      2231
Pro His Pro Phe His Leu His Gly
        410                 415
```

| | | |
|---|---|---|
| TCCACGCTGA CCGCCCTATA G CAC ACC TTC TCT ATC GTT CGT ACC GCC GGC | | 2282 |
| | His Thr Phe Ser Ile Val Arg Thr Ala Gly | |
| | 420                 425 | |

```
AGC ACG GAT ACG AAC TTC GTC AAC CCC GTC CGC CGC GAC GTC GTG AAC       2330
Ser Thr Asp Thr Asn Phe Val Asn Pro Val Arg Arg Asp Val Val Asn
                430                 435                 440

ACC GGT ACC GTC GGC GAC AAC GTC ACC ATC CGC TTC ACG GTACGCAGCA        2379
Thr Gly Thr Val Gly Asp Asn Val Thr Ile Arg Phe Thr
            445                 450
```

| | | |
|---|---|---|
| CTCTCCTAAC ATTCCCACTG CGCGATCACT GACTCCTCGC CCACAG ACT GAC AAC | | 2434 |
| | Thr Asp Asn | |
| | 455 | |

```
CCC GGC CCC TGG TTC CTC CAC TGC CAC ATC GAC TTC CAC TTG GAG GCC       2482
Pro Gly Pro Trp Phe Leu His Cys His Ile Asp Phe His Leu Glu Ala
        460                 465                 470

GGT TTC GCC ATC GTC TTC AGC GAG GAC ACC GCC GAC GTC TCG AAC ACG       2530
Gly Phe Ala Ile Val Phe Ser Glu Asp Thr Ala Asp Val Ser Asn Thr
475                 480                 485
```

| | | |
|---|---|---|
| ACC ACG CCC TCG GTACGTTGTG CTCCCGTGCC CATCTCCGCG CGCCTGACTA | | 2582 |
| Thr Thr Pro Ser | | |
| 490 | | |

| | | |
|---|---|---|
| ACGAGCACCC CTTACAG ACT GCT TGG GAA GAT CTG TGC CCC ACG TAC AAC | | 2632 |
| | Thr Ala Trp Glu Asp Leu Cys Pro Thr Tyr Asn | |
| | 495                 500 | |

| | | |
|---|---|---|
| GCT CTT GAC TCA TCC GAC CTC TAATCGGTTC AAAGGGTCGC TCGCTACCTT | | 2683 |
| Ala Leu Asp Ser Ser Asp Leu | | |

```
505                     510
AGTAGGTAGA  CTTATGCACC  GGACATTATC  TACAATGGAC  TTTAATTTGG  GTTAACGGCC    2743

GTTATACATA  CGCGCACGTA  GTATAAAGGT  TCTCTGGATT  GGTCGGACCT  ACAGACTGCA    2803

ATTTTCGTGA  CCTATCAACT  GTATATTGAA  GCACGACAGT  GAATGGAAAT  AGAGACA       2860
```

( 2 ) INFORMATION FOR SEQ ID NO:8:

( i ) SEQUENCE CHARACTERISTICS:
        ( A ) LENGTH: 511 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Gly  Arg  Phe  Ser  Ser  Leu  Cys  Ala  Leu  Thr  Ala  Val  Ile  His  Ser
 1              5                        10                       15

Phe  Gly  Arg  Val  Ser  Ala  Ala  Ile  Gly  Pro  Val  Thr  Asp  Leu  Thr  Ile
          20                       25                       30

Ser  Asn  Gly  Asp  Val  Ser  Pro  Asp  Gly  Phe  Thr  Arg  Ala  Ala  Val  Leu
               35                       40                       45

Ala  Asn  Gly  Val  Phe  Pro  Gly  Pro  Leu  Ile  Thr  Gly  Asn  Lys  Gly  Asp
     50                       55                       60

Asn  Phe  Gln  Ile  Asn  Val  Ile  Asp  Asn  Leu  Ser  Asn  Glu  Thr  Met  Leu
65                       70                       75                       80

Lys  Ser  Thr  Ser  Ile  His  Trp  His  Gly  Phe  Gln  Lys  Gly  Thr  Asn
                    85                       90                       95

Trp  Ala  Asp  Gly  Ala  Ala  Phe  Val  Asn  Gln  Cys  Pro  Ile  Ala  Thr  Gly
               100                      105                      110

Asn  Ser  Phe  Leu  Tyr  Asp  Phe  Thr  Ala  Thr  Asp  Gln  Ala  Gly  Thr  Phe
          115                      120                      125

Trp  Tyr  His  Ser  His  Leu  Ser  Thr  Gln  Tyr  Cys  Asp  Gly  Leu  Arg  Gly
     130                      135                      140

Pro  Met  Val  Val  Tyr  Asp  Pro  Ser  Asp  Pro  His  Ala  Asp  Leu  Tyr  Asp
145                      150                      155                      160

Val  Asp  Asp  Glu  Thr  Thr  Ile  Ile  Thr  Leu  Ser  Asp  Trp  Tyr  His  Thr
                    165                      170                      175

Ala  Ala  Ser  Leu  Gly  Ala  Ala  Phe  Pro  Ile  Gly  Ser  Asp  Ser  Thr  Leu
               180                      185                      190

Ile  Asn  Gly  Thr  Asp  Leu  Ala  Val  Ile  Thr  Val  Glu  Gln  Gly  Lys  Arg
          195                      200                      205

Tyr  Arg  Met  Arg  Leu  Leu  Ser  Leu  Ser  Cys  Asp  Pro  Asn  Tyr  Val  Phe
     210                      215                      220

Ser  Ile  Asp  Gly  His  Asn  Met  Thr  Ile  Ile  Glu  Ala  Asp  Ala  Val  Asn
225                      230                      235                      240

His  Glu  Pro  Leu  Thr  Val  Asp  Ser  Ile  Gln  Ile  Tyr  Ala  Gly  Gln  Arg
                    245                      250                      255

Tyr  Ser  Phe  Val  Leu  Thr  Ala  Asp  Gln  Asp  Ile  Asp  Asn  Tyr  Phe  Ile
               260                      265                      270

Arg  Ala  Leu  Pro  Ser  Ala  Gly  Thr  Thr  Ser  Phe  Asp  Gly  Gly  Ile  Asn
          275                      280                      285

Ser  Ala  Ile  Leu  Arg  Tyr  Ser  Gly  Ala  Ser  Glu  Val  Asp  Pro  Thr  Thr
     290                      295                      300

Thr  Glu  Thr  Thr  Ser  Val  Leu  Pro  Leu  Asp  Glu  Ala  Asn  Leu  Val  Pro
305                      310                      315                      320
```

| | | | | | | | | | | | | |
|---|---|---|---|---|---|---|---|---|---|---|---|---|
| Leu | Asp | Ser | Pro | Ala | Ala | Pro | Gly | Asp | Pro | Asn | Ile | Gly | Gly | Val | Asp |
| | | | | 325 | | | | 330 | | | | | | 335 | |
| Tyr | Ala | Leu | Asn | Leu | Asp | Phe | Asn | Phe | Asp | Gly | Thr | Asn | Phe | Phe | Ile |
| | | | 340 | | | | | 345 | | | | | 350 | | |
| Asn | Asp | Val | Ser | Phe | Val | Ser | Pro | Thr | Val | Pro | Val | Leu | Leu | Gln | Ile |
| | | | 355 | | | | 360 | | | | | 365 | | | |
| Leu | Ser | Gly | Thr | Thr | Ser | Ala | Ala | Asp | Leu | Leu | Pro | Ser | Gly | Ser | Leu |
| | | 370 | | | | | 375 | | | | | 380 | | | |
| Phe | Ala | Val | Pro | Ser | Asn | Ser | Thr | Ile | Glu | Ile | Ser | Phe | Pro | Ile | Thr |
| 385 | | | | | 390 | | | | 395 | | | | | | 400 |
| Ala | Thr | Asn | Ala | Pro | Gly | Ala | Pro | His | Pro | Phe | His | Leu | His | Gly | His |
| | | | | 405 | | | | 410 | | | | | 415 | | |
| Thr | Phe | Ser | Ile | Val | Arg | Thr | Ala | Gly | Ser | Thr | Asp | Thr | Asn | Phe | Val |
| | | | 420 | | | | | 425 | | | | | 430 | | |
| Asn | Pro | Val | Arg | Arg | Asp | Val | Val | Asn | Thr | Gly | Thr | Val | Gly | Asp | Asn |
| | | 435 | | | | | 440 | | | | | 445 | | | |
| Val | Thr | Ile | Arg | Phe | Thr | Thr | Asp | Asn | Pro | Gly | Pro | Trp | Phe | Leu | His |
| | 450 | | | | | 455 | | | | | 460 | | | | |
| Cys | His | Ile | Asp | Phe | His | Leu | Glu | Ala | Gly | Phe | Ala | Ile | Val | Phe | Ser |
| 465 | | | | | 470 | | | | | 475 | | | | | 480 |
| Glu | Asp | Thr | Ala | Asp | Val | Ser | Asn | Thr | Thr | Thr | Pro | Ser | Thr | Ala | Trp |
| | | | | 485 | | | | | 490 | | | | | 495 | |
| Glu | Asp | Leu | Cys | Pro | Thr | Tyr | Asn | Ala | Leu | Asp | Ser | Ser | Asp | Leu | |
| | | | 500 | | | | | 505 | | | | 510 | | | |

( 2 ) INFORMATION FOR SEQ ID NO: 9:

( i ) SEQUENCE CHARACTERISTICS:
        ( A ) LENGTH: 2925 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Polyporus pinsitus ( i x ) FEATURE:
        ( A ) NAME/KEY: intron
        ( B ) LOCATION: 734..808

( i x ) FEATURE:
        ( A ) NAME/KEY: intron
        ( B ) LOCATION: 878..932

( i x ) FEATURE:
        ( A ) NAME/KEY: intron
        ( B ) LOCATION: 1051..1104

( i x ) FEATURE:
        ( A ) NAME/KEY: intron
        ( B ) LOCATION: 1219..1270

( i x ) FEATURE:
        ( A ) NAME/KEY: intron
        ( B ) LOCATION: 1336..1397

( i x ) FEATURE:
        ( A ) NAME/KEY: intron
        ( B ) LOCATION: 1713..7744

( i x ) FEATURE:
        ( A ) NAME/KEY: intron
        ( B ) LOCATION: 2030..2085

( i x ) FEATURE:
        ( A ) NAME/KEY: intron

-continued ( B ) LOCATION: 2308..2375

( i x ) FEATURE:
  ( A ) NAME/KEY: intron
  ( B ) LOCATION: 2492..2569

( i x ) FEATURE:
  ( A ) NAME/KEY: CDS
  ( B ) LOCATION: join (733..809, 877..933, 1050..1105,
    1218..1271, 2542..2600).

( x i ) SEQUENCE DESCRIPTION: SEQ ID NO: 9:

```
CTCATAACTC TTCGCTTCTA GCATGGGGGC TGCGCACACC TGACAGACCC TTCGGGAGGC      60

GAACTCGAAT GCAGCGTACT CTATCNCACC TCCAGGAAAG GTAGGGATGG ACNCCGTGCA     120

CCAACAACTG TCTCTCCACC AGCAACCATC CCTTGGATAT GTCTCCACAC ACCCGGTGTC     180

TACAAGCGGG GATCTGTGCT GGTGAAGTGC TGTCTCCGGA GCGGCGGCGG CGAGCGACCA     240

GAACCCGAAC CAGTGCTAGT GCCCGACACC CGCGAGACAA TTGTGCAGGG TGAGTTATAT     300

TCTTCGTGAG ACGGCGCTGC GCGTCGGCAC TGAAAGCGTC GCAGTTAGGT GATGCAGCGG     360

TCCGCGCTAT TTTTGACGTC TGGCAGCTAT CCTAAGCCGC GCCTCCATAC ACCCCAGGCG     420

CTCTCGTTTG CTATAGGTAT AAATCCCTCA GCTTCAGAGC GTCGATCCTC ATCCCACACG     480

ACACCCGTTT CAGTCTTCTC GTAGCGCATT CCCTAGCCGC CCAGCCTCCG CTTTCGTTTT     540

CAAC ATG GGC AAG TAT CAC TCT TTT GTG AAC GTC GTC GCC CTT AGT CTT     589
     Met Gly Lys Tyr His Ser Phe Val Asn Val Val Ala Leu Ser Leu
      1               5                  10                  15

TCT TTG AGC GGT CGT GTG TTC GGC GCC ATT GGG CCC GTC ACC GAC TTG         637
Ser Leu Ser Gly Arg Val Phe Gly Ala Ile Gly Pro Val Thr Asp Leu
                20                  25                  30

ACT ATC TCT AAC GCC GAT GTT ACG CCT GAC GGC ATT ACT CGT GCT GCT         685
Thr Ile Ser Asn Ala Asp Val Thr Pro Asp Gly Ile Thr Arg Ala Ala
                35                  40                  45

GTC CTC GCG GGC GGC GTT TTC CCC GGG CCC CTC ATT ACC GGC AAC AAG         733
Val Leu Ala Gly Gly Val Phe Pro Gly Pro Leu Ile Thr Gly Asn Lys
        50                  55                  60

GTGAGCCGCG AAACCTTCTA CTAGCGCGCT CGTACGGTGC ACCGTTACTG AAGCCACACT      793

TTGCGCTGTC AACAG GGG GAT GAA TTC CAG ATC AAT GTC ATC GAC AAC CTG       844
                 Gly Asp Glu Phe Gln Ile Asn Val Ile Asp Asn Leu
                                 65                  70                  75

ACC AAC GAG ACC ATG TTG AAG TCG ACC ACA ATC GTAAGGTGCT TGCTCCCATA     897
Thr Asn Glu Thr Met Leu Lys Ser Thr Thr Ile
                80                  85

ATTAAGCCCG TCGCTGACTC GAAGTTTATC TGTAG CAC TGG CAT GGT ATC TTC         950
                                         His Trp His Gly Ile Phe
                                                       90

CAG GCC GGC ACC AAC TGG GCA GAC GGC GCG GCC TTC GTG AAC CAG TGC         998
Gln Ala Gly Thr Asn Trp Ala Asp Gly Ala Ala Phe Val Asn Gln Cys
        95                  100                 105

CCT ATC GCC ACG GGA AAC TCG TTC TTG TAC GAC TTC ACC GTT CCT GAT        1046
Pro Ile Ala Thr Gly Asn Ser Phe Leu Tyr Asp Phe Thr Val Pro Asp
        110                 115                 120

CAA GCC GTACGTTTAT ACACTTCCCT TTCTGCGGCA TACTCTGACG CGCCGCTGGA        1102
Gln Ala
125

TCAG GGC ACC TTC TGG TAC CAC AGC CAC CTG TCC ACC CAG TAC TGT GAC       1151
     Gly Thr Phe Trp Tyr His Ser His Leu Ser Thr Gln Tyr Cys Asp
         130                 135                 140

GGC CTG CGC GGT CCT CTT GTG GTC TAC GAC CCC GAC GAT CCC AAC GCG       1199
Gly Leu Arg Gly Pro Leu Val Val Tyr Asp Pro Asp Asp Pro Asn Ala
        145                 150                 155
```

```
TCT CTT TAC GAC GTC GAT GAC GTAAGCAGGC TACTTGTGGA CTTGTATGGA           1250
Ser Leu Tyr Asp Val Asp Asp
            160

TGTATCTCAC GCTCCCCTAC AG GAT ACT ACG GTT ATT ACG CTT GCG GAC TGG      1302
                        Asp Thr Thr Val Ile Thr Leu Ala Asp Trp
                            165                 170

TAC CAC ACT GCG GCG AAG CTG GGC CCT GCC TTC CCC GTGAGTCTAC            1348
Tyr His Thr Ala Ala Lys Leu Gly Pro Ala Phe Pro
175                 180                 185

TCTTCCTCGT GTGTTAACAT AGGTGACGGC CGCTGATACG AGAGCTACCA G GCG GGT      1405
                                                        Ala Gly

CCG GAT AGC GTC TTG ATC AAT GGT CTT GGT CGG TTC TCC GGC GAT GGT       1453
Pro Asp Ser Val Leu Ile Asn Gly Leu Gly Arg Phe Ser Gly Asp Gly
        190                 195                 200

GGA GGA GCG ACA AAC CTC ACC GTG ATC ACC GTC ACG CAA GGC AAA CGG       1501
Gly Gly Ala Thr Asn Leu Thr Val Ile Thr Val Thr Gln Gly Lys Arg
205                 210                 215                 220

GTGAGTCCGC CCTGAGCTGG CCTCAATAGC GATATTGACG AGTCCATGCC CTCCCAG        1558

TAC CGC TTC CGC CTT GTG TCG ATC TCG TGC GAC CCC AAC TTC ACG TTC       1606
Tyr Arg Phe Arg Leu Val Ser Ile Ser Cys Asp Pro Asn Phe Thr Phe
                    225                 230                 235

TCG ATC GAC GGG CAC AAC ATG ACC ATC ATC GAG GTG GAC GGT GTC AAC       1654
Ser Ile Asp Gly His Asn Met Thr Ile Ile Glu Val Asp Gly Val Asn
                240                 245                 250

CAC GAG GCC TTG GAC GTC GAC TCC ATT CAG ATT TTT GCG GGG CAG CGG       1702
His Glu Ala Leu Asp Val Asp Ser Ile Gln Ile Phe Ala Gly Gln Arg
            255                 260                 265

TAC TCC TTC ATC GTACGTTCCC TTGCCCTCGT GCTATATCCG CCCGTCTGCT           1754
Tyr Ser Phe Ile
270

CACAGAGGCT TCTATATCGC AG CTC AAC GCC AAC CAG TCC ATC GAC AAC          1803
                        Leu Asn Ala Asn Gln Ser Ile Asp Asn
                                        275                 280

TAC TGG ATC CGC GCG ATC CCC AAC ACC GGT ACC ACC GAC ACC ACG GGC       1851
Tyr Trp Ile Arg Ala Ile Pro Asn Thr Gly Thr Thr Asp Thr Thr Gly
                    285                 290                 295

GGC GTG AAC TCT GCT ATT CTT CGC TAC GAC ACC GCA GAA GAT ATC GAG       1899
Gly Val Asn Ser Ala Ile Leu Arg Tyr Asp Thr Ala Glu Asp Ile Glu
            300                 305                 310

CCT ACG ACC AAC GCG ACC ACC TCC GTC ATC CCT CTC ACC GAG ACG GAT       1947
Pro Thr Thr Asn Ala Thr Thr Ser Val Ile Pro Leu Thr Glu Thr Asp
        315                 320                 325

CTG GTG CCG CTC GAC AAC CCT GCG GCT CCC GGT GAC CCC CAG GTC GGC       1995
Leu Val Pro Leu Asp Asn Pro Ala Ala Pro Gly Asp Pro Gln Val Gly
330                 335                 340                 345

GGT GTT GAC CTG GCT ATG AGT CTC GAC TTC TCC TTC GTGAGTCCCA            2041
Gly Val Asp Leu Ala Met Ser Leu Asp Phe Ser Phe
                350                 355

CAGCACTCCG CGCCATTTCG CTTATTTACG CAGGAGTATT GTTCAG AAC GGT TCC        2096
                                                    Asn Gly Ser
                                                            360

AAC TTC TTT ATC AAC AAC GAG ACC TTC GTC CCG CCC ACA GTT CCC GTG       2144
Asn Phe Phe Ile Asn Asn Glu Thr Phe Val Pro Pro Thr Val Pro Val
                365                 370                 375

CTC CTG CAG ATT TTG AGT GGT GCG CAG GAC GCG GCG AGC CTG CTC CCC       2192
Leu Leu Gln Ile Leu Ser Gly Ala Gln Asp Ala Ala Ser Leu Leu Pro
            380                 385                 390

AAC GGG AGT GTC TAC ACA CTC CCT TCG AAC TCG ACC ATT GAG ATC TCG       2240
Asn Gly Ser Val Tyr Thr Leu Pro Ser Asn Ser Thr Ile Glu Ile Ser
```

```
                  395                   400                        405
TTC CCC ATC ATC ACC ACC GAC GGT GTT CTG AAC GCG CCC GGT GCT CCG         2288
Phe Pro Ile Ile Thr Thr Asp Gly Val Leu Asn Ala Pro Gly Ala Pro
    410                 415                 420

CAC CCG TTC CAT CTC CAC GGC GTAAGTCCTT GCTTCCTCA GTGCCTCGCT             2339
His Pro Phe His Leu His Gly
425                 430

TCCACGACGT CCACTGATCC CACACATCCC ATGTGCAG CAC ACC TTC TCG GTG           2392
                                          His Thr Phe Ser Val
                                                      435

GTG CGC AGC GCC GGG AGC TCG ACC TTC AAC TAC GCC AAC CCA GTC CGC         2440
Val Arg Ser Ala Gly Ser Ser Thr Phe Asn Tyr Ala Asn Pro Val Arg
            440                 445                 450

CGG GAC ACC GTC AGT ACT GGT AAC TCT GGC GAC AAC GTC ACT ATC CGC         2488
Arg Asp Thr Val Ser Thr Gly Asn Ser Gly Asp Asn Val Thr Ile Arg
        455                 460                 465

TTC ACG GTACGTCTTC TCCGGAGCCC TCCCACCCGT GTGTCCGCTG AGCGCTGAAC          2544
Phe Thr
470

ACCGCCCACC GTGCTGCTGC TGCGCAG ACC GAC AAC CCA GGC CCG TGG TTC           2595
                             Thr Asp Asn Pro Gly Pro Trp Phe
                                             475

CTC CAC TGC CAC ATC GAC TTC CAC CTG GAG GCC GGC TTC GCC ATC GTC         2643
Leu His Cys His Ile Asp Phe His Leu Glu Ala Gly Phe Ala Ile Val
        480                 485                 490

TGG GGG GAG GAC ACT GCG GAC ACC GCG TCC GCG AAT CCC GTT CCT             2688
Trp Gly Glu Asp Thr Ala Asp Thr Ala Ser Ala Asn Pro Val Pro
495             500                 505

GTACGTCGTG CCTGCTGAGC TCTTTGTGCC CGAACAGGGT GCTGATCGTG CCTTCCTCCG       2748

TGCAG ACG GCG TGG AGC GAT TTG TGC CCC ACT TAC GAT GCT TTG GAC TCG       2798
      Thr Ala Trp Ser Asp Leu Cys Pro Thr Tyr Asp Ala Leu Asp Ser
          510                 515                 520

TCC GAC CTC TGATCGACAA GGCATGAAGG CTGAAGCAGC TGCGGTCAAT                 2847
Ser Asp Leu
525

TCTCGAACAC ACTTTACTCG AACATTCATT TTTCTTTGGC TCGGGATCGG AACAAATCAT       2907

GGGGGGGCCG GACCGTCT                                                     2925
```

( 2 ) INFORMATION FOR SEQ ID NO:10:

( i ) SEQUENCE CHARACTERISTICS:
        ( A ) LENGTH: 527 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Polyporus pinsitus ( x i ) SEQUENCE DESCRIPTION: SEQ ID NO: 10:

```
Met Gly Lys Tyr His Ser Phe Val Asn Val Val Ala Leu Ser Leu Ser
1               5                   10                  15

Leu Ser Gly Arg Val Phe Gly Ala Ile Gly Pro Val Thr Asp Leu Thr
            20                  25                  30

Ile Ser Asn Ala Asp Val Thr Pro Asp Gly Ile Thr Arg Ala Ala Val
        35                  40                  45

Leu Ala Gly Gly Val Phe Pro Gly Pro Leu Ile Thr Gly Asn Lys Gly
    50                  55                  60
```

| Asp | Glu | Phe | Gln | Ile | Asn | Val | Ile | Asp | Asn | Leu | Thr | Asn | Glu | Thr | Met |
| --- | --- | --- | --- | --- | --- | --- | --- | --- | --- | --- | --- | --- | --- | --- | --- |
| 65 | | | | 70 | | | | | 75 | | | | | | 80 |
| Leu | Lys | Ser | Thr | Thr | Ile | His | Trp | His | Gly | Ile | Phe | Gln | Ala | Gly | Thr |
| | | | | 85 | | | | | 90 | | | | | 95 | |
| Asn | Trp | Ala | Asp | Gly | Ala | Ala | Phe | Val | Asn | Gln | Cys | Pro | Ile | Ala | Thr |
| | | | 100 | | | | | 105 | | | | | 110 | | |
| Gly | Asn | Ser | Phe | Leu | Tyr | Asp | Phe | Thr | Val | Pro | Asp | Gln | Ala | Gly | Thr |
| | | | 115 | | | | | 120 | | | | 125 | | | |
| Phe | Trp | Tyr | His | Ser | His | Leu | Ser | Thr | Gln | Tyr | Cys | Asp | Gly | Leu | Arg |
| | | 130 | | | | 135 | | | | | 140 | | | | |
| Gly | Pro | Leu | Val | Val | Tyr | Asp | Pro | Asp | Pro | Asn | Ala | Ser | Leu | Tyr |
| 145 | | | | | 150 | | | | | 155 | | | | | 160 |
| Asp | Val | Asp | Asp | Asp | Thr | Thr | Val | Ile | Thr | Leu | Ala | Asp | Trp | Tyr | His |
| | | | | 165 | | | | | 170 | | | | | 175 | |
| Thr | Ala | Ala | Lys | Leu | Gly | Pro | Ala | Phe | Pro | Ala | Gly | Pro | Asp | Ser | Val |
| | | | 180 | | | | | 185 | | | | | 190 | | |
| Leu | Ile | Asn | Gly | Leu | Gly | Arg | Phe | Ser | Gly | Asp | Gly | Gly | Ala | Thr |
| | | 195 | | | | | 200 | | | | | 205 | | | |
| Asn | Leu | Thr | Val | Ile | Thr | Val | Thr | Gln | Gly | Lys | Arg | Tyr | Arg | Phe | Arg |
| | 210 | | | | | 215 | | | | | 220 | | | | |
| Leu | Val | Ser | Ile | Ser | Cys | Asp | Pro | Asn | Phe | Thr | Phe | Ser | Ile | Asp | Gly |
| 225 | | | | | 230 | | | | | 235 | | | | | 240 |
| His | Asn | Met | Thr | Ile | Ile | Glu | Val | Asp | Gly | Val | Asn | His | Glu | Ala | Leu |
| | | | | 245 | | | | | 250 | | | | | 255 | |
| Asp | Val | Asp | Ser | Ile | Gln | Ile | Phe | Ala | Gly | Gln | Arg | Tyr | Ser | Phe | Ile |
| | | | 260 | | | | | 265 | | | | | 270 | | |
| Leu | Asn | Ala | Asn | Gln | Ser | Ile | Asp | Asn | Tyr | Trp | Ile | Arg | Ala | Ile | Pro |
| | | | 275 | | | | 280 | | | | | 285 | | | |
| Asn | Thr | Gly | Thr | Thr | Asp | Thr | Gly | Gly | Val | Asn | Ser | Ala | Ile | Leu |
| | 290 | | | | | 295 | | | | | 300 | | | | |
| Arg | Tyr | Asp | Thr | Ala | Glu | Asp | Ile | Glu | Pro | Thr | Thr | Asn | Ala | Thr | Thr |
| 305 | | | | | 310 | | | | | 315 | | | | | 320 |
| Ser | Val | Ile | Pro | Leu | Thr | Glu | Thr | Asp | Leu | Val | Pro | Leu | Asp | Asn | Pro |
| | | | | 325 | | | | | 330 | | | | | 335 | |
| Ala | Ala | Pro | Gly | Asp | Pro | Gln | Val | Gly | Gly | Val | Asp | Leu | Ala | Met | Ser |
| | | | 340 | | | | | 345 | | | | | 350 | | |
| Leu | Asp | Phe | Ser | Phe | Asn | Gly | Ser | Asn | Phe | Phe | Ile | Asn | Asn | Glu | Thr |
| | | | 355 | | | | | 360 | | | | 365 | | | |
| Phe | Val | Pro | Pro | Thr | Val | Pro | Val | Leu | Leu | Gln | Ile | Leu | Ser | Gly | Ala |
| | | 370 | | | | | 375 | | | | | 380 | | | |
| Gln | Asp | Ala | Ala | Ser | Leu | Leu | Pro | Asn | Gly | Ser | Val | Tyr | Thr | Leu | Pro |
| 385 | | | | | 390 | | | | | 395 | | | | | 400 |
| Ser | Asn | Ser | Thr | Ile | Glu | Ile | Ser | Phe | Pro | Ile | Ile | Thr | Thr | Asp | Gly |
| | | | | 405 | | | | | 410 | | | | | 415 | |
| Val | Leu | Asn | Ala | Pro | Gly | Ala | Pro | His | Pro | Phe | His | Leu | His | Gly | His |
| | | | 420 | | | | | 425 | | | | | 430 | | |
| Thr | Phe | Ser | Val | Val | Arg | Ser | Ala | Gly | Ser | Ser | Thr | Phe | Asn | Tyr | Ala |
| | | 435 | | | | | 440 | | | | | 445 | | | |
| Asn | Pro | Val | Arg | Arg | Asp | Thr | Val | Ser | Thr | Gly | Asn | Ser | Gly | Asp | Asn |
| | 450 | | | | | 455 | | | | | 460 | | | | |
| Val | Thr | Ile | Arg | Phe | Thr | Thr | Asp | Asn | Pro | Gly | Pro | Trp | Phe | Leu | His |
| 465 | | | | | 470 | | | | | 475 | | | | | 480 |
| Cys | His | Ile | Asp | Phe | His | Leu | Glu | Ala | Gly | Phe | Ala | Ile | Val | Trp | Gly |
| | | | | 485 | | | | | 490 | | | | | 495 | |

-continued

| Glu | Asp | Thr | Ala | Asp | Thr | Ala | Ser | Ala | Asn | Pro | Val | Pro | Thr | Ala | Trp |
|---|---|---|---|---|---|---|---|---|---|---|---|---|---|---|---|
| | | | 500 | | | | | 505 | | | | | 510 | | |
| Ser | Asp | Leu | Cys | Pro | Thr | Tyr | Asp | Ala | Leu | Asp | Ser | Ser | Asp | Leu | |
| | | 515 | | | | | 520 | | | | | 525 | | | |

What we claim is:

1. A dye composition comprising a *Polyporus pinsitus* laccase and at least one dye precursor capable of being oxidized by the laccase in the presence of a source of oxygen.

2. The dye composition according to claim 1, wherein the laccase is encoded by a nucleic acid sequence contained in *E. coli* NRRL B-21265.

3. The dye composition according to claim 2, wherein the nucleic acid sequence is SEQ ID NO. 1.

4. The dye composition of claim 3, wherein the laccase has the amino acid sequence set forth in SEQ ID NO. 2.

5. The dye composition according to claim 1, wherein the laccase is encoded by a nucleic acid sequence contained in *E. coli* NRRL B-21266.

6. The dye composition according to claim 5, wherein the nucleic acid sequence is SEQ ID NO. 3.

7. The dye composition of claim 6, wherein the laccase has the amino acid sequence set forth in SEQ ID NO. 4.

8. The dye composition according to claim 1, wherein the laccase is encoded by a nucleic acid sequence contained in *E. coli* NRRL B-21267.

9. The dye composition according to claim 8, wherein the nucleic acid sequence is SEQ ID NO. 5.

10. The dye composition of claim 9, wherein the laccase has the amino acid sequence set forth in SEQ ID NO. 6.

11. The dye composition according to claim 1, wherein the laccase is encoded by a nucleic acid sequence contained in *E. coli* NRRL B-21264.

12. The dye composition according to claim 11, wherein the nucleic acid sequence is SEQ ID NO. 7.

13. The dye composition of claim 12, wherein the laccase has the amino acid sequence set forth in SEQ ID NO. 8.

14. The dye composition according to claim 1, wherein the laccase is encoded by a nucleic acid sequence contained in *E. coli* NRRL B-21263 or B-21268.

15. The dye composition according to claim 14, wherein the nucleic acid sequence is SEQ ID NO. 9.

16. The dye composition of claim 15, wherein the laccase has the amino acid sequence set forth in SEQ ID NO. 10.

17. The dye composition according to claim 1, further comprising at least one dye coupler.

18. A container containing a dye composition according to claim 1.

19. The container according to claim 18, wherein the dye composition further comprises at least one dye coupler.

20. A method of polymerizing or oxidizing a phenolic or aniline compound, comprising contacting the phenolic or aniline compound with a *Polyporus pinsitus* laccase and a source of oxygen.

* * * * *